US009709613B2

(12) United States Patent
Rubesa

(10) Patent No.: US 9,709,613 B2
(45) Date of Patent: Jul. 18, 2017

(54) SIGNAL CAPTURE METHOD AND APPARATUS FOR THE DETECTION OF LOW FREQUENCY ELECTRIC SIGNALS IN LIQUIDS AND BIOLOGICAL MATTER

(71) Applicant: Pier Rubesa, Grattavache (CH)

(72) Inventor: Pier Rubesa, Grattavache (CH)

(73) Assignee: Association Promethora, Grandson (CH)

( * ) Notice: Subject to any disclaimer, the term of this patent is extended or adjusted under 35 U.S.C. 154(b) by 0 days.

(21) Appl. No.: 14/413,182

(22) PCT Filed: Jul. 5, 2013

(86) PCT No.: PCT/IB2013/055513
§ 371 (c)(1),
(2) Date: Jan. 6, 2015

(87) PCT Pub. No.: WO2014/006598
PCT Pub. Date: Jan. 9, 2014

(65) Prior Publication Data
US 2015/0192627 A1     Jul. 9, 2015

(30) Foreign Application Priority Data

Jul. 6, 2012  (EP) .................................... 12175457

(51) Int. Cl.
*G01R 27/04* (2006.01)
*C12Q 1/00* (2006.01)
(Continued)

(52) U.S. Cl.
CPC ........... *G01R 23/02* (2013.01); *G01N 33/483* (2013.01); *G01N 37/005* (2013.01)

(58) Field of Classification Search
CPC ..... G01R 23/02; G01N 33/483; G01N 37/005
(Continued)

(56) References Cited

U.S. PATENT DOCUMENTS

| 2004/0185554 A1* | 9/2004 | Daitch | G01N 1/2273 435/309.1 |
| 2007/0238092 A1* | 10/2007 | Rubesa | G01N 37/005 435/4 |
| 2010/0259250 A1* | 10/2010 | Kahlman | G01R 33/093 324/207.2 |

FOREIGN PATENT DOCUMENTS

| WO | WO 03/102566 | 12/2003 |
| WO | WO 2006/048456 | 5/2006 |
| WO | WO 2010/144695 | 12/2010 |

OTHER PUBLICATIONS

International Search Report for PCT/IB2013/055513, mailed Nov. 14, 2013, 4 pages.
(Continued)

*Primary Examiner* — Farhana Hoque
(74) *Attorney, Agent, or Firm* — Nixon & Vanderhye P.C.

(57) ABSTRACT

The present invention relates to a method and apparatus intended for the detection of low frequency electric waves that can be extracted from water, organic liquids and biological matter. This field phenomenon, that we here refer to here as a "bioharmonic", is an active frequency, or harmonically related series of frequencies, that are a result of a dynamic interplay of natural processes including physical, chemical and electromagnetic interactions. We have discovered that these interactions influence the organization of signal waveform characteristics at very low frequencies. The apparatus produces a low frequency electrical wave that is coupled to a liquid or solid sample by way of a coupling electrode having a very high impedance. As the detected signal also displays field properties, the electrode does not need to be in contact with the sample in order to extract a unique signal. The resultant signal is rectified and passed through a logic gate where it is conditioned using a low pass filter on the gate output stage before amplification. A dar-
(Continued)

lington type transistor is used to amplify the signal by a minimum factor of twenty thousand.

14 Claims, 64 Drawing Sheets

(51) Int. Cl.
*G01R 23/02* (2006.01)
*G01N 37/00* (2006.01)
*G01N 33/483* (2006.01)

(58) Field of Classification Search
USPC .................................. 324/76.51, 637; 435/4
See application file for complete search history.

(56) References Cited

OTHER PUBLICATIONS

Written Opinion of the ISA for PCT/IB2013/055513, mailed Nov. 14, 2013, 5 pages.
Halse, M.E. et al., "Terrestrial Magnetic Field NMR: Recent Advances", In: Encyclopedia of Magnetic Resonance, (Mar. 15, 2009), 6 pages.

* cited by examiner

Dattes saines        Dattes parasitées

Numeric version of the circuit i) Needle in gold preferably (acupuncture)

ii) Coil (where we put a sample in the middle)

iii) Beaker of pyrex 250 ml filled with 200ml Aqua B Brown standard water

Figure 16
Figure 16a.   Frequency response
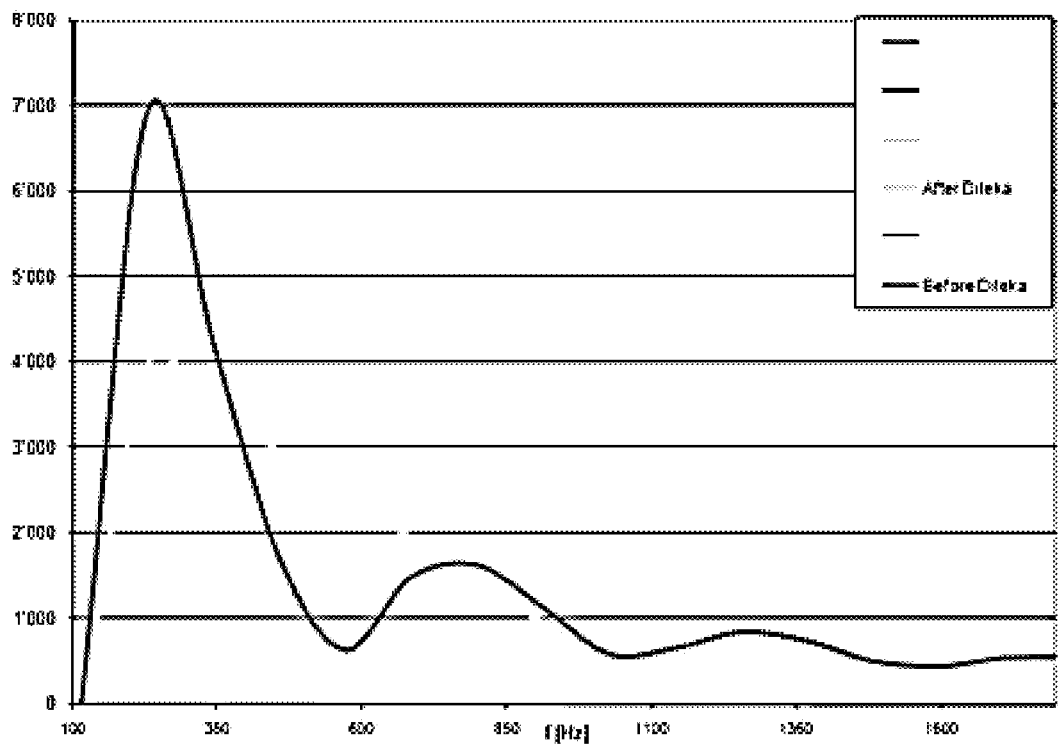
Figure 16b.   Averaged Spectral Amplitude of all tested harmonics
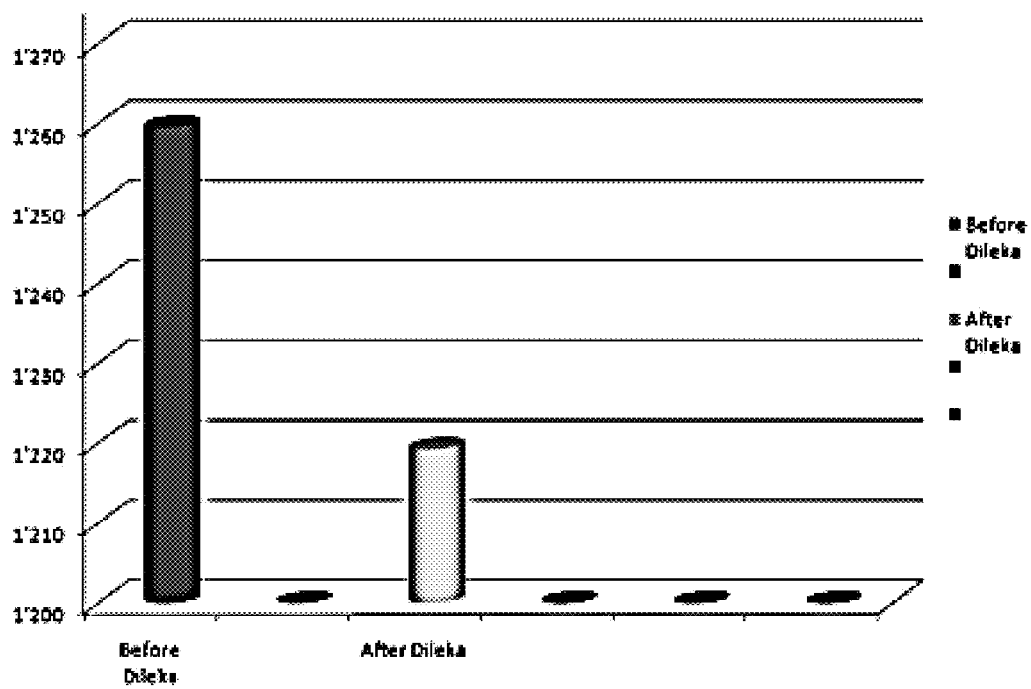

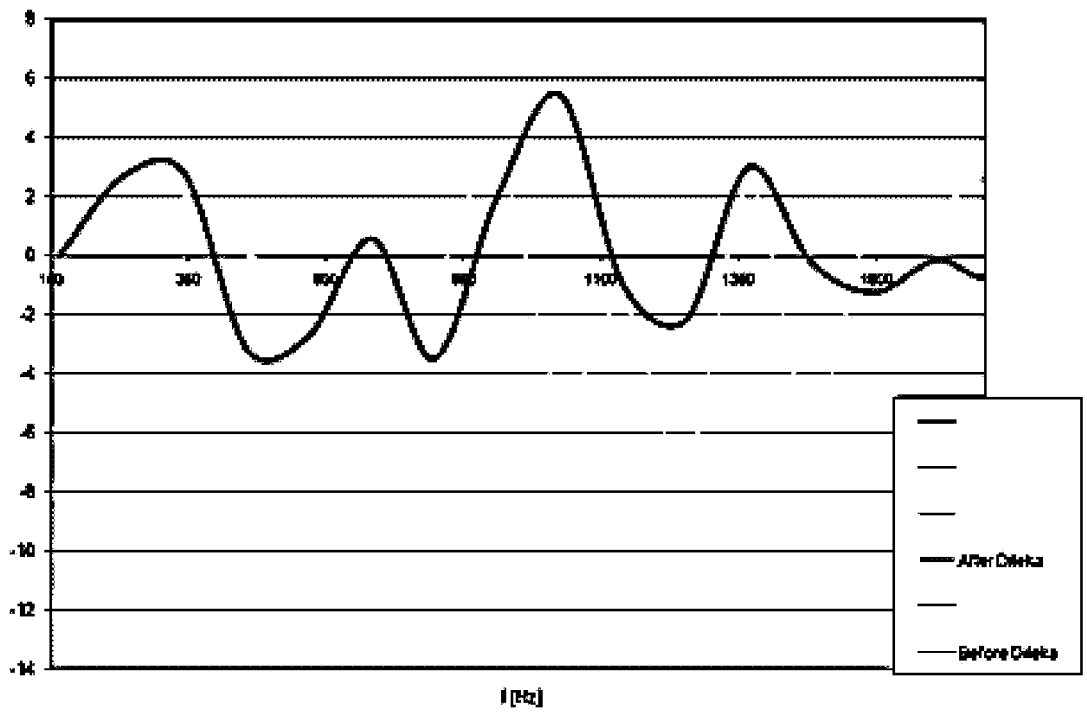
Figure 16c. Phase Response
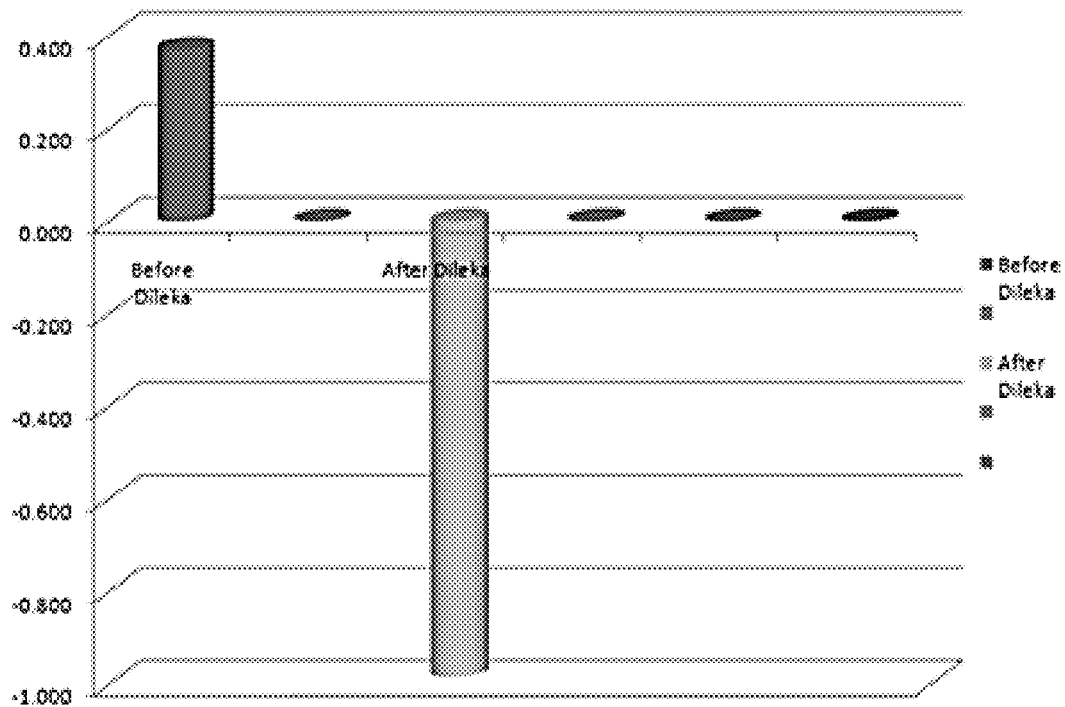
Figure 16d. Averaged Phase Response of all tested harmonics Figure 16e. Orbital Analysis - Orbital Phase Values
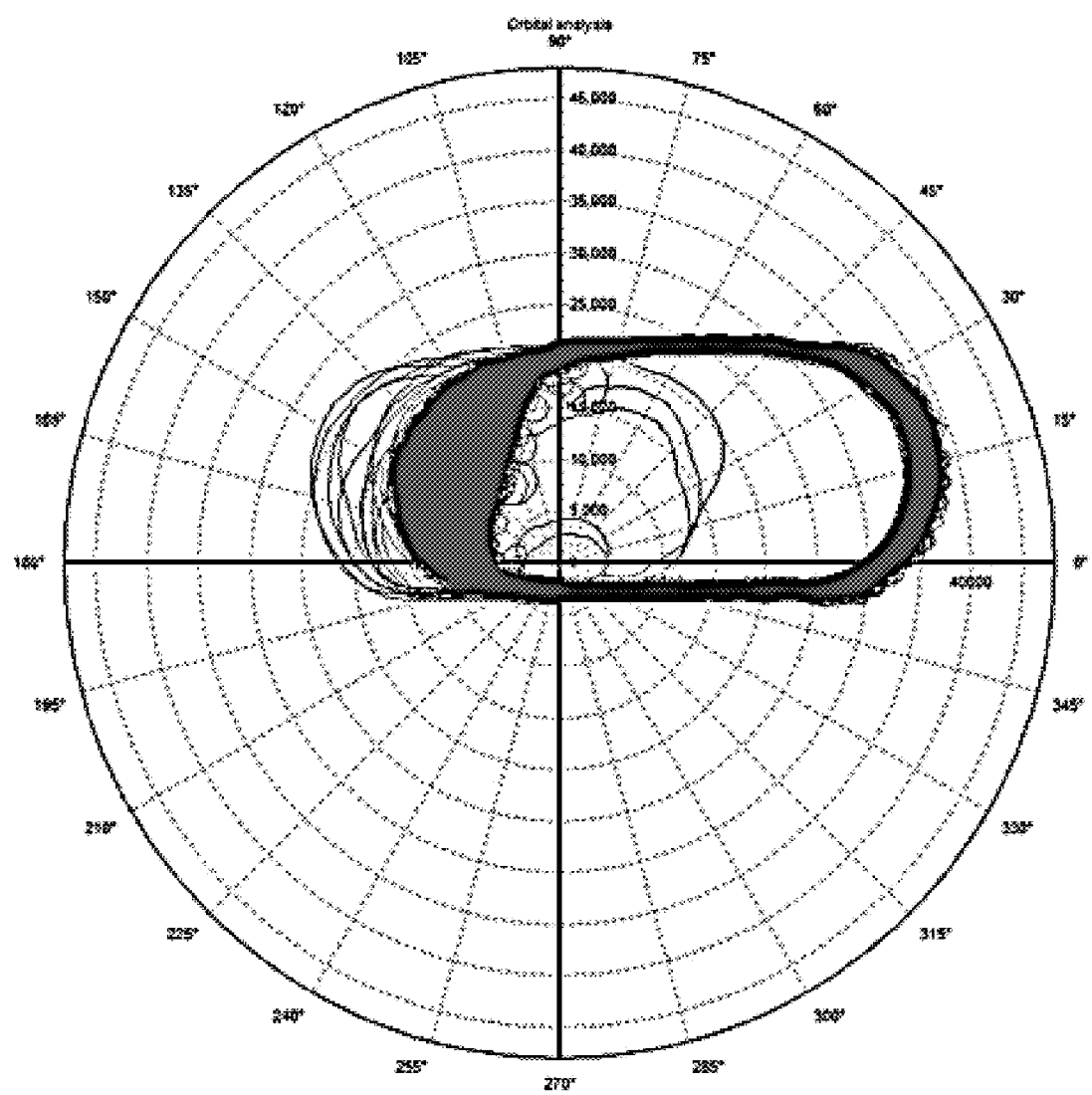

Figure 17
Characteristics of bioharmonic signals.
Bioharmonic signal zoom perspectives.
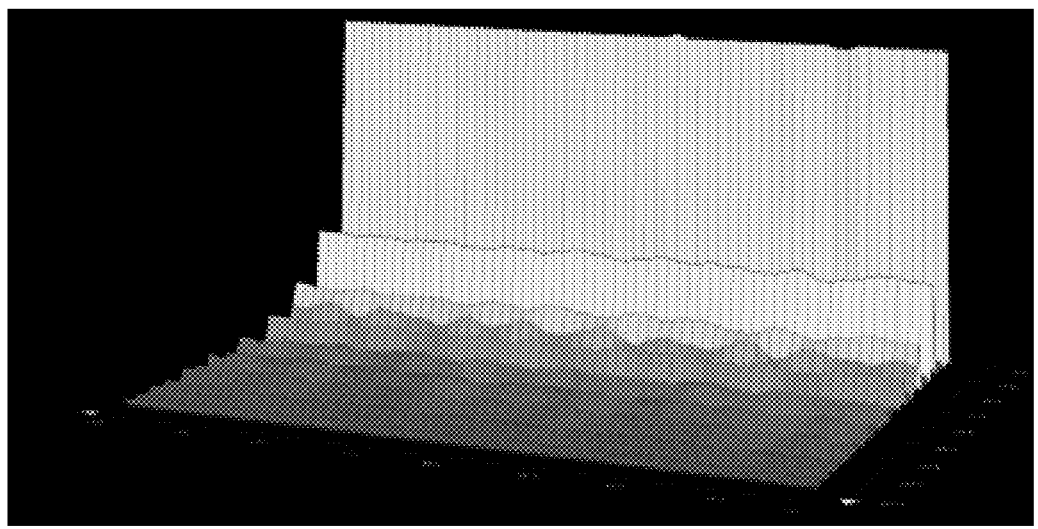
Sample 1 - Bioharmonic Reference Signal
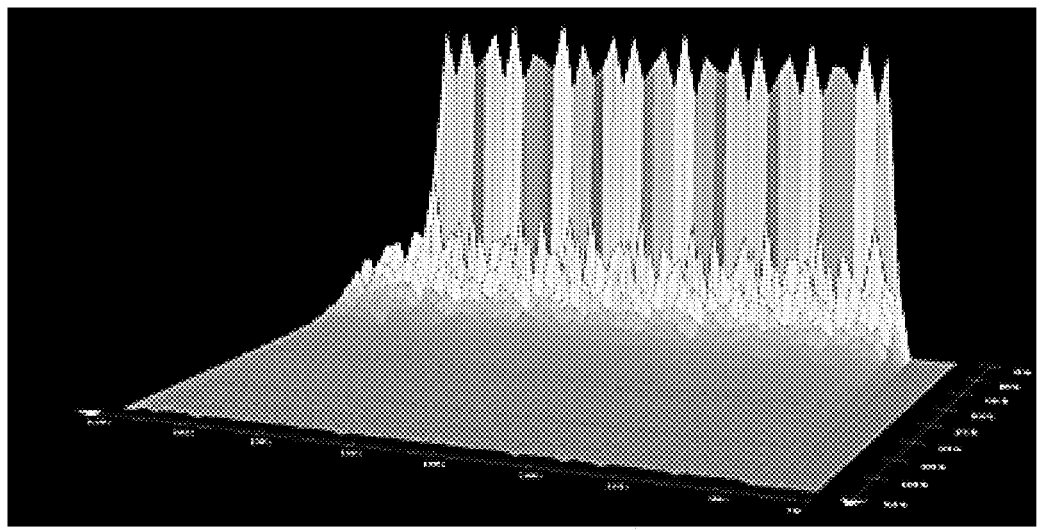
Sample 2a - Bioharmonic Signal of Plant Sample - Zoom Scale 1

Figure 18: examples of Bioharmonic Tests on Liquid and Biological samples
Characteristics of bioharmonic signals.
Bioharmonic signal zoom perspectives.
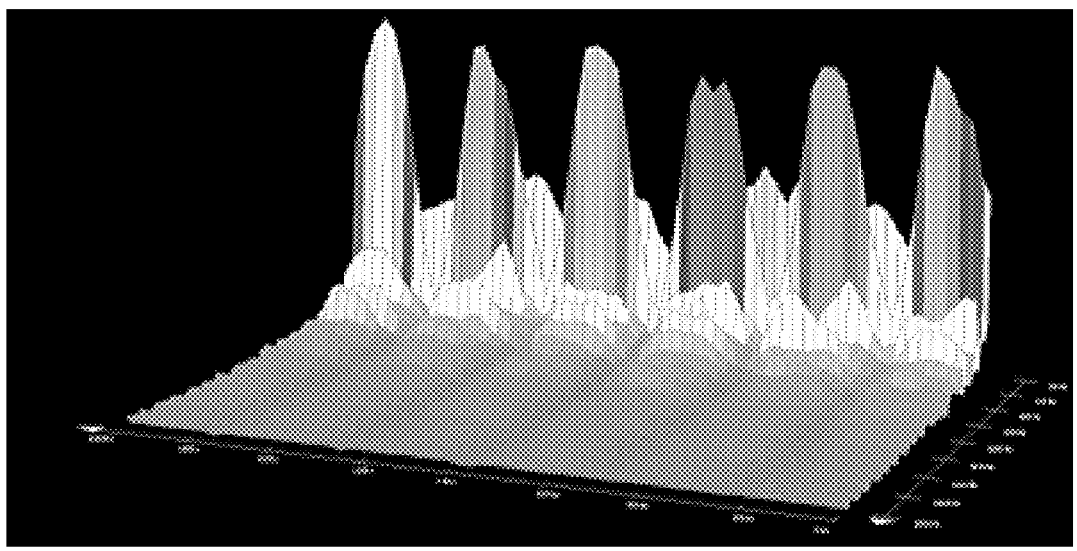
Sample 2b - Bioharmonic Signal of Plant Sample - Zoom Scale 2
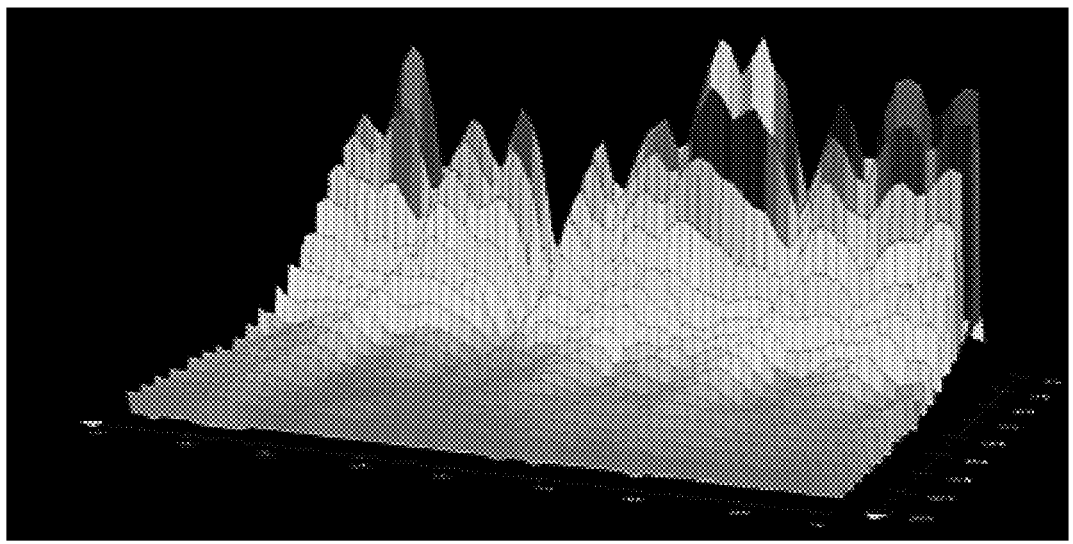
Sample 2c - Bioharmonic Signal of Plant Sample - Zoom Scale 3

Figure 19

Characteristics of bioharmonic signals.

Bioharmonic signal showing high spectral coherence.

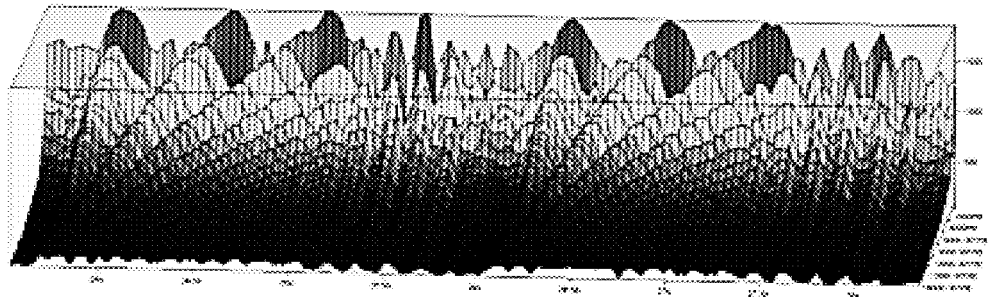

Sample 1 - Bioharmonic Signal of a tested Water Sample - Example of a highly coherent and organized electrical field measured in an informed water sample.

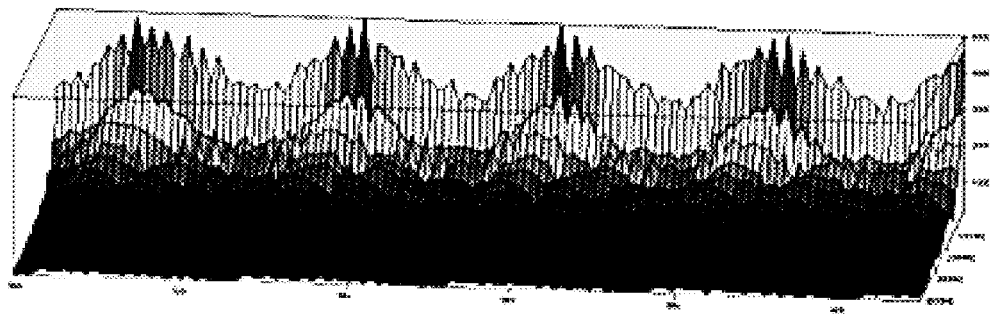

Sample 2 - Bioharmonic Signal of a tested Water Sample - Example of a highly coherent and organized electrical field measured in an informed water sample.

Figure 20

Environmental Effects
Water Reactivity Experiment showing the electrical reactivity of two water samples inside a faraday cage with the cage door open (left) and the cage door closed (right).

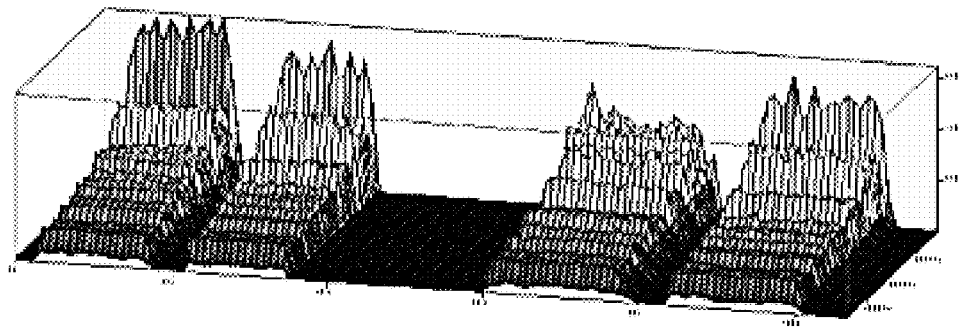

Door Open (left) - Sample 1 is normal tap water, Sample 2 is tap water containing common salt. Door Closed (right) - Sample 1 is normal tap water, Sample 2 is tap water containing common salt.

Effects of Sound
Water sample exposed to sound inside a faraday cage.

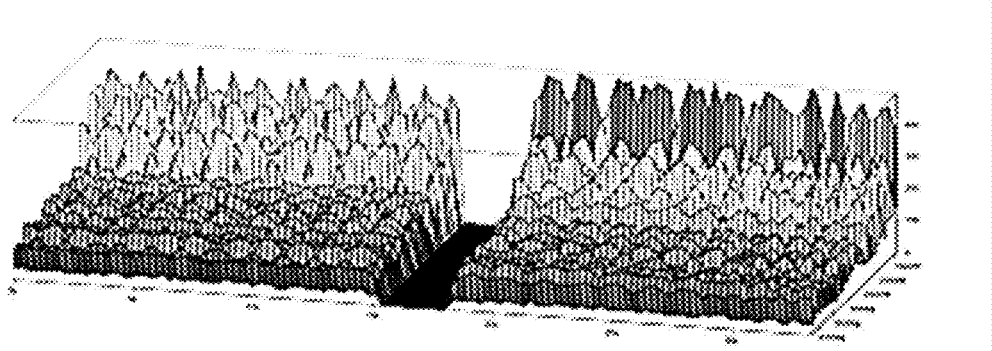

Tap water sample before sound exposure (left) and after sound exposure (right).

Effects of Magnetic Fields
Water sample exposed to a rotating magnetic field.

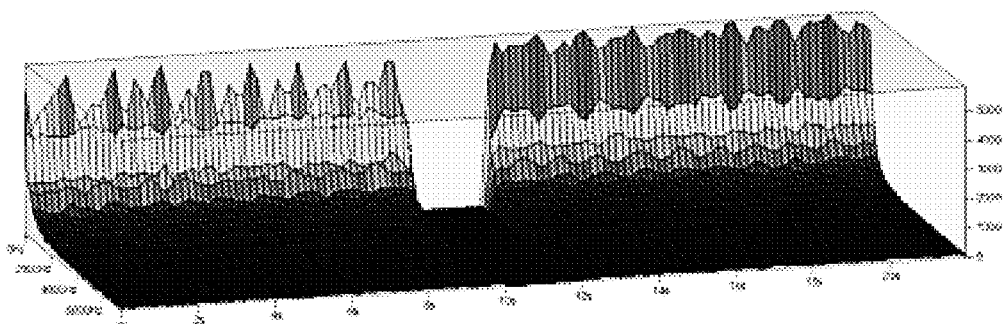

Tap water sample before magnetic field exposure (left) and after magnetic field exposure (right).

Figure 21

Water sample exposed to an ultraviolet beam from a dental lamp.

Effects of Ultraviolet Radiation

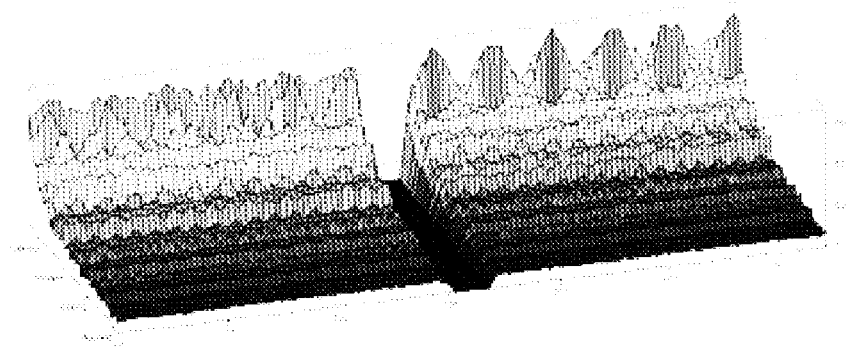

Tap water sample before exposure (left) and during exposure (right) to an ultraviolet Dental Lamp.

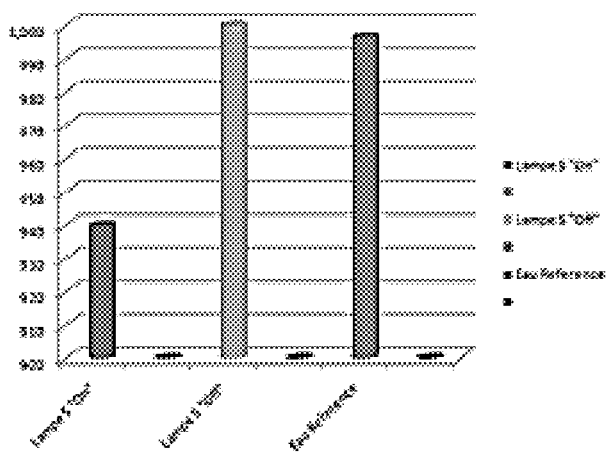

Spectral amplitude of a water sample exposed to an ultraviolet Dental Lamp.

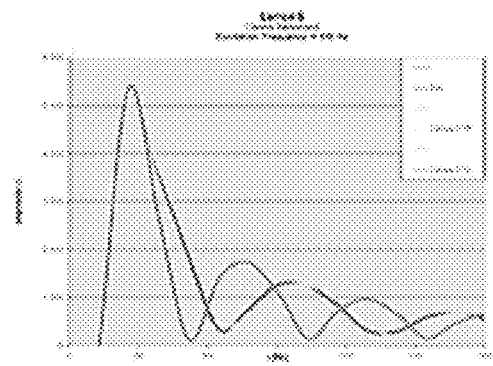

Frequency Spectrum of a water sample exposed to a an ultraviolet Dental Lamp.

Red - During Exposure
Yellow - After Exposure
Blue - Reference

Figure 22
Water sample with chemical contamination.
Heavy metal contamination.
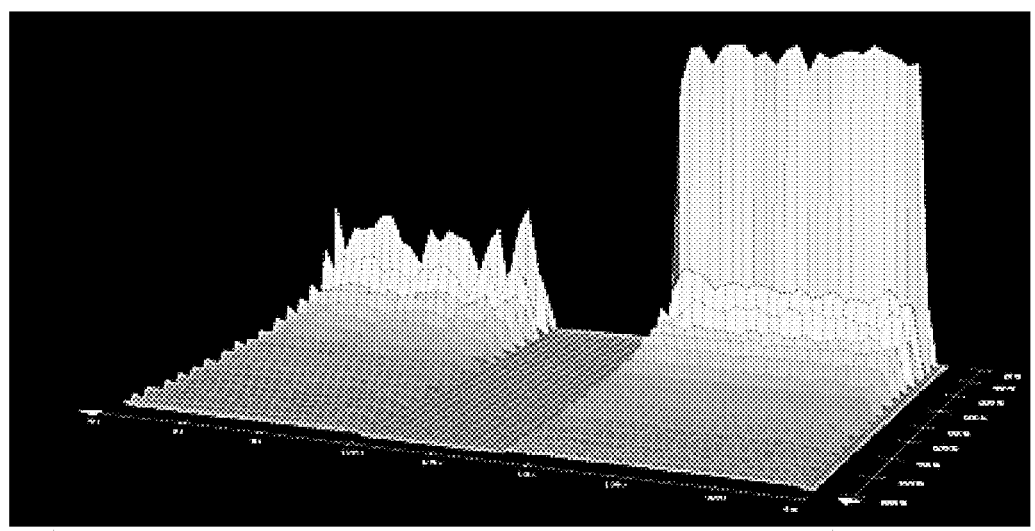
Surface Spectrum of a purified water sample (right) and same sample with cadmium chloride contamination.
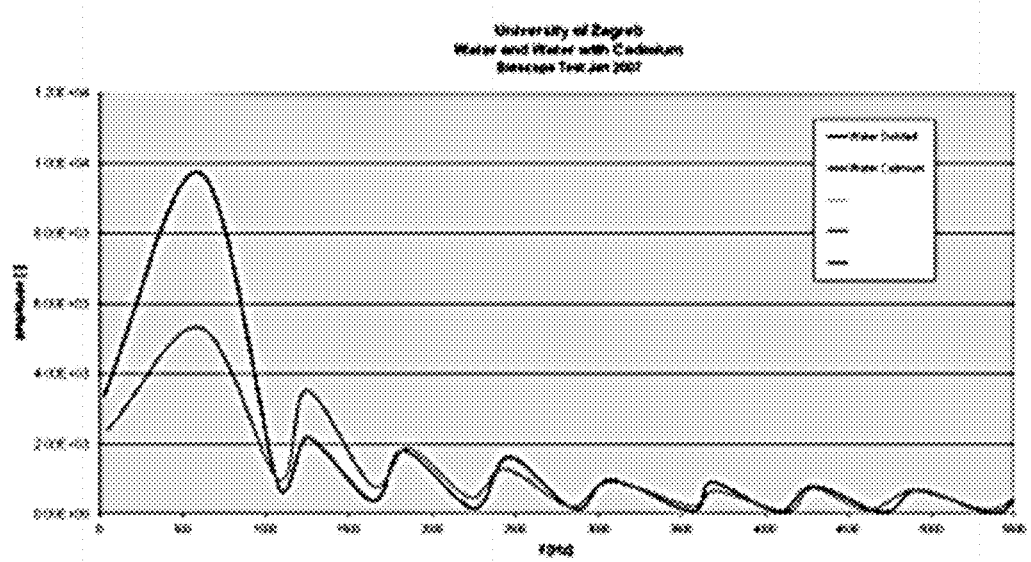
Frequency spectrum of a purified water sample (Blue) and same sample with cadmium chloride contamination (Red).

Figure 23
Water sample with chemical contamination.
Heavy metal contamination.
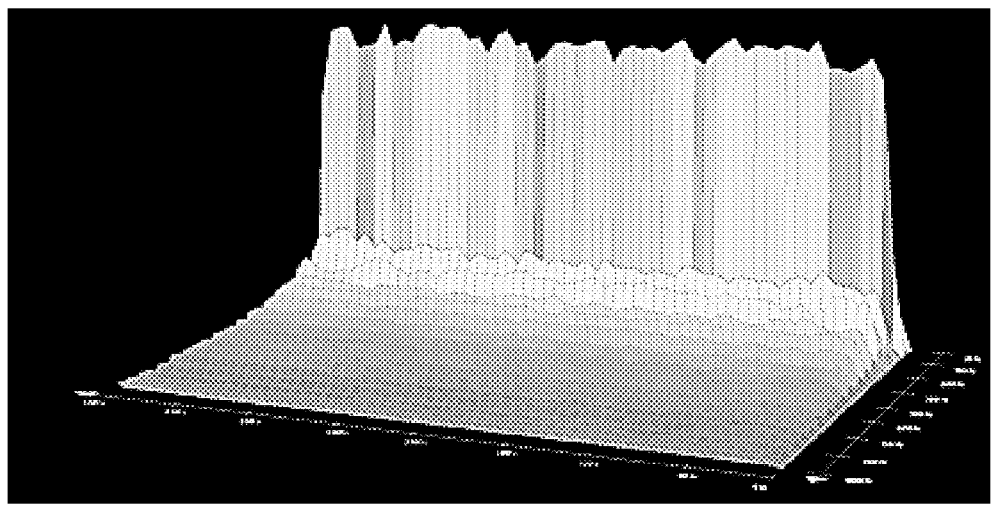
Surface Spectrum detail of purified water.
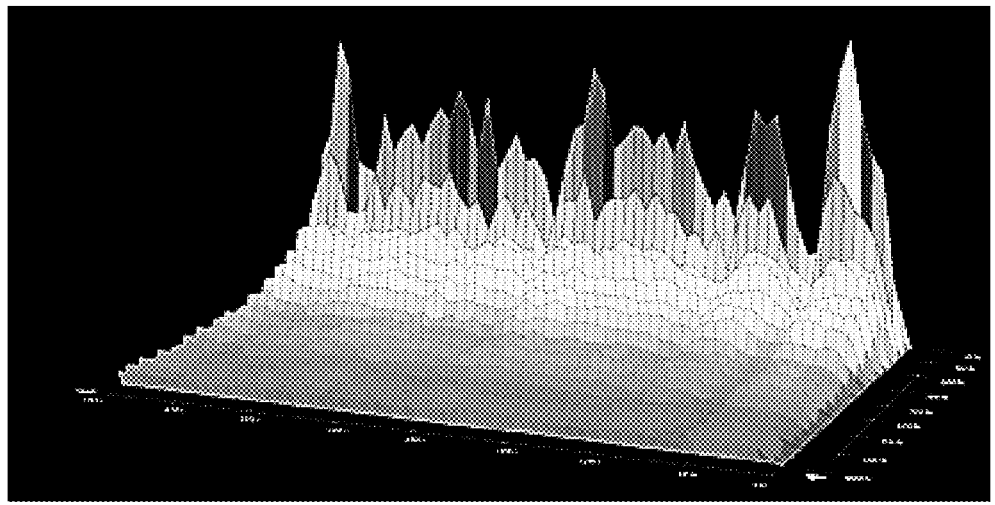
Surface Spectrum detail of purified water contaminated with cadmium chloride.

Figure 24

Water sample with increasing concentration of chemical solute.

Quantitative testing of chemical solute.

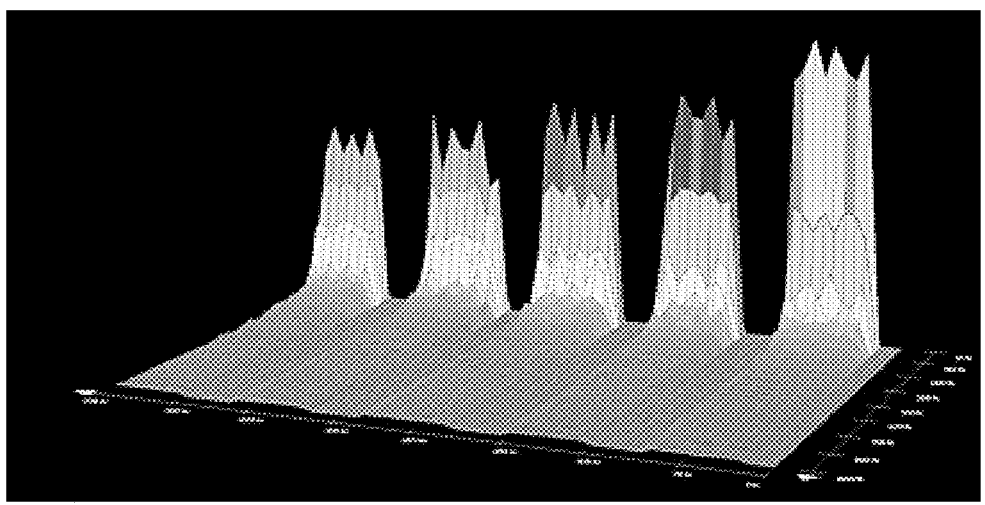

Water Testing - Concentration of Calcium carbonate (CaCO₃) in water in increasing concentrations.
(Right to Left) 1 - Purified Water Sample; 2 - Water with 20 mg $CaCO_3$; 3 - Water with 40 mg $CaCO_3$; 4 - Water with 60 mg $CaCO_3$; 5 - Water with 80 mg $CaCO_3$.

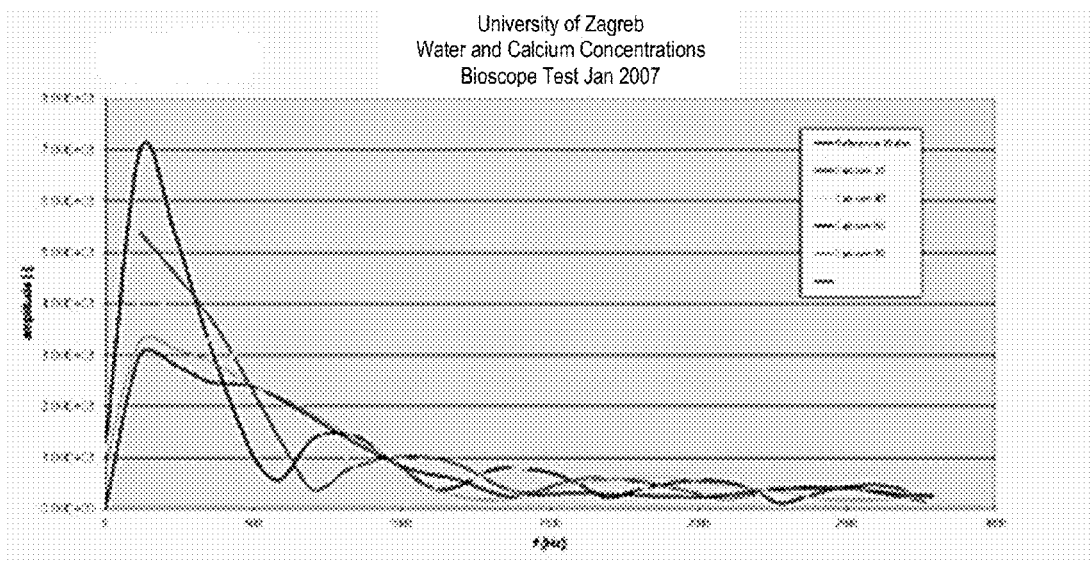

Frequency spectrum of water with varying concentrations of calcium carbonate ($CaCO_3$).

Water sample with increasing concentration of chemical solute.

Quantitative testing of chemical solute.

Figure 26
Water sample with bacterial contamination.
Escherichia coli contamination.
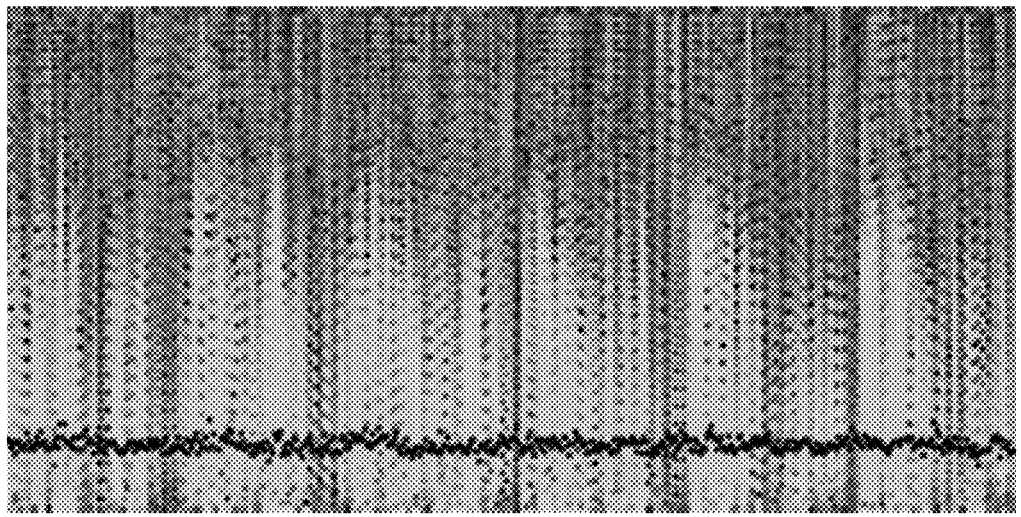
Spectrogram - Water sample 1 with Escherichia coli bacteria contamination.
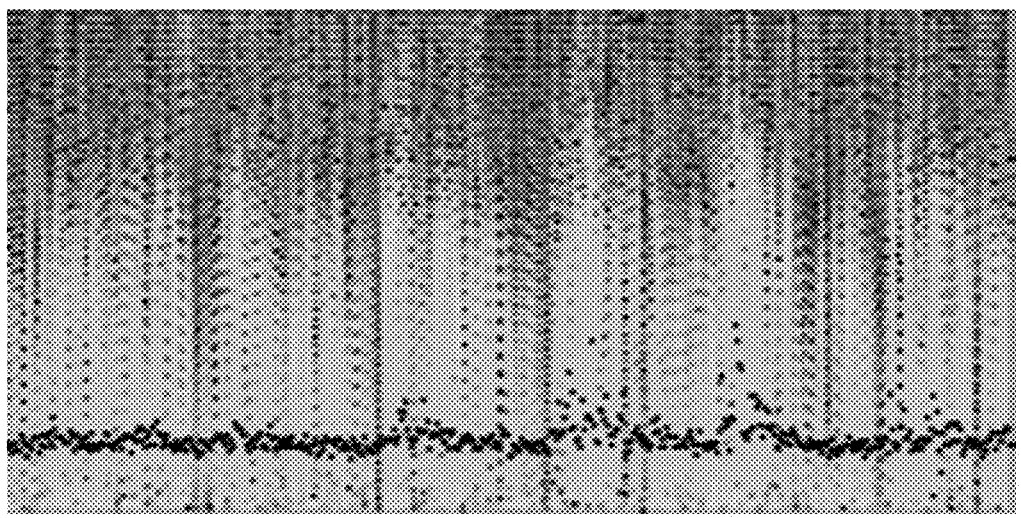
Spectrogram - Water sample 2 with Escherichia coli bacteria contamination.

Figure 27
Water sample with bacterial contamination.
Salmonella contamination.
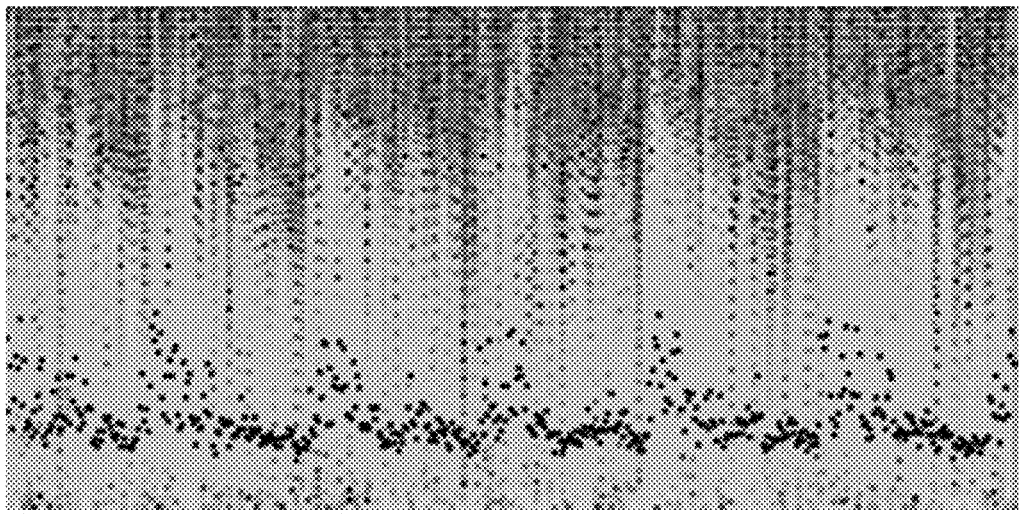
Spectrogram - Water sample 3 with Salmonella bacteria contamination.
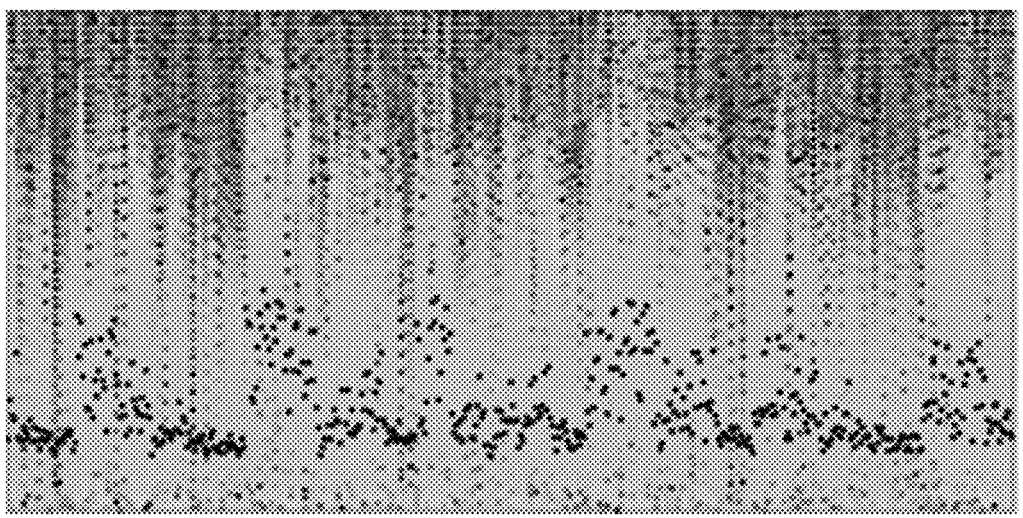
Spectrogram - Water sample 4 with Salmonella bacteria contamination.

Figure 28
Dynamised water sample containing a highly diluted organic substance.
Arnica Montana dilution 1 CH and 2 CH.
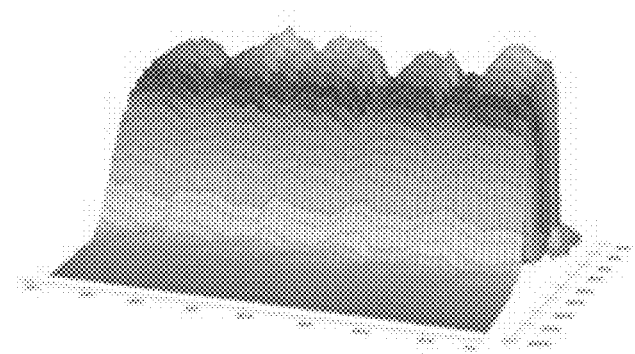
Purified and Dynamised Water sample.
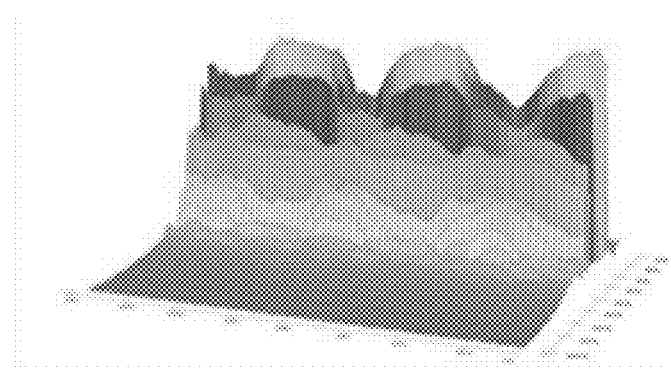
Purified and Dynamised Water sample containing a 1 CH dilution of *Arnica Montana*.
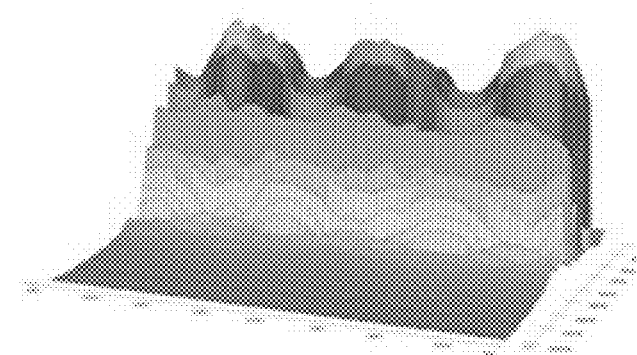
Purified and Dynamised Water sample containing a 2 CH dilution of *Arnica Montana*.

Figure 29
Electrical dynamics in water associated with a physical action.
Drop of water into a water glass.
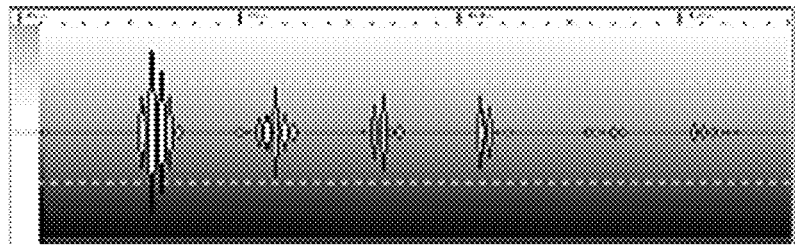
Raw bioharmonic signal of the dynamics of a drop of water into a water sample.
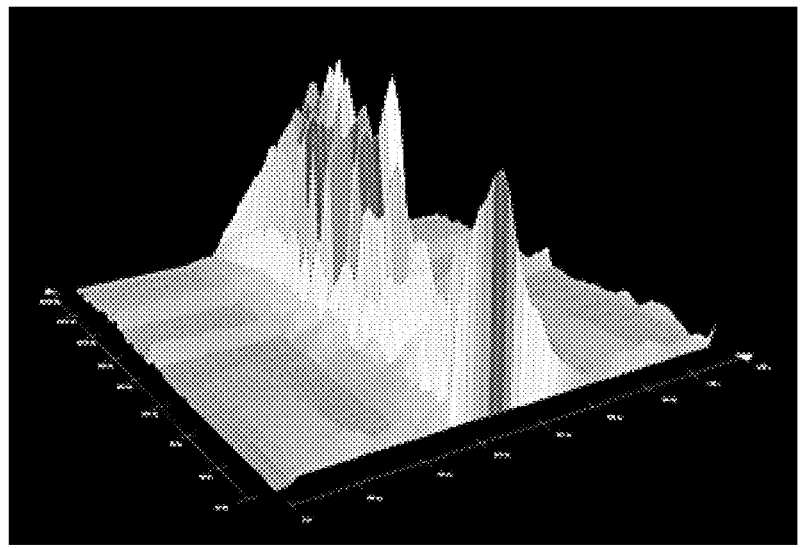
Surface spectrum of the dynamics of a drop of water into a water sample (main drop).
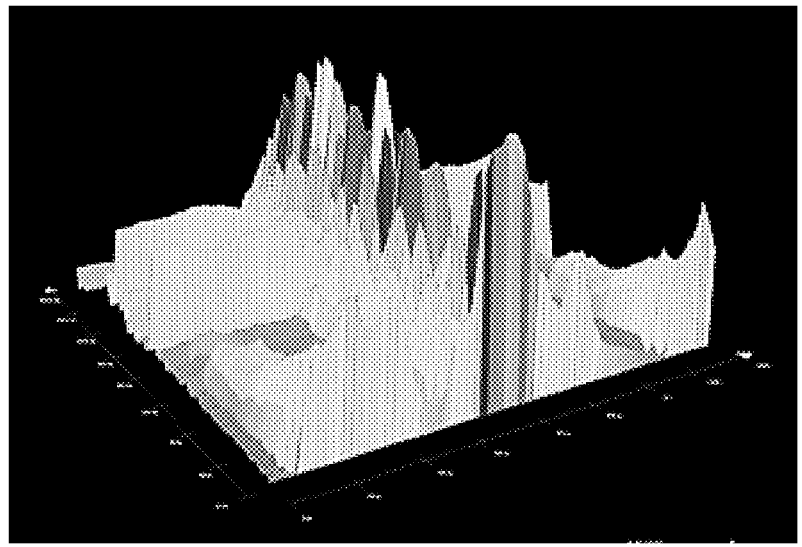
Surface spectrum of the dynamics of a drop of water into a water sample (secondary pulse).

Figure 30
Electrical dynamics of rain drops captured on a plate electrode.
Environment effects with water.
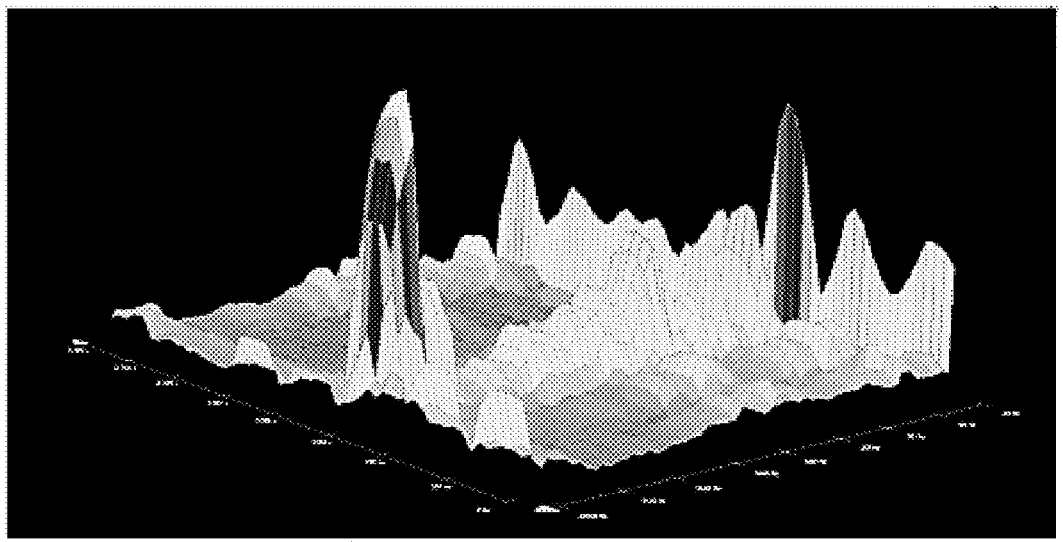
Surface spectrum of raindrops falling on a plate electrode (antenna).
Water Exposed to a Musical Sound Wave
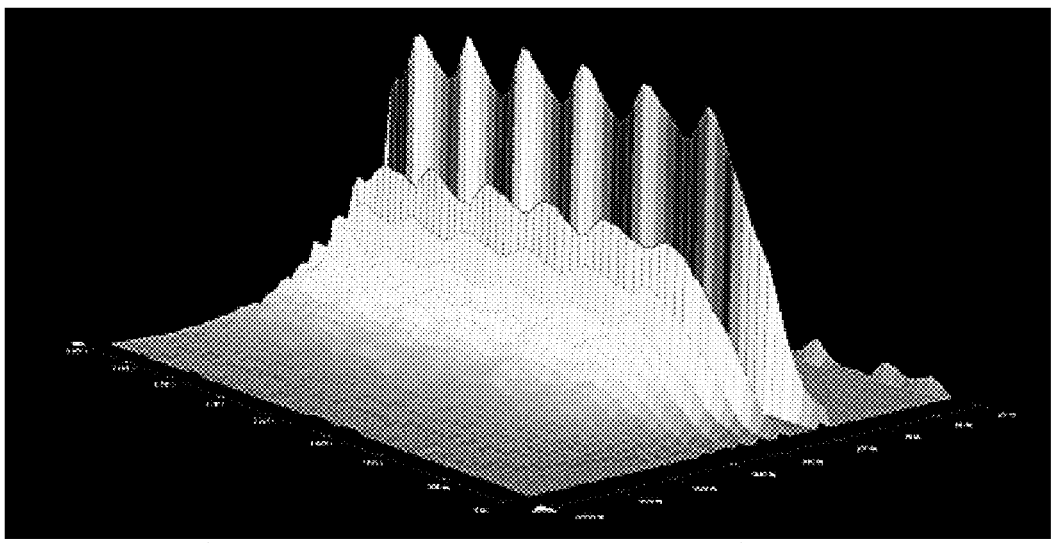
Surface spectrum of a water sample exposed to a musical note played live on a sitar.

Figure 31
Electrical dynamics in water associated with human intention (magnetisation).
Water reaction to human intention.
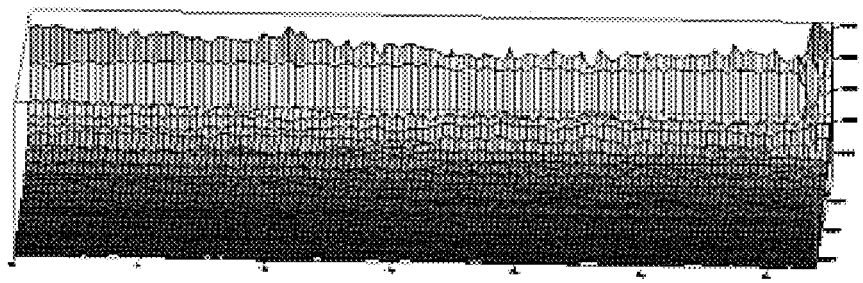
Surface Spectrum 1 of a water sample before human intention.
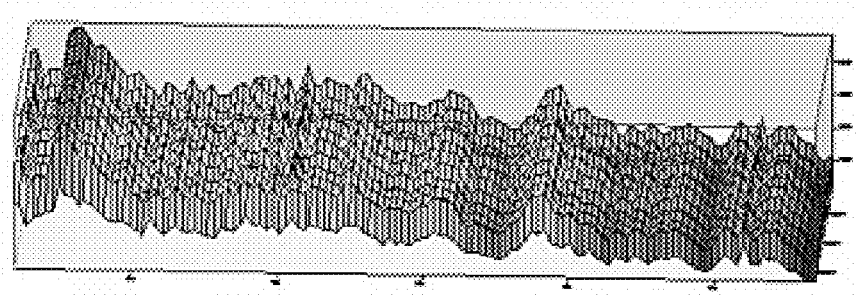
Surface Spectrum 2 of a water sample during human intention.
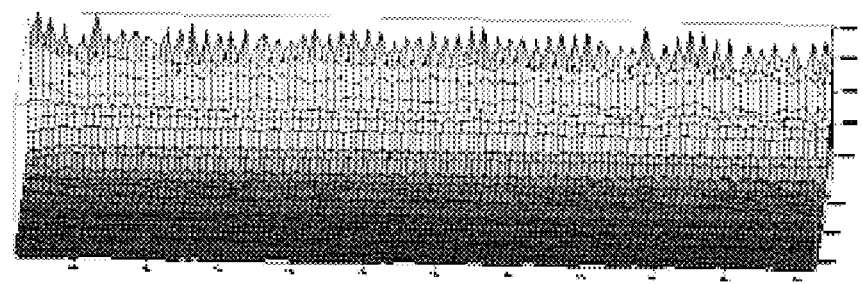
Surface Spectrum 3 of a water sample after human intention.

Figure 32
Electrical dynamics in water associated with human intention.
Water reaction to human intention - eyes open.
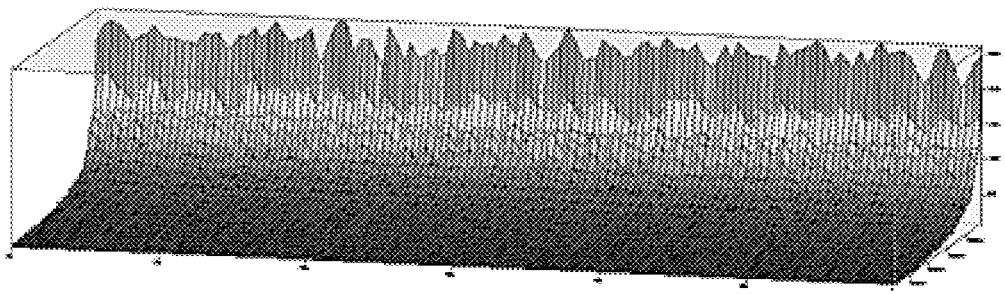
Surface Spectrum 1 of a water sample before human intention. Eyes closed.
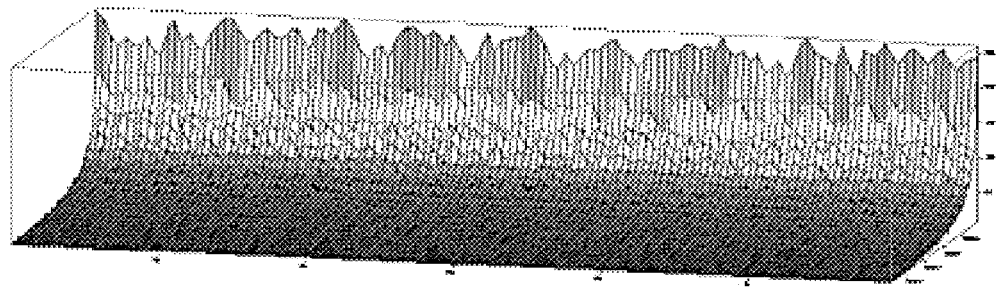
Surface Spectrum 2 of a water sample during human intention. Eyes open.
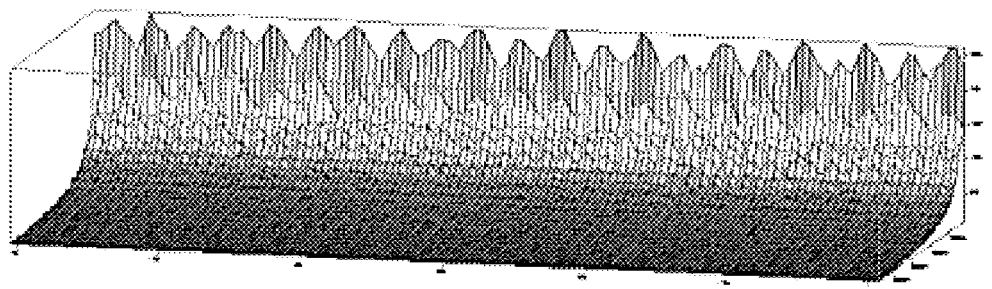
Surface Spectrum 3 of a water sample after human intention. Eyes closed.

Figure 33
Water samples tested through original packaging container.
Commercial water samples - Non-Carbonated and Carbonated.
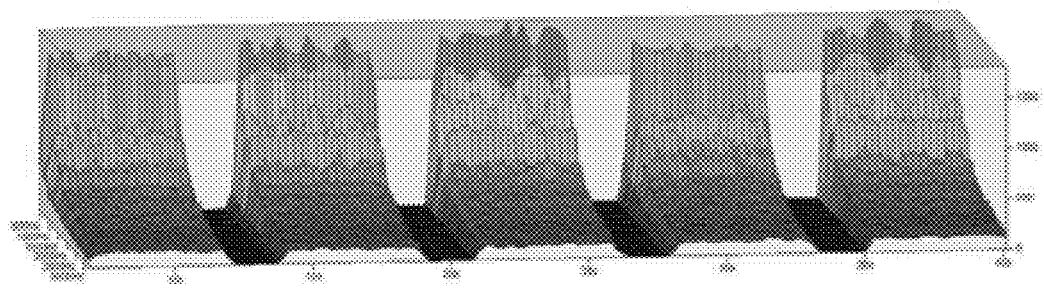
1 – Tap water (non-carbonated); 2 – Henniez Green (carbonated); 3 – Henniez Red (Carbonated); 4 – Volvic (non-carbonated); 5 – San Pellegrino (carbonated).
Figure 34
Testing of qualitative differences in wine.
Red and White Wine.
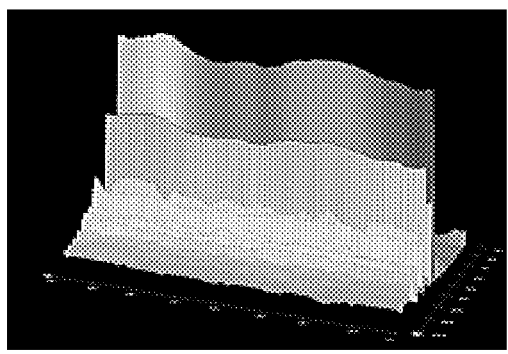 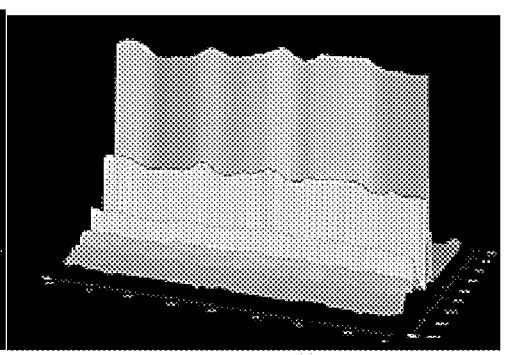
Sample 1 - Red Wine - BurgogneSample 2 - White Wine - Chablis Figure 35
Liquid testing for dangerous substances tested through a shipping container.
Water, vinegar, gasoline.
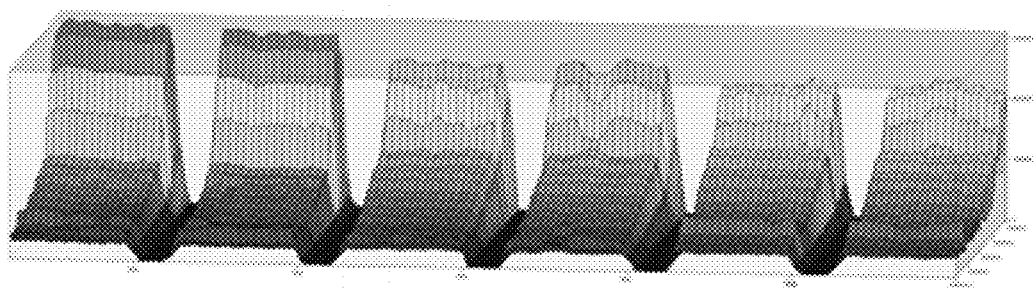
Surface Spectrum - Three liquid samples tested two times Sample 1 (left) tap water; Sample 2 (center) vinegar; Sample 1 (right) gasoline.
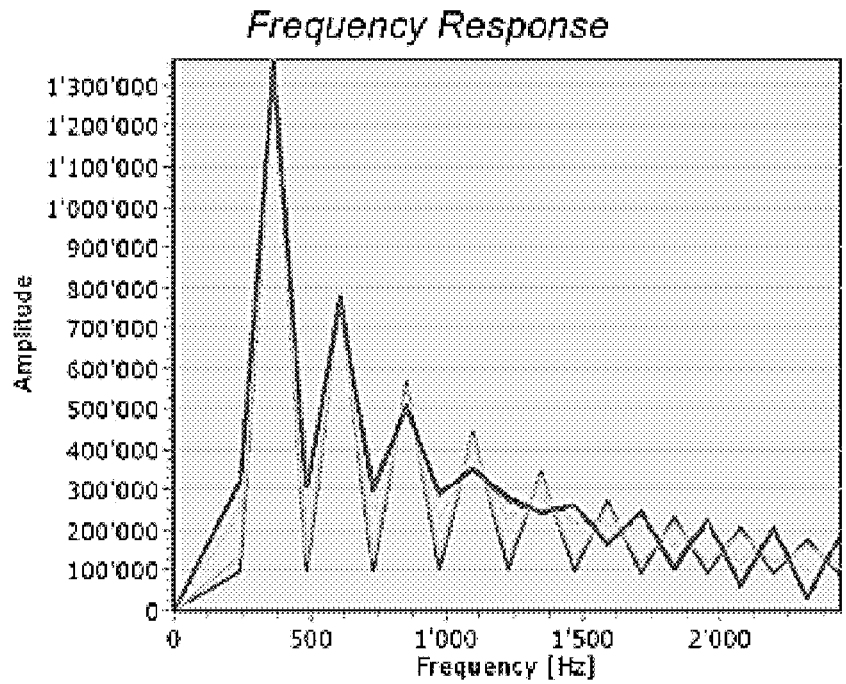
Frequency Spectrum - Three liquid samples. Tap Water; Vinegar; Gasoline showing unique frequency spectra.

Testing of bioharmonic signal in crude oil sample.

Crude oil testing.

Frequency spectrum of five different crude oil sample in reference to the atmosphere.

Figure 37
The testing of live plants and their reactions to specific stimuli.
Plant behavior.
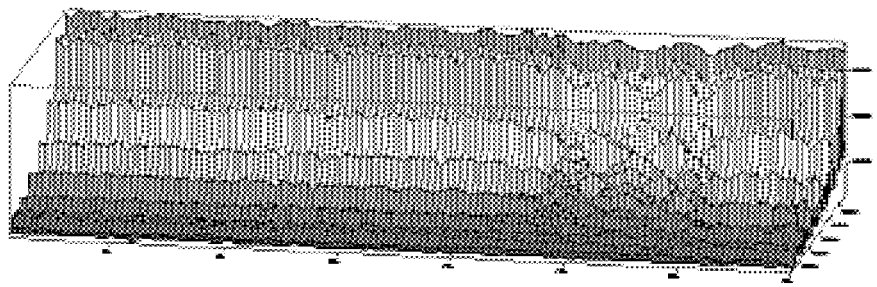
Surface Spectrum 1 - Reaction of live plant when exposed to open flame.
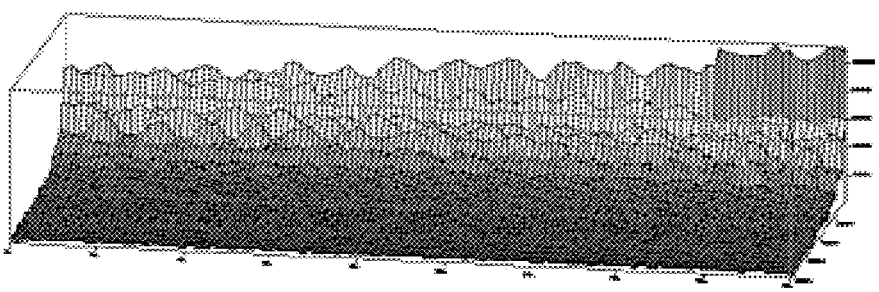
Surface Spectrum 2 - Reaction of live plant when exposed to the approach of a human and when touched by the human.

Figure 38

Bioharmonic signal of tested corn samples containing varying percentages of generically modified material (MON810).

Testing for the presence of GMOs.

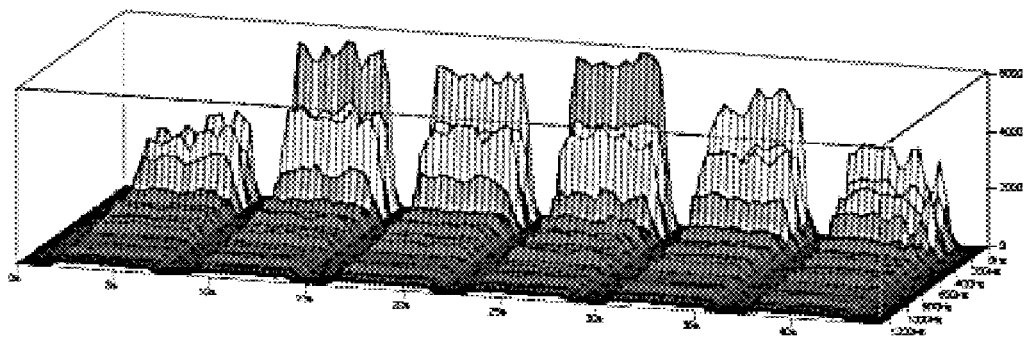

Detail

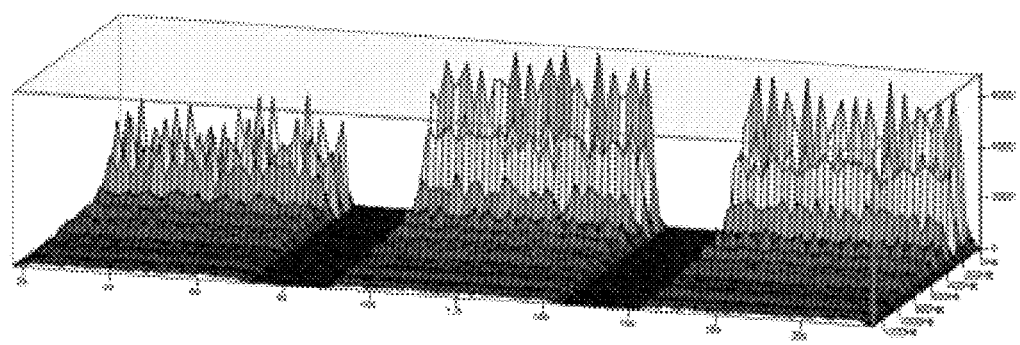

Sample 1 - Non GMO corn sample; Sample 2 - Corn sample with 0.5 % genetically modified material; Sample 3 - Corn sample with 1 % Genetically modified material.

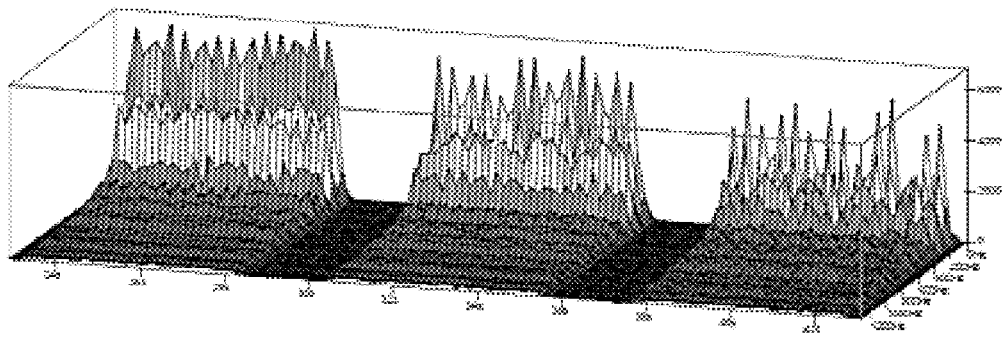

Sample 4 - Corn sample with 5 % genetically modified material; Sample 5 - Corn sample with 100 % genetically modified material; Sample 6 - Water Control Sample.

Figure 39
Genetic Modification - Examples of non modified and modified plant samples.
Testing the effects of genetic modification.
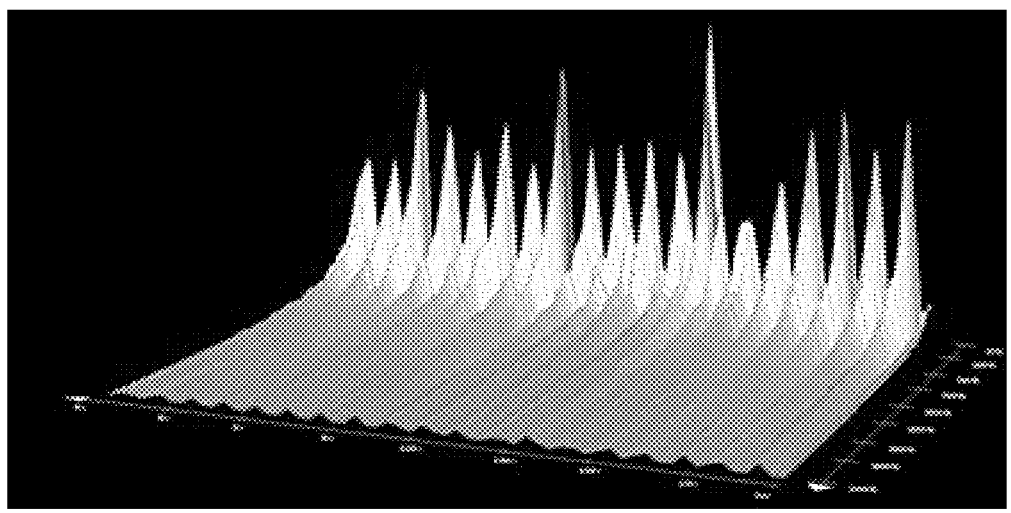
Sample 1 - Non modified clover plant (*trifolium*)
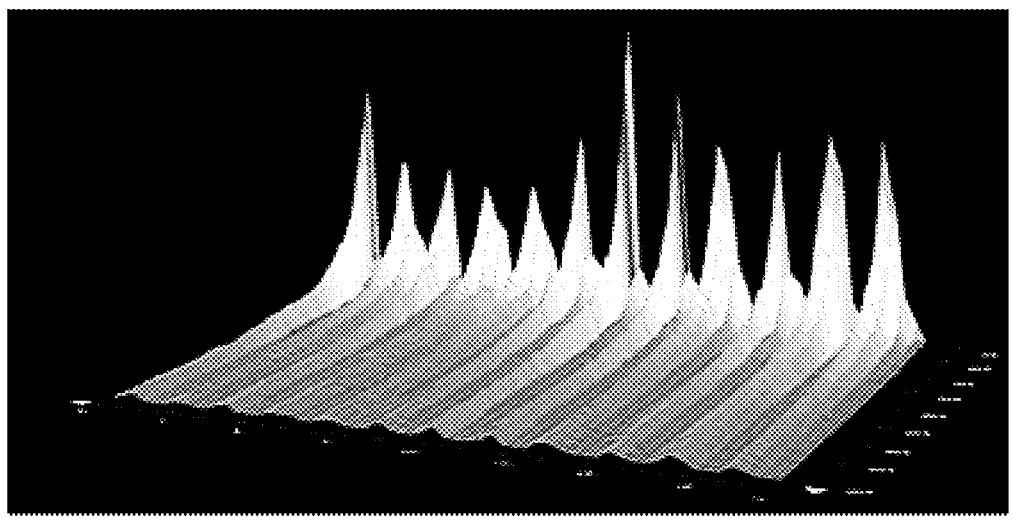
Sample 2 - Non modified clover plant (*trifolium*)

Figure 40
Genetic Modification - Examples of non modified and modified plant samples.
Testing the effects of genetic modification.
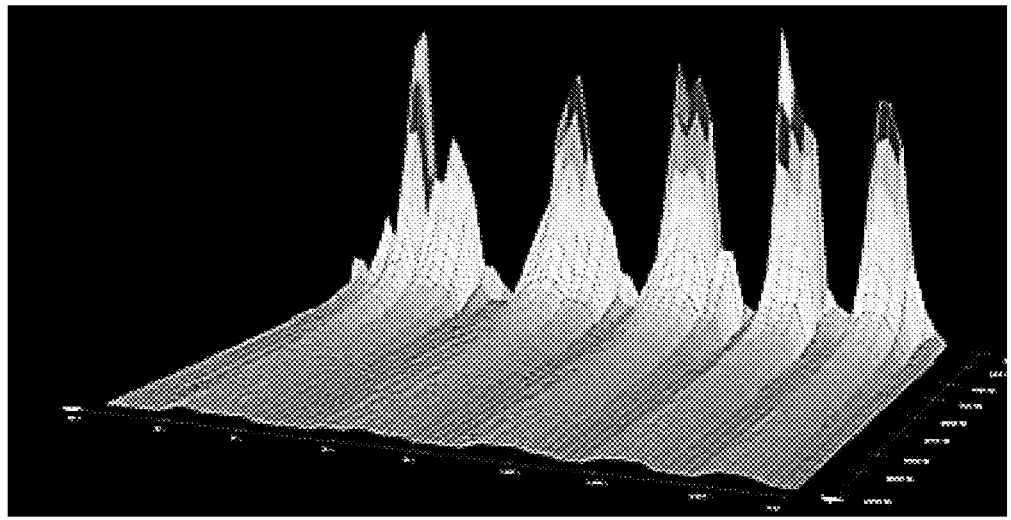
Sample 3 - Genetically modified clover plant (*trifolium*)
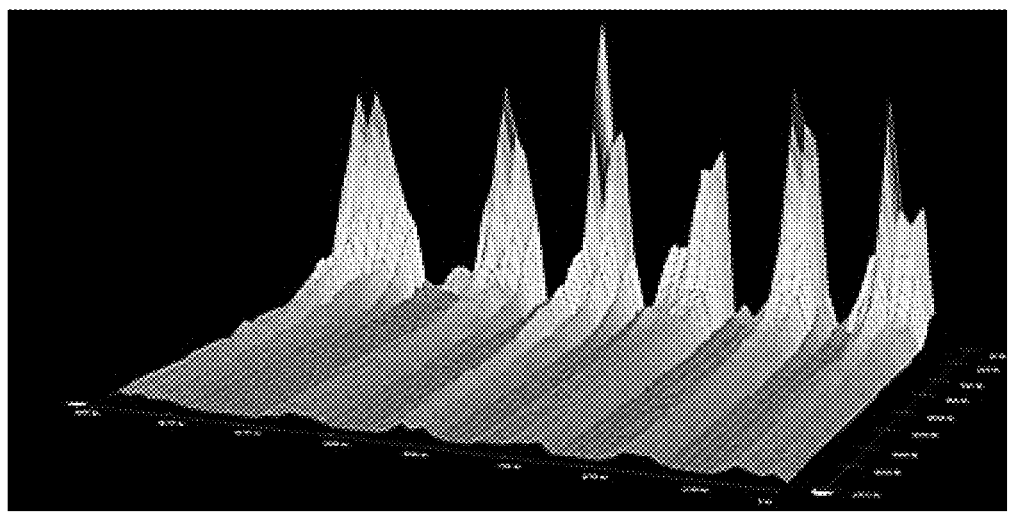
Sample 4 - Genetically modified clover plant (*trifolium*)

Figure 41
Testing of organic toxins.
Aflatoxin contamination.
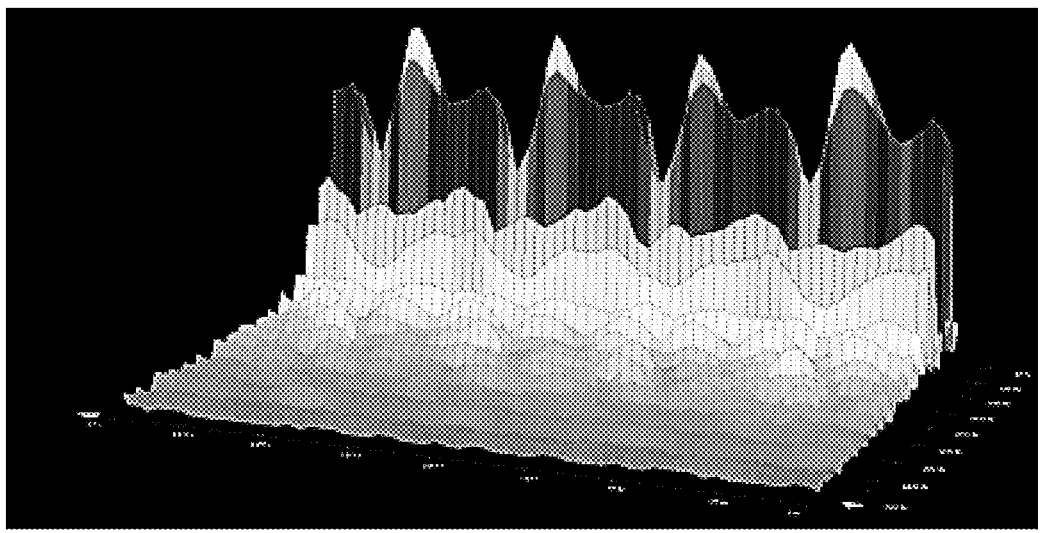
Sample 1 - Dried Fig (*Ficus carica*) Sample - Normal.
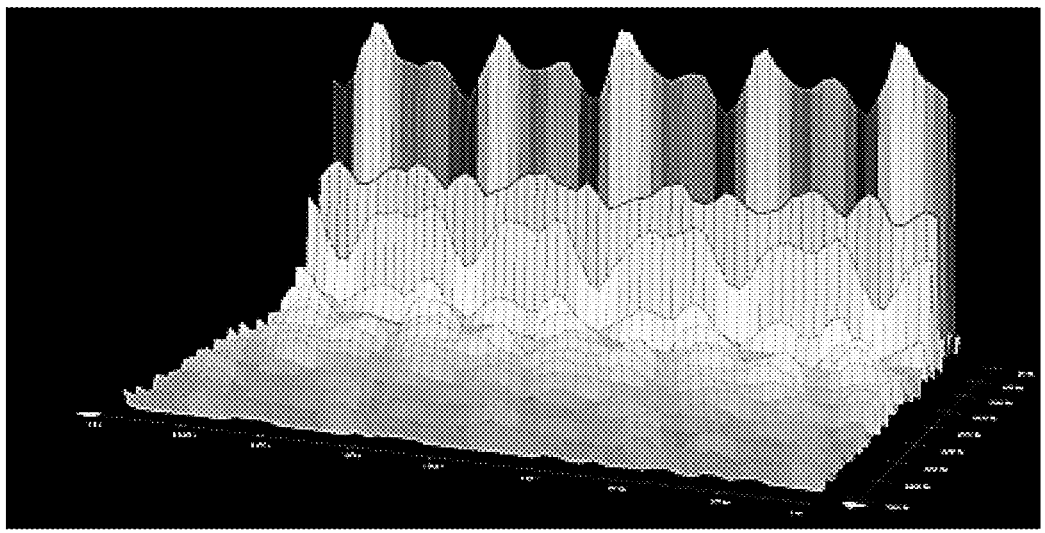
Sample 2 - Dried Fig (*Ficus carica*) Sample - Contaminated with *aflatoxin*.

Figure 42
Testing of plant parasites.
Tomato plant roots.
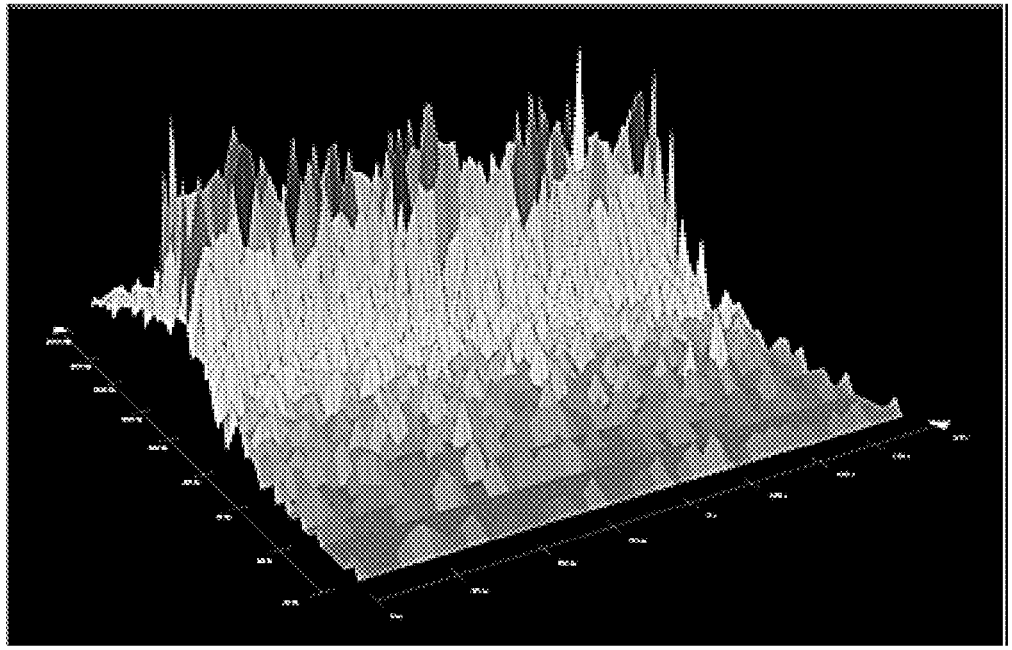
Sample 1 - Tomato plant (*Solanum lycopersicum*) root - Normal Plant
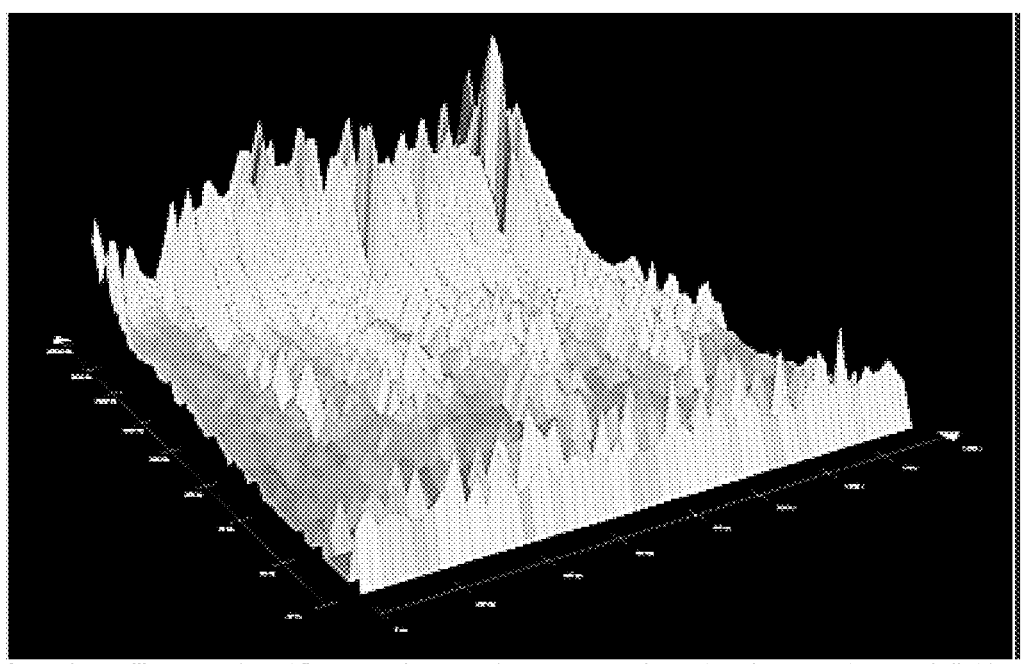
Sample 2 - Tomato plant (*Solanum lycopersicum*) root- Infected corky root disease (*Xiphinema bakeri*).

Figure 43
Groups of organic dates.
Plant insect infestation testing.
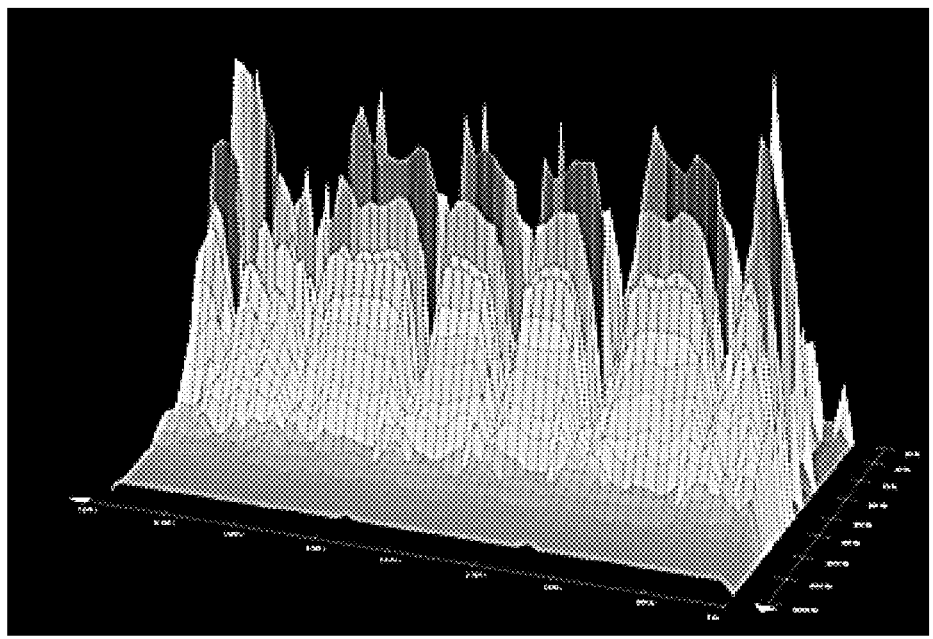
Sample Group 1 - Dried Date Samples (*Phoenix canariensis*) - Normal Samples
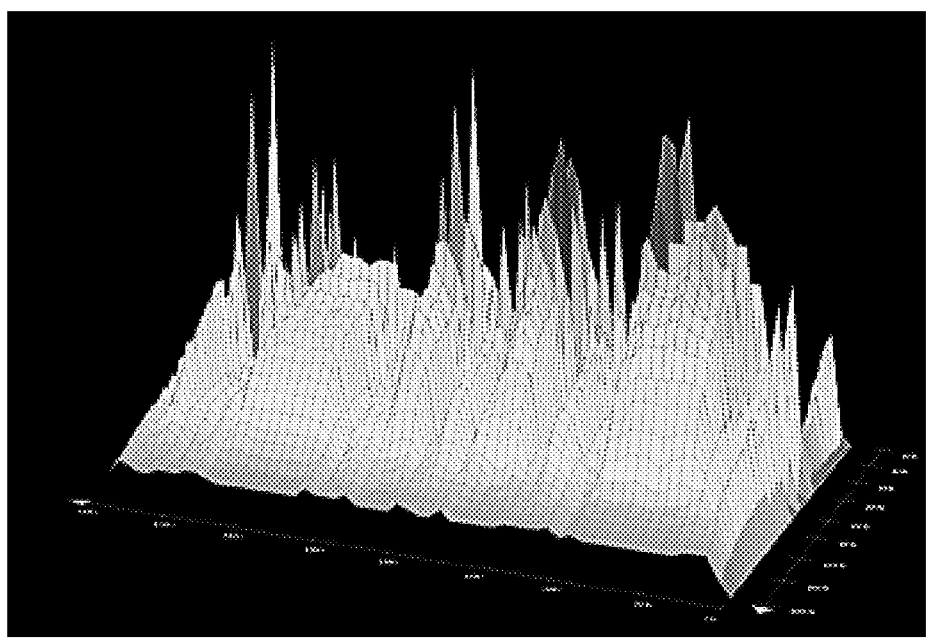
Sample Group 2 - Dried Date Samples (*Phoenix canariensis*) - Samples infested with red palm weevil (*Rhynchophorus ferrugineus*).

Figure 44

Tomato plant stems and leaves

Plant disease testing.

Sample 1 - Hothouse Tomato Plant (*Solanum lycopersicum*) Stem - Normal Plant

Sample 2 - Hothouse Tomato Plant (*Solanum lycopersicum*) Stem - Plant infected with *Tospovirus*.

Figure 45
Grape Vine Samples stems and leaves normal and diseased.
Variety and quality testing.
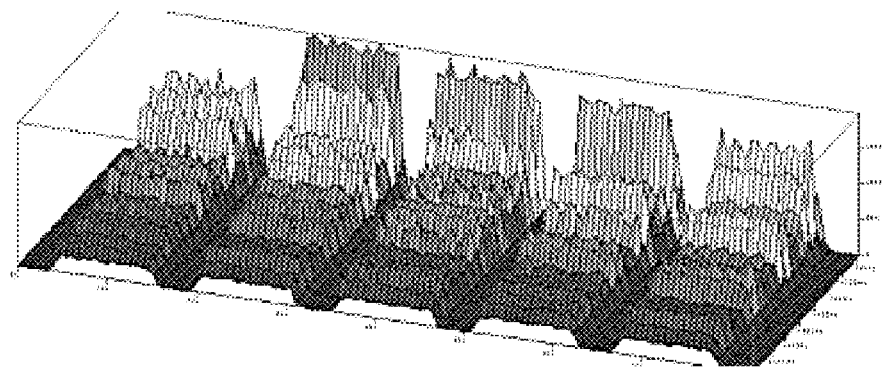
Sample 1 Control; Sample 2 - A; Sample 3 - B; Sample 4 - C; Sample 5 - D.
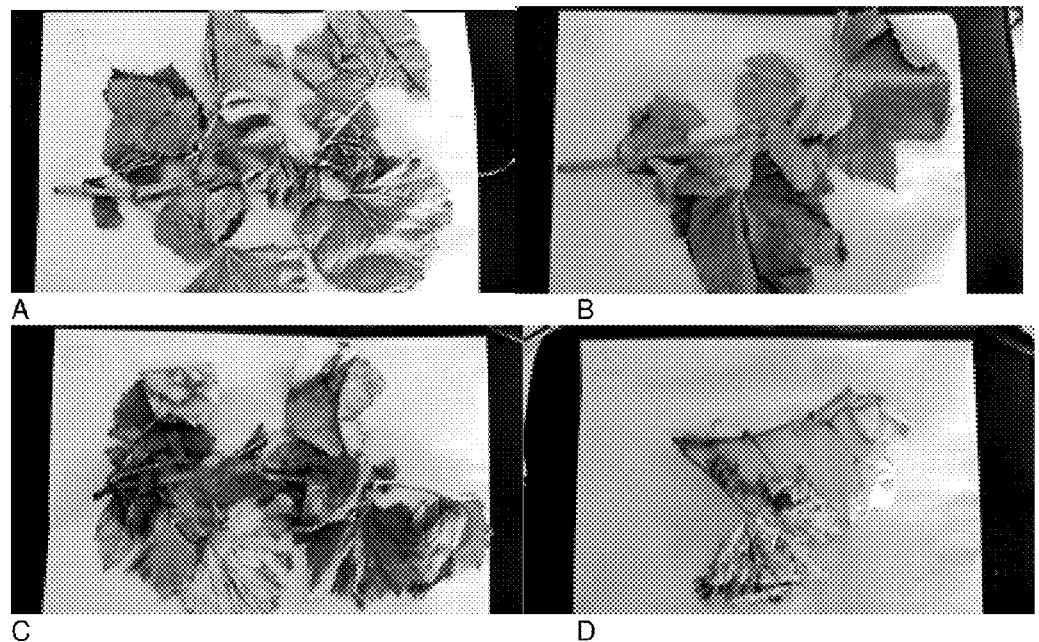
Sample "A" Houilleres - normal.
Sample "B" Poucelles - normal.
Sample "C" Batard - diseased.
Sample "D" Chevalier - diseased.

Figure 46
Lavender (*lavandula*) Samples of whole plant normal and diseased samples.
Testing of pathogens in plants.
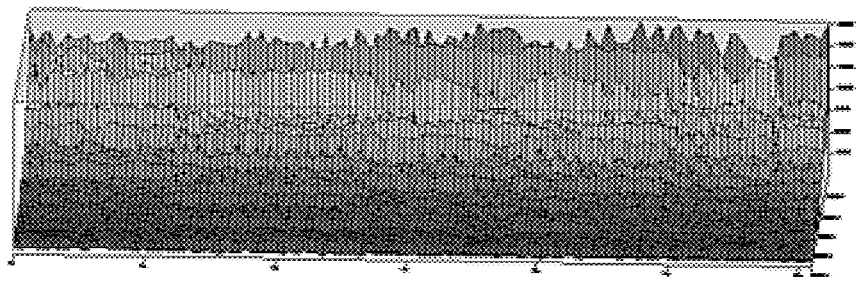
Sample 1 - Lavender (*lavandula*) whole plant sample - Normal Plant
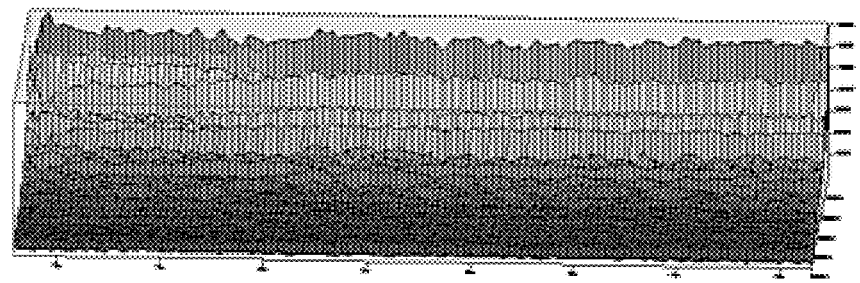
Sample 2 - Lavender (*lavandula*) whole plant sample - Abnormal Plant Figure 47
Quality testing of food products.
Aged Cheese Testing
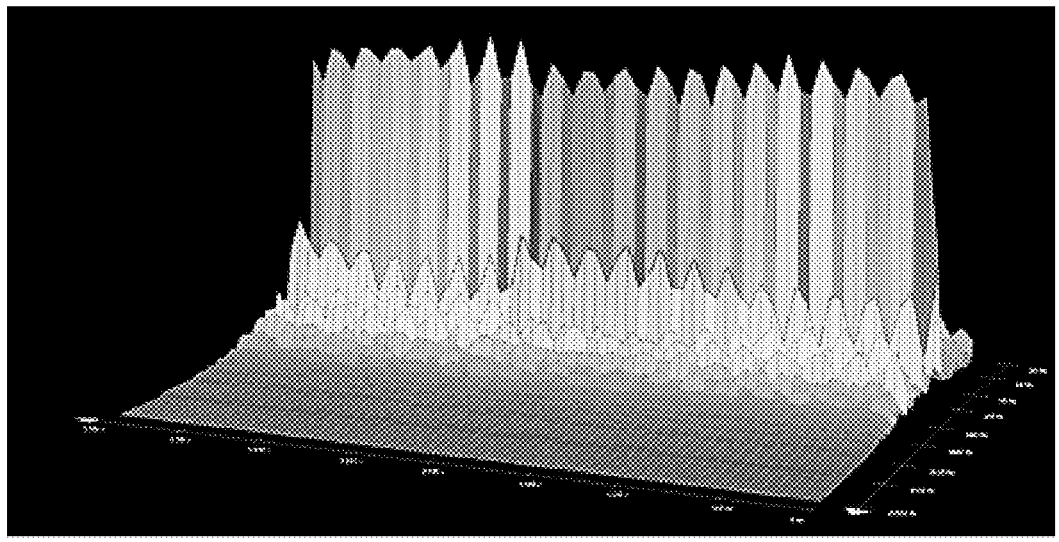
Cheese Sample 1 - Grana Padano 8 months.
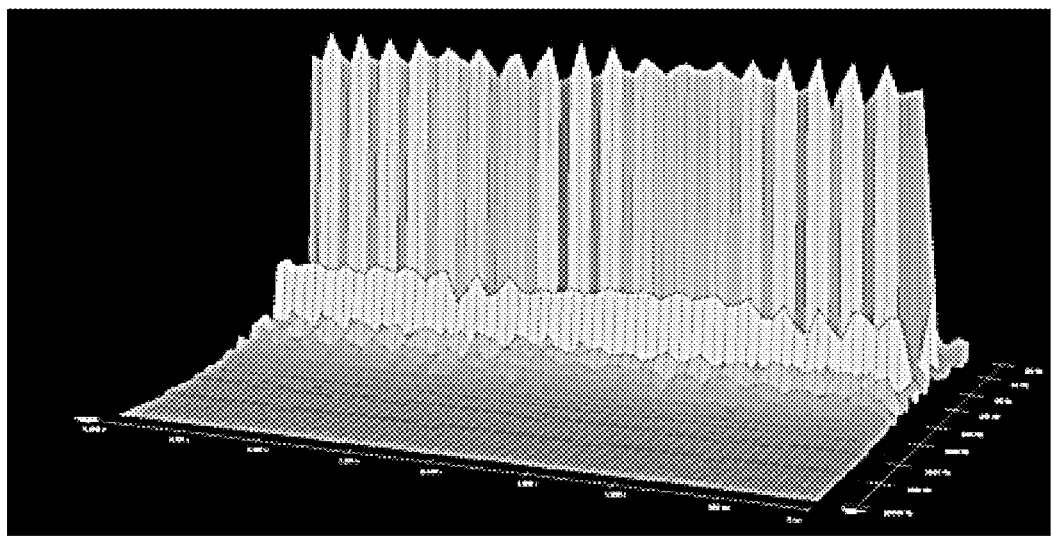
Cheese Sample 2 - Grana Padano 36 Months.

Figure 48
Quality testing of food additives.
Food Additive - Calcium Carbonate
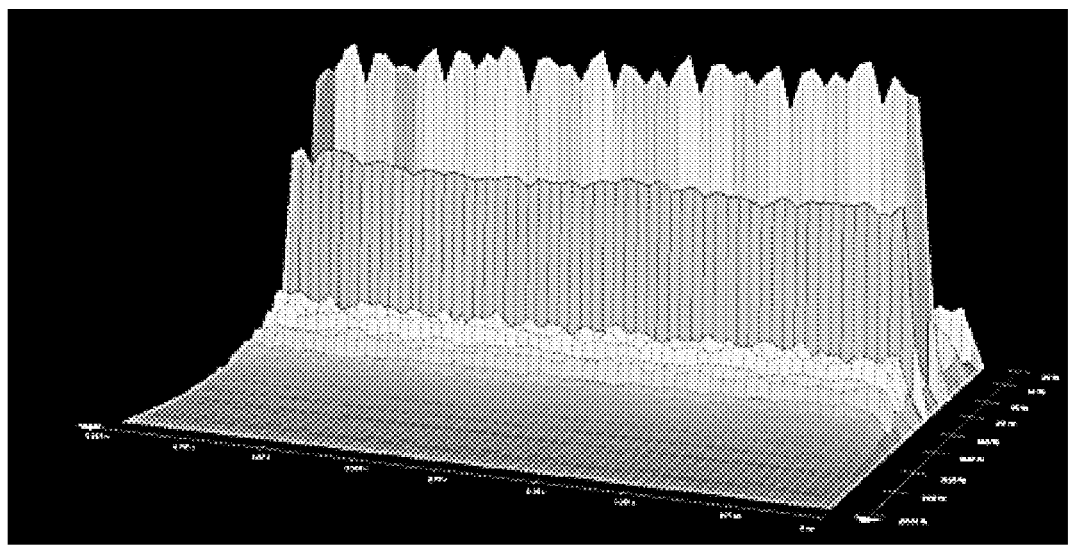
Sample 1 - Food Additives - Calcium Carbonate (Supplier 1 Italy)
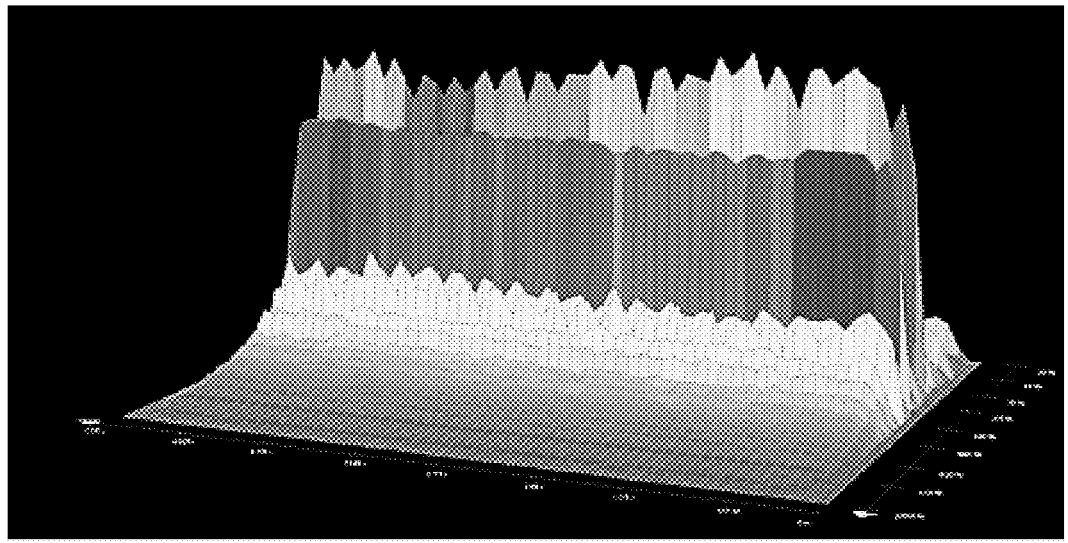
Sample 2 - Food Additives - Calcium Carbonate (Supplier 1 Germany)

Figure 49

The testing of a bee hive and the reaction of the hive to the presence of a mobile telephone on standby and during a series of calls.

Bee hive response.

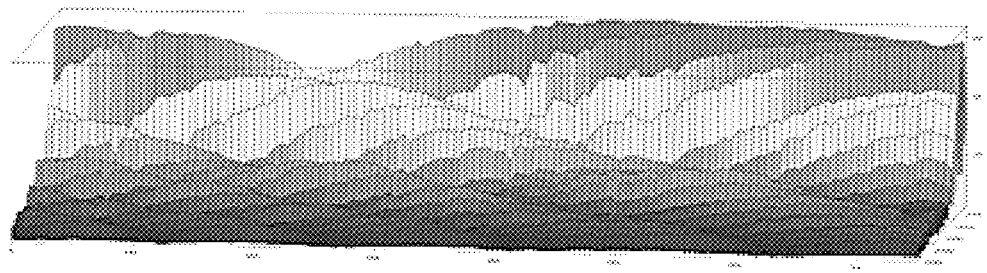

State 1 - Bioharmonic Signal of an undisturbed Bee Hive.

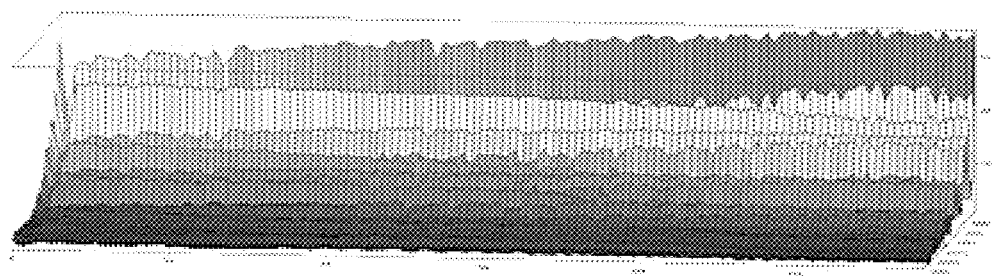

State 2 - Bioharmonic Signal of a Bee Hive - With mobile phone placed on top of hive.

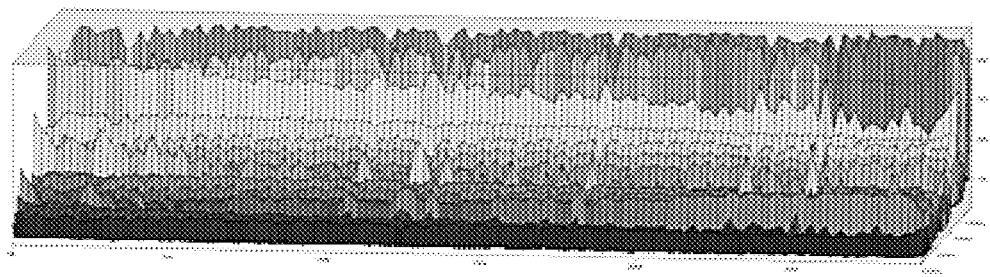

State 3 - Bioharmonic Signal of a Bee Hive - With mobile phone receiving calls and SMS messages.

Figure 50
The testing of a bee hive in its normal state and in a state of disturbance by tapping forcefully on the hive.
Bee hive response.
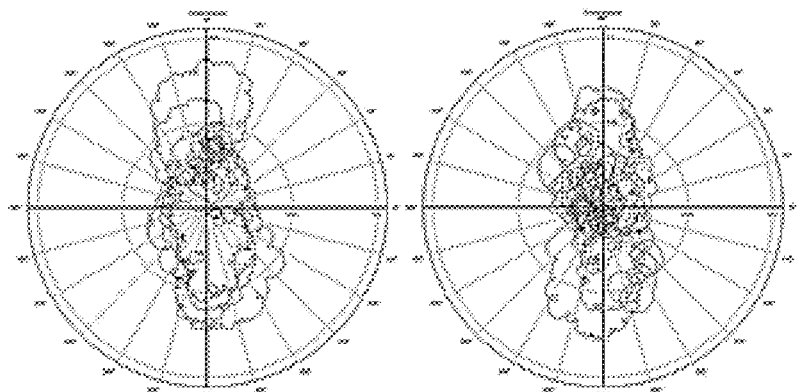
Sample 1 and 2 - Orbital phase chart of bee hive under normal conditions.
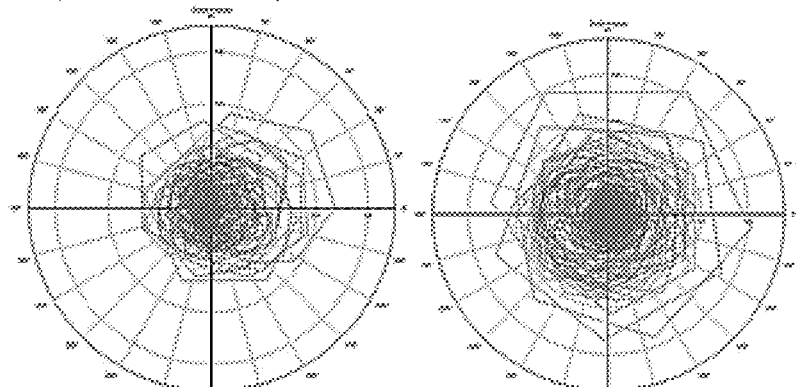
Sample 3 and 4 - Orbital phase chart of bee hive under stress conditions.
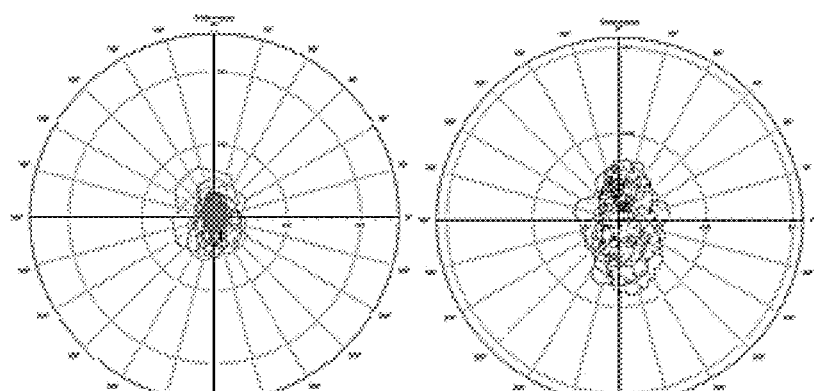
Sample 5 and 6 - Orbital phase chart of bee hive after stress condition returning to normal state.

Figure 51

Testing of sex differences in humans.

Influence on water sample of human male and female subjects inside a Faraday cage.

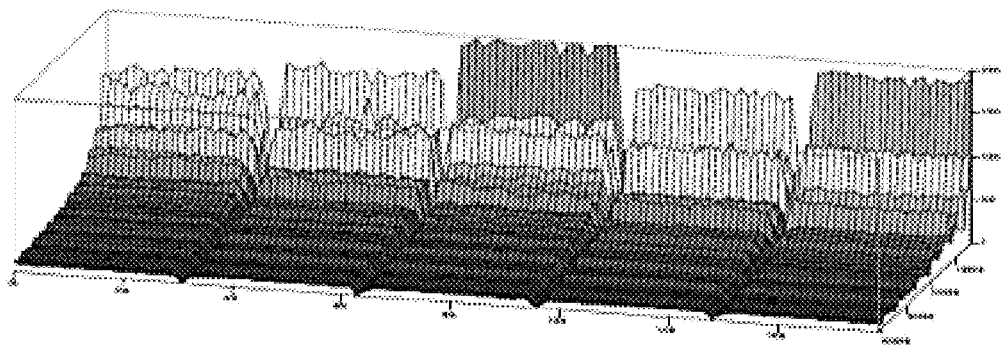

Sample 1 - Control sample; Sample 2 - Male 1; Sample 3 - Female 1; Sample 4 - Male 2; Sample 5 - Female 2.

Biocompatibility Testing

Influence of various liquids on the human bioharmonic field.

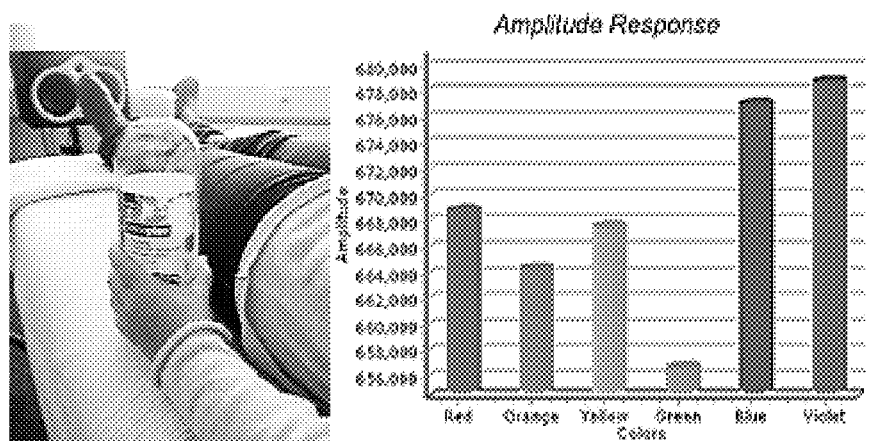

1. RED - Male Subject Reference; 2. ORANGE - In Contact With Water; 3. YELLOW - In Contact With White Wine; 4. GREEN - In Contact With Coke Zero; 5. BLUE - In Contact With Vinegar; 6. VIOLET - In Contact With Gasoline.

Figure 52
Testing the of presence and movement of female and male subjects.
Human bioharmonic field related to presence and movement.
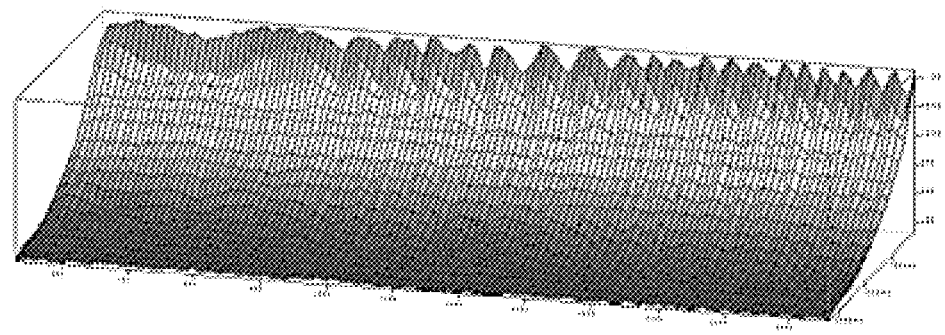
Subject 1 - Female approaching sensor electrode (antenna).
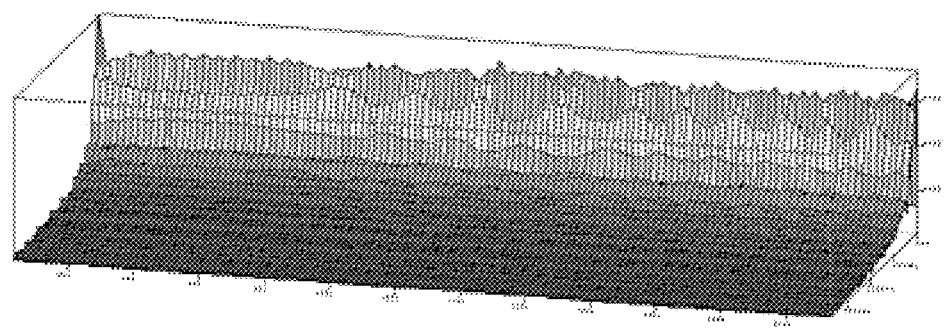
Subject 2 - Male approaching sensor electrode (antenna).

Figure 53
Testing the condition of human blood serum.
Human blood serum before and after physical activity.
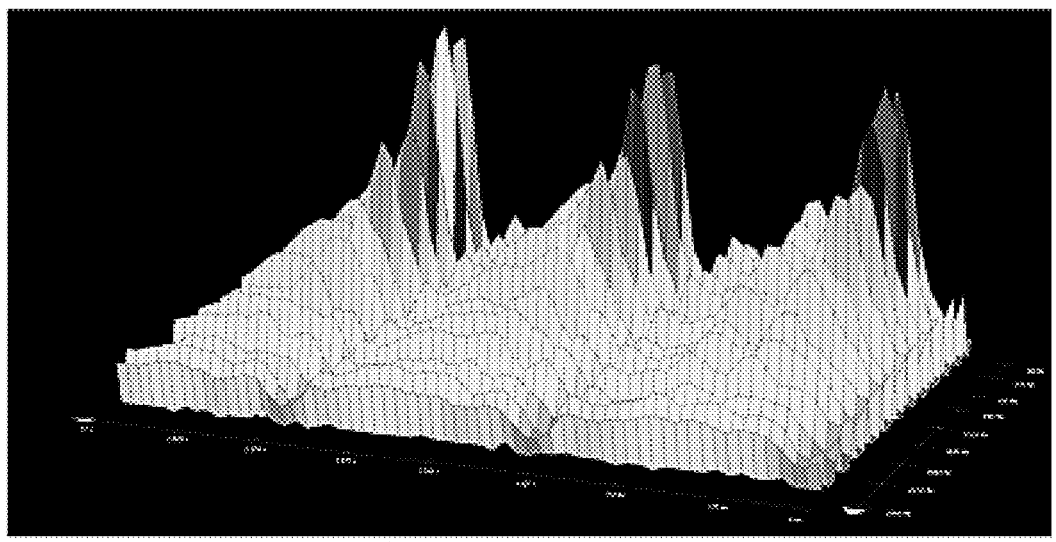
Surface Spectrum - Human Blood Serum - Before physical activity.
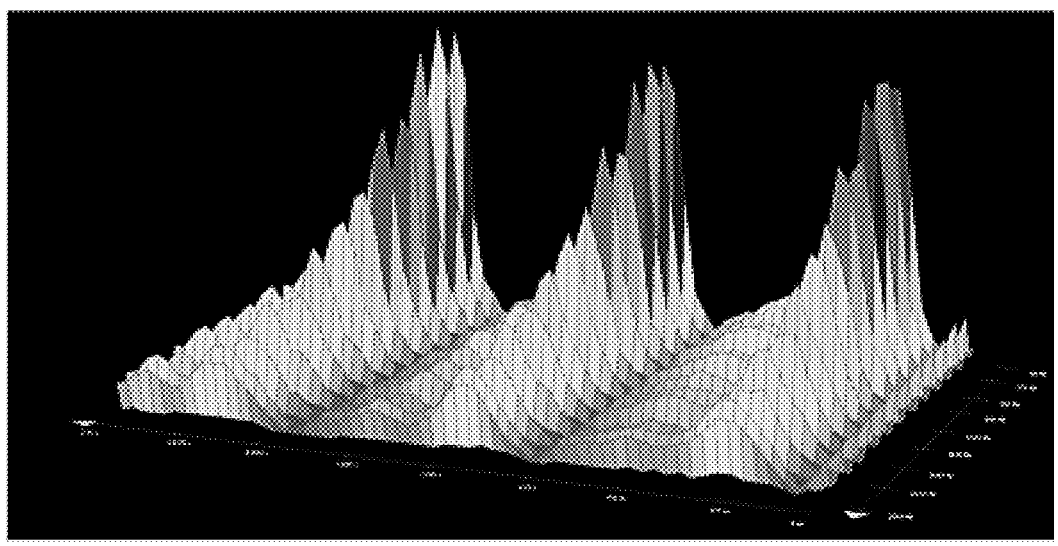
Surface Spectrum - Human Blood Serum - After physical activity.

Testing for pathological condition in human blood serum.

Human blood serum normal and three pathological conditions.

Surface Spectrum - Human Blood Serum - Sample 1 - Normal; Sample 2 - PSA elevated; Sample 3 - Cancer; Sample 4 - EVB + CMV.

Figure 55
Identification of unique bioharmonic signature in human tissues.
Bioharmonic signature of human skin cells.
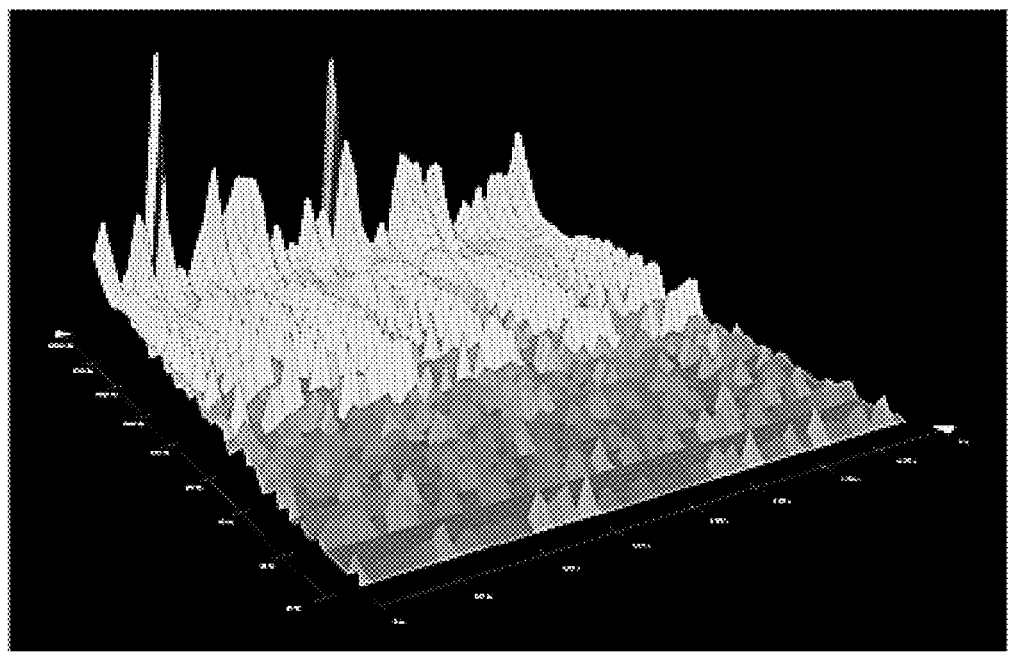
Sample 1 - Human adipocyte skin cell culture.
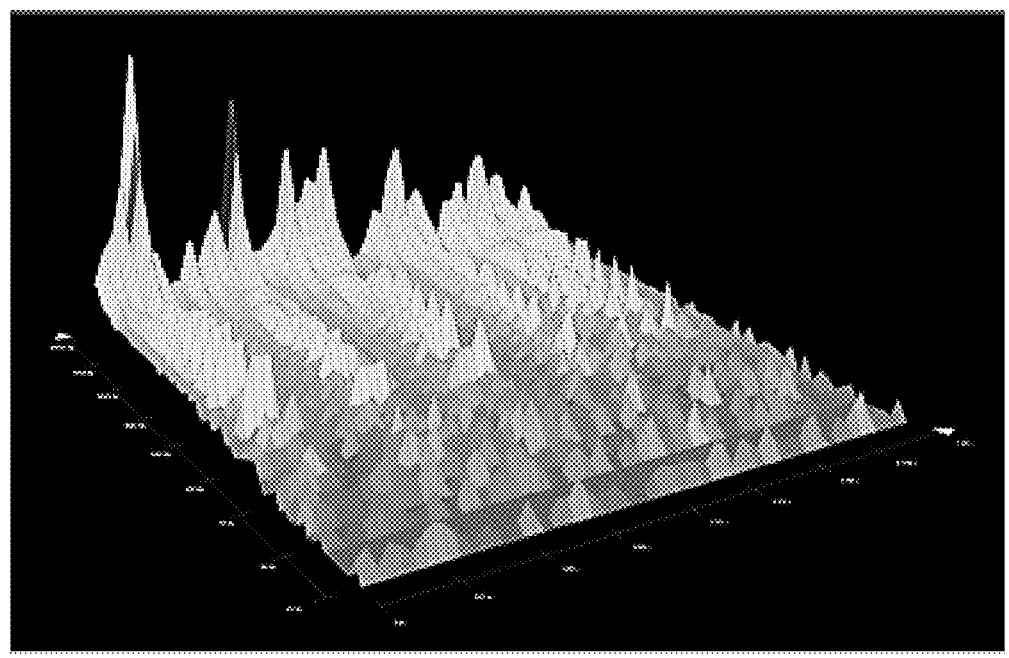
Sample 2 - Human adipocyte skin cell culture.

Figure 56
Identification of unique bioharmonic signature in human tissues.
Bioharmonic signature of human skin cells.
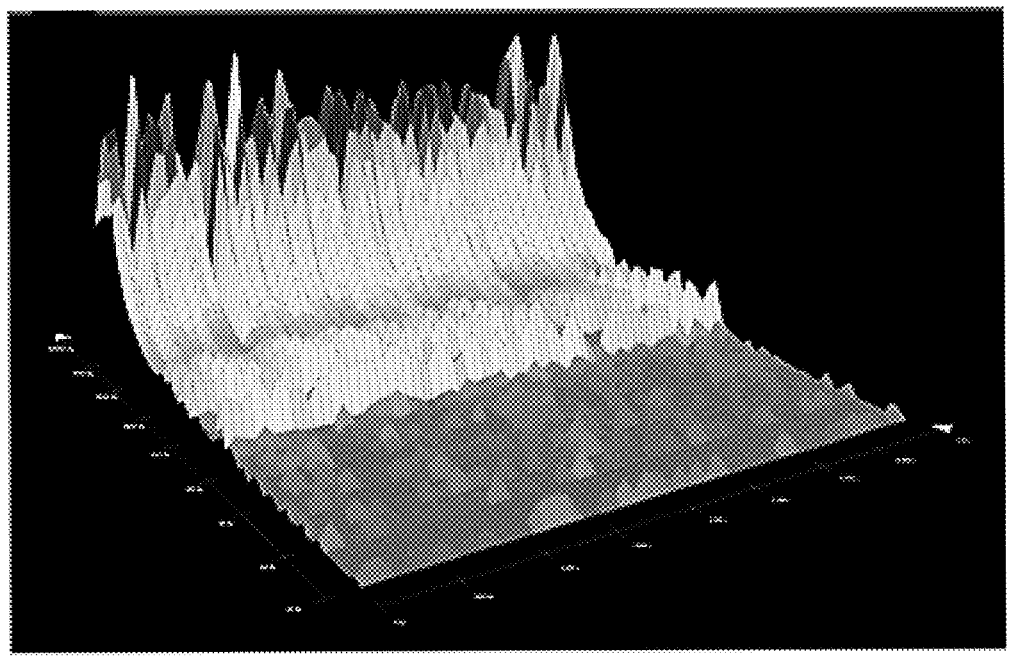
Sample 3 - Human fibroblast skin cell culture.
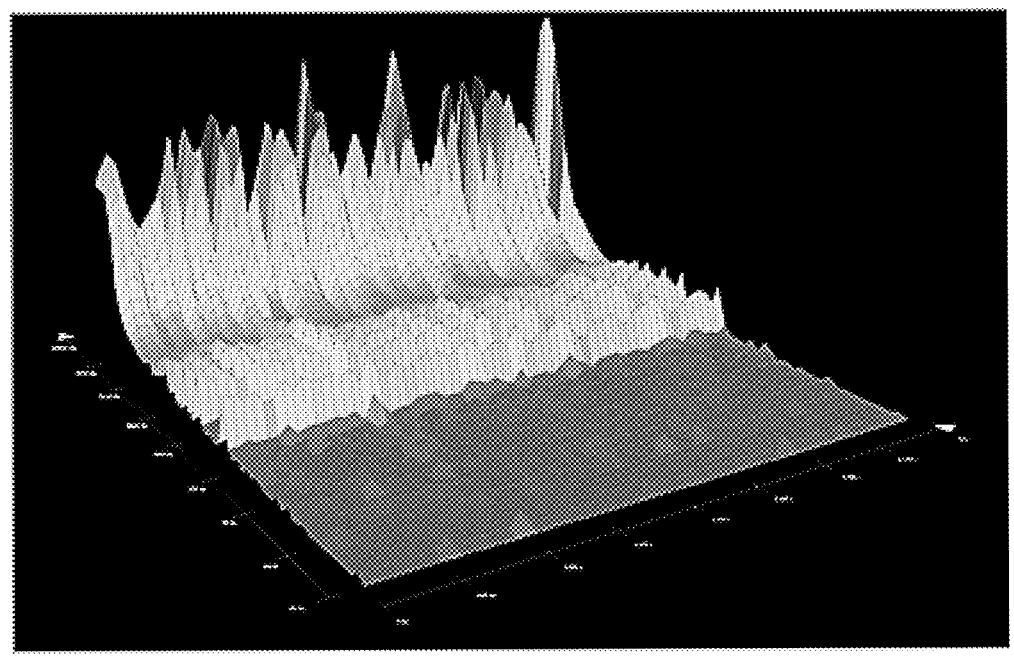
Sample 4 - Human fibroblast skin cell culture.

Figure 57
Identification of unique bioharmonic signature in human tissues.
Bioharmonic signature of human lung epithelial cells.
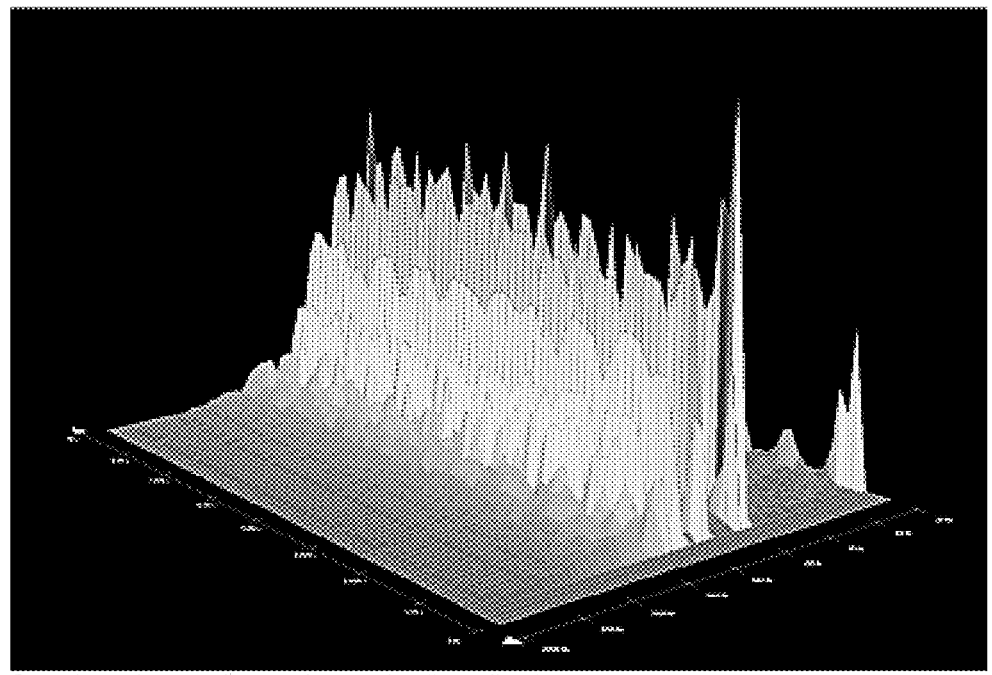
Sample 1 - Normal human lung epithelial cell culture.
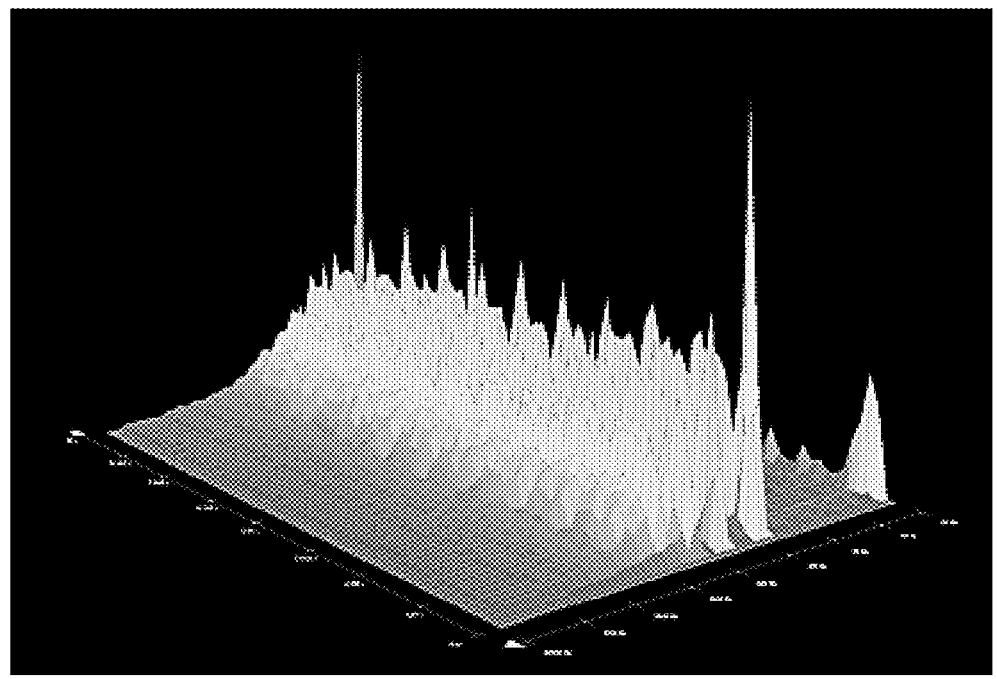
Sample 1 - Cancerous human lung epithelial cell culture.

Figure 58
Human bioharmonic field condition before and after naturopathic treatment.
Chinese acupuncture treatment.
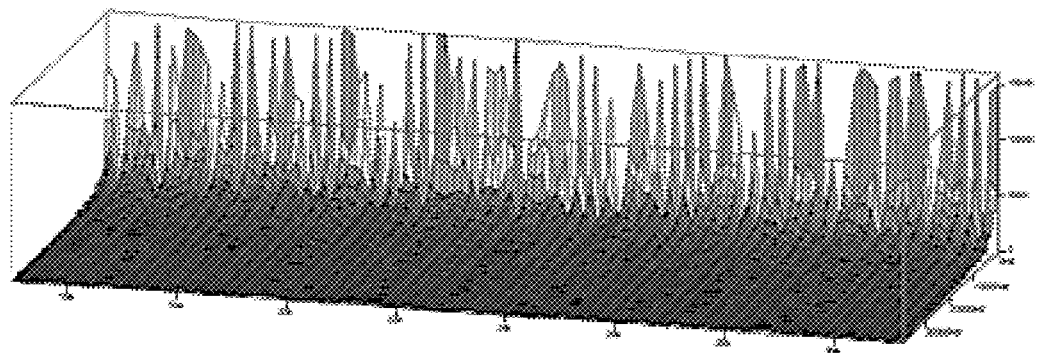
Human bioharmonic field before Chinese acupuncture treatment.
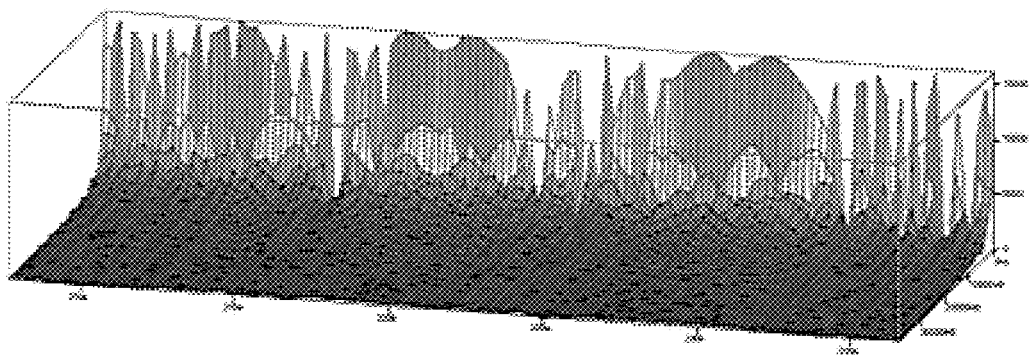
Human bioharmonic field after Chinese acupuncture treatment.

Human bioharmonic field condition before and after naturopathic treatment.

Sound treatment therapy.

Human bioharmonic field before and after sound treatment therapy.

Figure 60
Human bioharmonic field condition during psychological test questions.
Psychological stress testing.
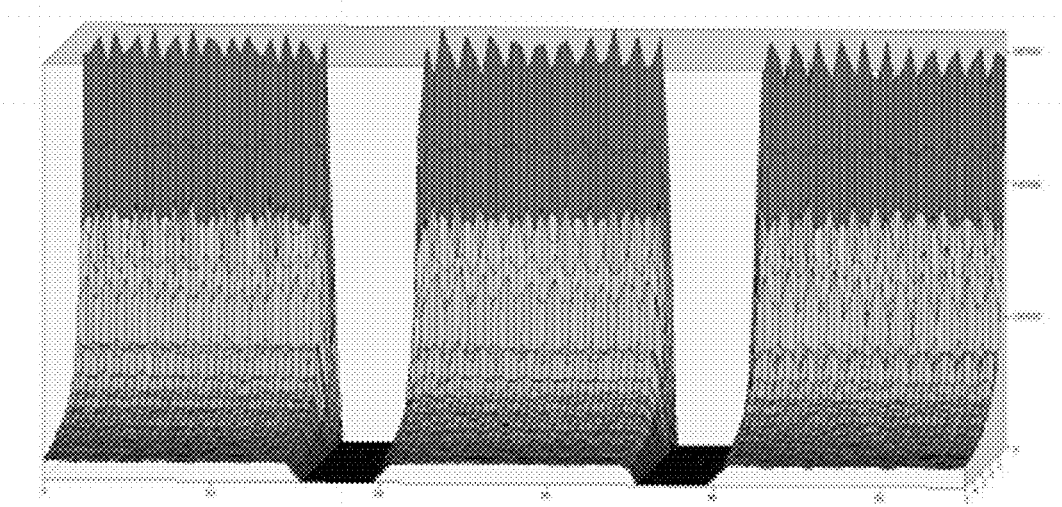
Sate 1 - Reference; State 2 - What is your name?; State 3 - Is it a nice day?
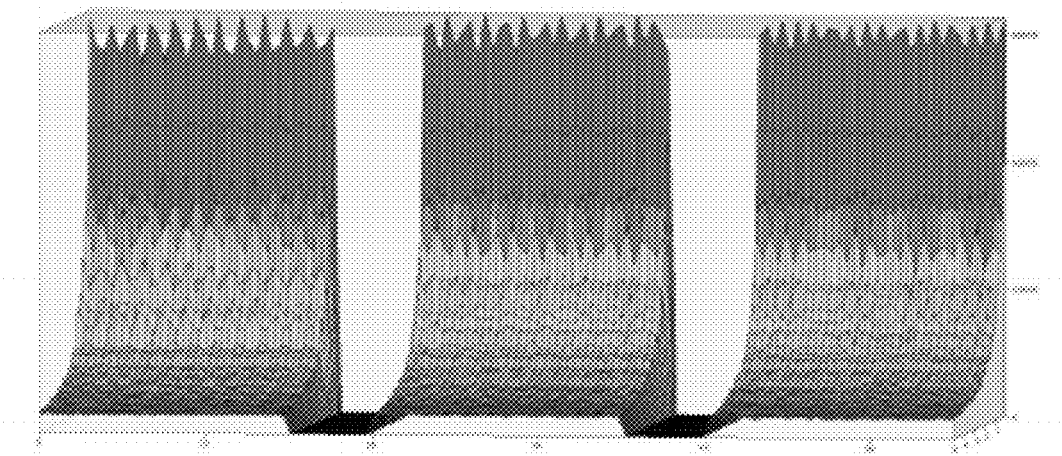
Sate 4 - Do you like sweets?; State 5 - Do you like spiders?; State 6 - Do you like snakes?

Figure 61
Testing for bioharmonic field differences in identical twins.
Identical twins - male.
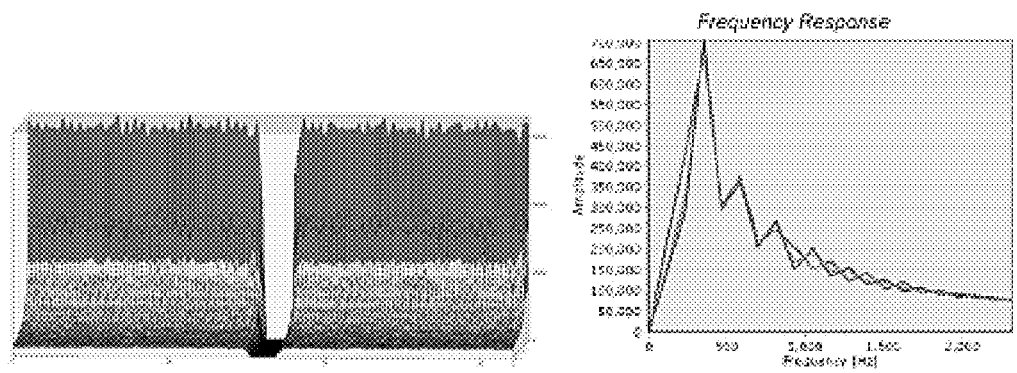
Surface spectrum recorded 20 minutes apart and frequency spectrum of six body zones of identical twin "Bob".
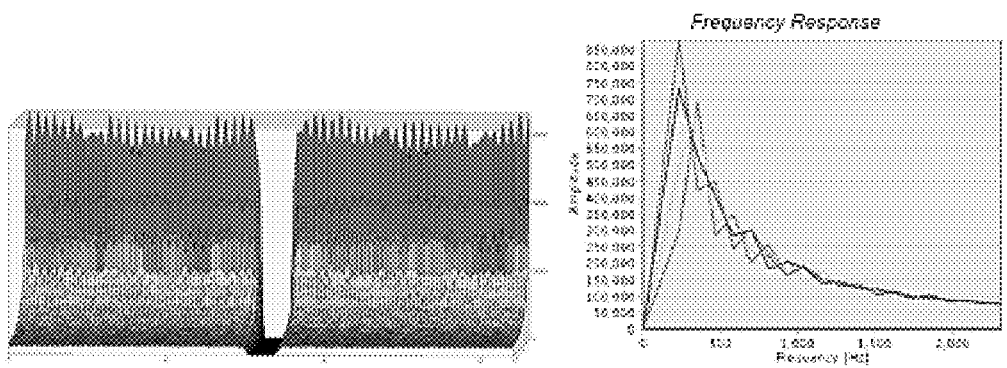
Surface spectrum recored 20 minutes apart and frequency spectrum of six body zones of identical twin "Charlie".

Figure 62
Testing for bioharmonic field differences in identical twins.
Identical twins - female.
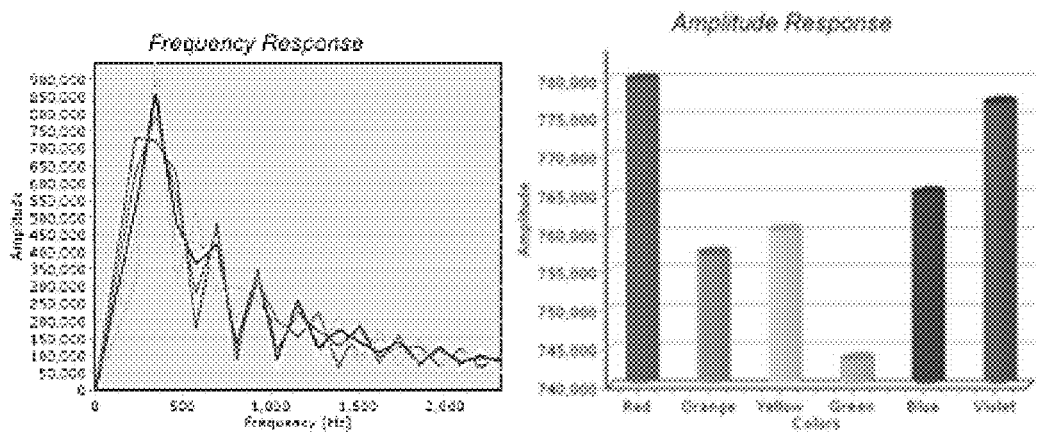
Frequency spectrum and average spectral power of six body zones of identical twin "Alice".
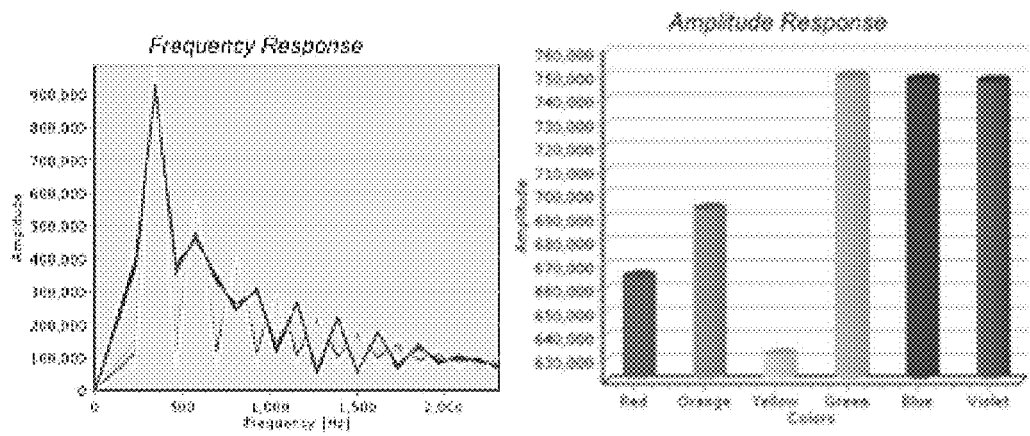
Frequency spectrum and average spectral power of six body zones of identical twin "Betty".

Ambrosia

Banana

SIGNAL CAPTURE METHOD AND APPARATUS FOR THE DETECTION OF LOW FREQUENCY ELECTRIC SIGNALS IN LIQUIDS AND BIOLOGICAL MATTER This application is the U.S. national phase of International Application No. PCT/IB2013/055513, filed 5 Jul. 2013, which designated the U.S. and claims priority to EP Application No. 12175457.6, filed 6 Jul. 2012, the entire contents of each of which are hereby incorporated by reference.

TECHNICAL FIELD

The present invention relates to a method and apparatus intended for the detection of low frequency electric waves that can be extracted from water, organic liquids and biological matter. This field phenomenon, that we here refer to here as a "bioharmonic", is an active frequency, or harmonically related series of frequencies, that are a result of a dynamic interplay of natural processes including physical, chemical and electromagnetic interactions.

BACKGROUND CONCEPTS

Definitions

The designation bioharmonic signal is used to identify a novel wave phenomenon, or in other words, a low frequency electrical waveform that is related to the state and or behavior of a biological system. Wherein the origin of the term bio is used as a short form for the term biology or biological, relating to the properties of living systems, and the term harmonic is used in relation to individual frequency components of a complex waveform.

The term biological system is used to signify any living or biological organism or system such as a protein, cell, organ, plant, animal, or human.

The term bioactive matter is used to signify any matter or material that is derived from or is a component to a biological system.

The term bioharmonic detection system is used to signify a unique electronic device that is capable of detecting low frequency electric field changes in a biological system or in bioactive matter.

Vibration and the Electromagnetic Spectrum

A spectrum is a condition that is not limited to a specific set of values but can vary infinitely within a continuum. The term refers to a plot of intensity or power as a function of frequency or wavelength, also known as a spectral density, and now applies to any signal that can be measured or decomposed along a continuous variable. Some typical examples include: the energy in electron spectroscopy, the mass to charge ratio in mass spectrometry, or the harmonic content of sound waves. The term spectrum is also used to refer to a graphical representation of the frequency components that make up a complex waveform.

Electromagnetic Fields

The electromagnetic field is defined as the field produced by moving charges. Electromagnetic radiation (EM radiation or EMR) is a form of energy emitted and absorbed by charged particles, which exhibits wave-like behavior as it travels through a medium (i.e. space). At different frequency bands we have unique manifestations of energy:

At the upper end of the electromagnetic spectrum, the gamma range ($10^{-12}$ m), we have the vibrations of atomic nuclei. In the x-ray band ($10^{-10}$ nm) we find the vibrations of atoms. In the ultra-violet range ($10^{-8}$ nm), the vibrations of molecules and ions. In the visible range ($0.5 \times 10^{-6}$) energy manifests as light.

An electron in an excited molecule or atom that descends to a lower energy level emits a photon of light equal to the energy difference. Since the energy levels of electrons in atoms are discrete, each element and each molecule emits and absorbs its own characteristic frequencies.

In the infra-red band ($10^{-5}$) energy manifests as heat. Lower still in the gigahertz and microwave band ($10^{-2}$) we have, what is commonly misquoted as <<electromagnetic radiation>> of communication systems, radar, mobile phones, wireless networks, etc., lower still along the electromagnetic frequency spectrum, we find radio waves.

The region of vibrational frequencies lower than the radio band, less than 500 kHz, we can call the <<extended audio frequency range>>. In this region we have the ultrasonic band (frequencies greater than 20 kHz), audible sound (16 Hz-20 kHz), and infra-sound (less than 16 Hz). Over this range, energy manifests as a mechanical force, whereby it moves the molecular and atomic position of matter in space without disturbing it's structure. The extended audio frequency range consists of a wide bandwidth which includes the vibrations generated by mechanical action, tectonic movement, weather and ocean currents, the movement of planets, stars and galaxies, and biological systems (i.e. speech, birdsong, animal sounds, heartbeat, respiration, etc.).

The lower frequency band of the electromagnetic spectrum, less than 500 kHz, can generate a field of physical or mechanical influence on matter, which for example may be observed by moon's effects on ocean tides caused by gravitational waves, and ultrasound can be applied to modify the mechanical properties of cells used in biological research or to eliminate tartar buildup on tooth enamel.

The common approach in defining phenomena across the electromagnetic spectrum is based in principle by our interest in a specific application. We are more or less tied to a particular range of the energy spectrum, and the perception we have in our frame of reference regarding that interest is somehow limited to this particular range. Such particular range is for example the electromagnetic spectrum as applied to communications systems, the visible light band, the X-ray band, the gamma range, the sound spectrum, etc. It is very rare to find references related to interactions that involve multiple ranges of the electromagnetic spectrum.

FIG. 1. The Electromagnetic Spectrum

Waves, Oscillations and Vibrations

Waves, also known as oscillations or vibrations, are disturbances that travel through space and matter, accompanied by a transfer of energy. Waves are prevalent throughout the natural world and their frequency bandwidth extends across the entire electromagnetic spectrum encompassing all know phenomena ranging from the interactions of atoms and molecules to visible light, heat, radio waves, sound, mechanical vibrations, seismic waves to the gravitational effects of planetary bodies. While a single definition of waves or vibrations is not straightforward, it is generally understood that they are caused by the movement of potential or energy, originating from or propagating through an object or system, and refers to the transport of disturbances over time and space.

In physics, a wave is a disturbance (an oscillation) that travels through space in time, accompanied by the transfer of energy. Waves travel and the wave motion transfers energy from one point to another, often with no permanent displacement of the particles of the medium—in other words, with little or no associated mass transport. They consist, instead, of oscillations or vibrations around generally fixed locations. An example is a cork on rippling water that is moving up and down, staying in about the same place while the wave itself moves onwards.

An oscillation is a repetitive variation, typically in time, of some measure about a central value (often a point of equilibrium) or between two or more different states. Familiar examples include a swinging pendulum and AC power. The term vibration is sometimes used more narrowly to mean a mechanical oscillation but sometimes is used to be synonymous with <<oscillation>>. Oscillations occur not only in physical systems but also in biological systems and in human society.

One type of wave is a mechanical wave, which propagates through a medium in which the substance of this medium is deformed. The deformation reverses itself owing to restoring forces resulting from its deformation. For example, sound waves propagate via air molecules bumping into their neighbors. This transfers some energy to these neighbors, which will cause a cascade of collisions between neighboring molecules. When air molecules collide with their neighbors, they also bounce away from them (restoring force). This keeps the molecules from continuing to travel in the direction of the wave.

Another type of wave can travel through a vacuum, e.g. electromagnetic radiation (including visible light, ultraviolet radiation, infrared radiation, gamma rays, X-rays, and radio waves). This type of wave consists of periodic oscillations in electrical and magnetic fields.

A main distinction can be made between transverse and longitudinal waves. Transverse waves occur when a disturbance creates oscillations perpendicular (at right angles) to the propagation (the direction of energy transfer). Longitudinal waves occur when the oscillations are parallel to the direction of propagation. Waves are described by a wave equations which set out how the disturbances proceeds over time. The mathematical forms of these equation vary depending on the type of wave.

General Features of Waves

A single, all-encompassing definition for the term wave is not straightforward. A vibration can be defined as a back-and-forth motion around a reference value. However, a vibration is not necessarily a wave. An attempt to define the necessary and sufficient characteristics that qualify a phenomenon to be called a wave remains unclear.

The term wave is often intuitively understood as referring to a transport of spatial disturbances that are generally not accompanied by a motion of the medium occupying this space as a whole. In a wave, the energy of a vibration is moving away from the source in the form of a disturbance within the surrounding medium. However, this notion is problematic for a standing wave (for example, a wave on a string), where energy is moving in both directions equally, or for electromagnetic/light waves in a vacuum, where the concept of medium does not apply and the inherent interaction of its component is the main reason of its motion and broadcasting. There are water waves on the ocean surface; light waves emitted by the Sun; microwaves used in microwave ovens; radio waves broadcast by radio stations; and sound waves generated by radio receivers, telephone handsets and living creatures (as voices).

It may appear that the description of waves is closely related to their physical origin for each specific instance of a wave process. For example, acoustics is distinguished from optics in that sound waves are related to a mechanical rather than an electromagnetic wave transfer caused by vibration. Concepts such as mass, momentum, inertia, or elasticity, become therefore crucial in describing acoustic (as distinct from optic) wave processes. This difference in origin introduces certain wave characteristics particular to the properties of the medium involved. For example, in the case of air: vortices, radiation pressure, shock waves etc.; in the case of solids: Rayleigh waves, dispersion etc.; and so on.

Other properties which are usually described in an origin-specific manner, may be generalized to all waves. For such reasons, wave theory represents a particular branch of physics that is concerned with the properties of wave processes independently from their physical origin. For example, based on the mechanical origin of acoustic waves, a moving disturbance in space-time can exist if and only if the medium involved is neither infinitely stiff nor infinitely pliable. If all the parts making up a medium were rigidly bound, then they would all vibrate as one, with no delay in the transmission of the vibration and therefore no wave motion. This is impossible because it would violate general relativity. On the other hand, if all the parts were independent, then there would not be any transmission of the vibration and again, no wave motion. Although the above statements are meaningless in the case of waves that do not require a medium, they reveal a characteristic that is relevant to all waves regardless of origin: within a wave, the phase of a vibration (that is, its position within the vibration cycle) is different for adjacent points in space because the vibration reaches these points at different times.

Similarly, wave processes revealed from the study of waves other than sound waves can be significant to the understanding of sound phenomena. A relevant example is Thomas Young's principle of interference (Young, 1802, in Hunt 1992, p. 132). This principle was first introduced in Young's study of light and, within some specific contexts (for example, scattering of sound by sound), is still a researched area in the study of sound.

Waveform means the shape and form of a signal such as a wave moving in a physical medium or an abstract representation. In many cases the medium through which the wave propagates does not permit a direct visual image of the form. In these cases, the term 'waveform' refers to the shape of a graph of the varying quantity against an axis of time or distance. By extension, the term 'waveform' also describes the shape of the visual graph of any varying quantity over time.

Examples of Waveforms

Sine wave: $\sin(2\pi t)$. The amplitude of the waveform follows a trigonometric sine function with respect to time. The sine wave or sinusoid is a mathematical function that describes a smooth repetitive oscillation. Its most basic form as a function of time (t) is:

FIG. 4 where: A, the amplitude, is the peak deviation of the function from its center position.

$\omega$, the angular frequency, specifies how many oscillations occur in a unit time interval, in radians per second $\phi$, the phase, specifies where in its cycle the oscillation begins at t=0. When the phase is non-zero, the entire waveform appears to be shifted in time by the amount $\phi/\omega$ seconds. A negative value represents a delay, and a positive value represents an advance.

The sine wave is important in physics because it retains its wave shape when added to another sine wave of the same frequency and arbitrary phase and magnitude. It is the only periodic waveform that has this property. This property leads to its importance in Fourier analysis and makes it acoustically unique.

Square wave: saw(t)−saw (t−duty). This waveform is commonly used to represent digital information. A square wave of constant period contains odd harmonics that fall off at −6 dB/octave.

Triangle wave: (t−2 floor ((t+1)/2)) (−1)floor ((t+1)/2). It contains odd harmonics that fall off at −12 dB/octave.

Sawtooth wave: 2 (t−floor(t))−1. This looks like the teeth of a saw. Found often in time bases for display scanning. It is used as the starting point for subtractive synthesis, as a saw tooth wave of constant period contains odd and even harmonics that fall off at −6 dB/octave.

Other waveforms are often called composite waveforms and can often be described as a combination of a number of sinusoidal waves or other basis functions added together.

Harmonics

A harmonic of a wave is a component frequency of the signal that is an integer multiple of the fundamental frequency. Complex waveforms with a base vibration frequency contain a series of harmonics and sub-harmonics. The harmonics of a signal as defined as related vibrations that are integer multiples of the fundamental oscillation. Theoretically, the harmonic series extends to infinity in both the upper frequency range, multiplying the fundamental frequency for the upper partials, and dividing the fundamental frequency for the lower partials which are called sub-harmonics. We can illustrate this as follows for a fundamental frequency of 440 Hz:

Upper Harmonics (in Hz): 880, 1320, 1760, 2200, etc.
Fundamental Frequency: 440 Hz
Lower Harmonics (sub-harmonics): 220, 110, 55, 27.5, etc.

The fundamental frequency is the reciprocal of the period of a periodic function.

It is thought that any phenomena occurring at one band of the electromagnetic spectrum may have influences across multiple other ranges (i.e. the heating effects on cells via electromagnetic radiation; the creation of resonant low frequency standing waves in acoustic environments caused by sound vibrations).

Harmonics

Any complex waveform an be described as a vibration composed of a series of simple periodic waves (sine waves) each with its own frequency, amplitude, and phase. A harmonic (or a harmonic partial) is any of a set of vibrations that are whole number multiples of a common fundamental frequency and is any of the sine wave components by which a complex waveform is described. Inharmonicity is a measure of the deviation of a partial from the closest ideal harmonic.

A harmonic of a wave is a frequency component of the signal that is an integer multiple of the fundamental frequency. For example, if the fundamental frequency is f, the harmonics have frequencies 2f, 3f, 4f, etc. The harmonics have the property that they are all periodic at the fundamental frequency; therefore the sum of harmonics is also periodic at that frequency. Harmonic frequencies are equally spaced by the width of the fundamental frequency and can be found by repeatedly adding that frequency. For example, if the fundamental frequency is 25 Hz, the frequencies of the harmonics are: 50 Hz, 75 Hz, 100 Hz etc.

The Fourier series describes the decomposition of periodic waveforms, such that any periodic waveform can be formed by the sum of a (possibly infinite) set of fundamental and harmonic components. Finite-energy and non-periodic waveforms can also be analyzed into sinusoids by the Fourier transform.

Waveforms that contain a regular and ordered harmonic content are said to be coherent, while waveforms with an unordered harmonic content are said to be incoherent or chaotic.

The harmonic content of complex waveforms is equivalent to information.

Emission Spectrum

The emission spectrum of a chemical element or chemical compound is the spectrum of frequencies of electromagnetic radiation emitted by the element's atoms or the compound's molecules when they are returned to a lower energy state. The emission spectrum of each element is unique, thus spectroscopy can be used to identify the various elements in matter of unknown composition. Similarly, the emission spectra of molecules can be used in chemical analysis of substances.

Emission is a process by which a higher energy quantum mechanical state of a particle becomes converted to a lower one through the emission of a photon, resulting in the production of light. The frequency of light emitted is a function of the energy of the transition. The energy states of the transitions can lead to emissions over a very large range of frequencies. For example: the coupling of electronic states in atoms and molecules produces visible light (a phenomenon called fluorescence or phosphorescence); nuclear shell transitions can emit high energy gamma rays; nuclear spin transitions emit low energy radio waves. Precise measurements at many wavelengths allow the identification of a substance via emission spectroscopy.

Absorption Spectrum

The absorption spectrum is a spectroscopic technique that measures the interaction between electromagnetic radiation and a sample. As a sample is exposed to a radiating field, the intensity of energy (photon) absorption will vary as a function of frequency or wavelength. A material's absorption spectrum is the fraction of incident radiation absorbed by the material over a range of frequencies.

The frequencies where absorption lines occur, as well as their relative intensities, primarily depend on the electronic and atomic structure of the molecule. The frequencies will also depend on the interactions between molecules in the sample, the crystal structure in solids, and on several environmental factors such as temperature, pressure, and the presence of electromagnetic fields. The lines will have a width and shape that are primarily determined by the spectral density or the density of states of the system.

Absorption lines are typically classified by the nature of the quantum mechanical change induced in the molecule or atom. Rotational lines, for instance, occur when the rotational state of a molecule is changed. Rotational lines are typically found in the microwave spectral region. Vibrational lines correspond to changes in the vibrational state of the molecule and are typically found in the infrared region. Electronic lines correspond to a change in the electronic state of an atom or molecule and are typically found in the visible and ultraviolet region. X-ray absorptions are associated with the excitation of inner shell electrons in atoms. These changes can also be combined (e.g. rotation-vibration transitions), leading to new absorption lines at the combined energy of the two changes.

Electric Charge

Electric charge is a physical property of matter that causes it to experience a force when it is near other electrically charged matter. Electric charge comes in two types, called positive and the other negative. Two positively charged substances, or objects, experience a mutual repulsive force, as do two negatively charged objects. Positively charged objects and negatively charged objects experience an attractive force.

The electric charge is a fundamental conserved property of some subatomic particles, which determines their electromagnetic interaction. Electrically charged matter is influenced by, and produces, electromagnetic fields. The interaction between a moving charge and an electromagnetic field is the source of the electromagnetic force, which is one of the four fundamental forces.

Charge is the fundamental property of forms of matter that exhibit electrostatic attraction or repulsion in the presence of other matter. Electric charge is a characteristic property of many subatomic particles. The charges of free-standing particles are integer multiples of the elementary charge e, we say that electric charge is quantized, that is, it comes in multiples of individual small units called the elementary charge, e, (approximately equal to $1.602 \times 10^{-19}$ coulombs). The proton has a charge of e, and the electron has a charge of –e. The SI unit of electric charge is the coulomb (C).

Coulomb's law quantifies the electrostatic force between two particles by asserting that the force is proportional to the product of their charges, and inversely proportional to the square of the distance between them.

The electric charge of a macroscopic object is the sum of the electric charges of the particles that make it up. This charge is often small, because matter is made of atoms, and atoms typically have equal numbers of protons and electrons, in which case their charges cancel out, yielding a net charge of zero, making the atom and thus the object electrically neutral.

Atoms and Ions

An ion is an atom (or group of atoms) that has lost one or more electrons, giving it a net positive charge (cation), or that has gained one or more electrons, giving it a net negative charge (anion). Monatomic ions are formed from single atoms, while polyatomic ions are formed from two or more atoms that have been bonded together, in each case yielding an ion with a positive or negative net charge.

During the formation of macroscopic objects, usually the constituent atoms and ions will combine in such a manner that they form structures composed of neutral ionic compounds electrically bound to neutral atoms. Thus macroscopic objects tend toward being neutral overall, but macroscopic objects are rarely perfectly net neutral.

There are times when macroscopic objects contain ions distributed throughout the material, rigidly bound in place, giving an overall net positive or negative charge to the object. Macroscopic objects made of conductive elements, can take on or give off electrons, and then maintain a net negative or positive charge indefinitely. When the net electric charge of an object is non-zero and motionless, the phenomenon is known as static electricity.

Non-conductive materials can be charged to a significant degree, either positively or negatively. Charges can be taken from one material and moved to another material, leaving an opposite charge of the same magnitude behind. The law of conservation of charge always applies, giving the object from which a negative charge has been taken a positive charge of the same magnitude, and vice-versa.

Even when an object's net charge is zero, charge can be distributed non-uniformly in the object (e.g., due to an external electromagnetic field, or bound polar molecules). In such cases the object is said to be polarized. The charge due to polarization is known as bound charge, while charge on an object produced by electrons gained or lost from outside the object is called free charge. The motion of electrons in conductive metals in a specific direction is known as electric current.

Molecules, Charge and Chemical Reactions

A molecule is an electrically neutral group of two or more atoms held together by covalent chemical bonds. Molecules are distinguished from ions by their lack of electrical charge, however, in quantum physics, organic chemistry, and biochemistry, the term molecule is also applied to polyatomic ions. A molecule may consist of atoms of a single chemical element, as with oxygen (O2), or of different elements, as with water (H2O). Molecules as components of matter are common in organic substances and are widely discussed in the field of biochemistry. In molecular sciences, a molecule consists of a stable system (bound state) comprising two or more atoms, polyatomic ions may be thought of as electrically charged molecules. The term unstable molecule is used for very reactive species, i.e., short-lived assemblies (resonances) of electrons and nuclei, such as radicals, molecular ions, Rydberg molecules, transition states, van der Waals complexes, or systems of colliding atoms as in Bose-Einstein condensate.

Ions are atoms or molecules in which the total number of electrons is not equal to the total number of protons, giving them a net positive or negative electrical charge. An anion (−) is an ion with more electrons than protons, giving it a net negative charge. A cation (+) is an ion with fewer electrons than protons, giving it a positive charge. Since the charge on a proton is equal in magnitude to the charge on an electron, the net charge on an ion is equal to the number of protons in the ion minus the number of electrons.

We can illustrate this electrical force phenomena if we take two materials, for example, which are made of atoms, and subject them to an activating force (i.e. water, heat, chemical compound, etc.) and cause the release of the <<activation energy>>, the energy required for a chemical reaction, or in biological systems the <<action potential>> which are potentials generated by voltage-gated ion channels embedded in a cell's plasma membrane. The activating force begins a process whereby, on an atomic level, the transfer of electrical charges between the substances ensues. It is commonly known that electrical charges either attract or repulse among themselves depending on them being positive or negative. Once this process is activated and sustained, the flow of energy is moved from one substance to another. When a sufficient amount of energy is displaced (i.e. electrons or protons), we have a transformation of matter: this is what is called a chemical reaction. The wave-like effects of these transformations in complex systems, and in turn their harmonic frequency components may spread across multiple ranges of the electromagnetic spectrum.

Living Systems

Life is a characteristic that distinguishes objects that have signaling and self-sustaining processes from those that do not, either because such functions have ceased (death), or else because they lack such functions and are classified as inanimate. Defining life is difficult because life is a process, not a pure substance.

Any contiguous living system is called an organism. These animate entities undergo metabolism, maintain homeostasis, possess a capacity to grow, respond to stimuli, reproduce and, through natural selection, adapt to their environment in successive generations. More complex living organisms can communicate through various means.

Biological definitions of life are generally based upon chemical systems. From the perspective of biophysics, living processes can be viewed as a delay of the spontaneous diffusion or dispersion of the internal energy of biological molecules towards more potential microstates. Living systems are a member of the class of phenomena that are open or continuous and able to decrease their internal entropy at the expense of substances or free energy taken in from the environment and subsequently rejected in a degraded form. It can also be stated that living beings are thermodynamic systems that have an organized molecular structure. Hence, life is a self-sustained chemical system (matter) that can reproduce itself and evolve as survival dictates.

It is thought that the process by which atoms and molecules are organized in living systems involves some sort of electrical or force phenomena that is linked with this process.

All biological systems and living organisms in turn, rely on a specific manner of physical organization of essentially inert or non-living material. The difference between <<living>> systems and <<non-living>> systems has to do with the specific spatial and temporal organization of essentially inanimate atoms and molecules that are the building blocks of biological matter. In biological systems, we generally find the presence of macro-molecules whose size and complexity are many orders of magnitude larger than the molecules of inanimate matter.

While it has been scientifically established that all biological systems contain DNA and RNA macro-molecules, at the same time, it cannot be affirmed that the source of life is found in this integrant. Even in the most advanced genetic laboratories, rather than being able to make living matter from the basic inanimate constituents, scientists are required to work with biological material which is already alive.

The fundamental underlying process by which the atoms and molecules are organized in biological systems is of yet largely unknown. In other words, it appears impossible to determine the fundamental mechanisms related to the organization of biological systems when applying standard concepts in physics, chemistry and biology, as life is not a thing but a process.

Organization and Biological Matter

An organism is any contiguous living system (such as animal, fungus, micro-organism, or plant). In at least some form, all types of organisms are capable of response to stimuli, reproduction, growth and development, and maintenance of homeostasis as a stable whole. An organism may either be unicellular (containing a single cell) or multicellular (containing many cells). The scientific classification in biology considers organisms synonymous with life on Earth. The word organism may broadly be defined as an assembly of molecules functioning as a more or less stable whole that exhibits the properties of life.

Biological matter is able to not only generate energy and preserve energy but also to build upon it. A biological system is working largely on inert un-animated matter, is exchanging electrons and protons, transforming them and creating complex molecular structures that allow the organism to survive, thrive and reproduce. In a cell, for example, which is made up of many molecules that are carefully combined in complex structures, there is a continual exchange of information. There is an exchange of not only random electrical charges but also of electrical charges in the form of information. This process, the aspect of information, has only recently become the object of studies in biological systems. As of yet, the publications that speak about this process mostly adopt a theoretical approach and discussion, however there is no practical presentation of this process.

Biological Cycles

In biological systems, we also find many cyclic processes and periodic functions which occurs at very different frequency ranges. If we look at many processes inside a biological system, we will encounter cycles that are ranging anywhere from several seconds to several hours to several days. In humans, we see that some of these cycles are actually even longer. A woman undergoes a regular menstrual cycle of approximately 28 days. Here we are looking at a cyclic periodic function of a biological system. And even though many chemical processes are involved as well, they operate at a very different timeframes. Generally, it is not possible to compare the timeframes occurring on a molecular level with the timeframes of biological phenomena that extend over very long periods of time.

Hence in biological systems we have cyclic processes that have periods of varying duration which usually correspond to vibrations in the extremely low frequency range (XULF). The study of low frequency cyclic processes in biological systems is called chronobiology.

In biological systems, there are several ranges of vibrations. On the upper end of the frequency spectrum are the vibrations of biochemical reactions caused by a constant exchange of ions, electrons, and protons, including interactions with light and heat. On the opposite end of the spectrum we can find <<biological vibrations>>, these are periodic or cyclic processes related to the functioning of the organism, some examples of periodic functions in biological systems include: heart beat, respiration, cell division, digestion, etc. While these biological processes involve an extremely large number of chemical reactions, they occur as unified processes and possess vibrations that are many orders of magnitude lower than the atomic, molecular and ionic frequencies of which they are comprised. Biological cycles are currently subject of study in the fields of chronobiology, circadian rhythms, and behavioural psychology.

REFERENCE

This subject is discussed in the book "la vie oscillatoire" from Albert Golbeter, which describes many of these processes from the perspective of organisms, cells, and macroscopic biological events.

The Role of Water

In all biological systems, water plays an important role in the organization of molecules and macromolecules as a great majority of them are bound with water. In chemistry water is described with the formula H2O. Water is a bipolar molecule containing opposing charges. As a result, biological systems exhibit a constant electrical dynamic due to the push and pull of positive and negative charges that are part of not only local bio-chemical and biological processes but also variations in the environment of the organism.

In a discrete water molecule, there are two hydrogen atoms and one oxygen atom connected by covalent bods. Two or more molecules of water can form a hydrogen bond between them because the oxygen of one water molecule has two lone pairs of electrons, each of which can form a hydrogen bond with another water molecule.

A hydrogen bond is the attractive interaction of a hydrogen atom with an electronegative atom, such as nitrogen, oxygen or fluorine, that comes from another molecule or chemical group. The hydrogen has a polar bonding to another electronegative atom to create the bond. These bonds can occur between molecules (inter-molecularly), or within different parts of a single molecule (intra-molecularly). The hydrogen bond (5 to 30 kJ/mole) is stronger than a van der Waals interaction, but weaker than covalent or ionic bonds. This type of bond occurs in both inorganic molecules such as water and organic molecules like DNA.

The hydrogen bond is often described as an electrostatic dipole-dipole interaction. However, it also has some features of covalent bonding: it is directional and strong, produces inter-atomic distances shorter than sum of van der Waals radii, and usually involves a limited number of interaction partners, which can be interpreted as a type of valence. These covalent features are more substantial when acceptors bind hydrogen from more electronegative donors.

The length of hydrogen bonds depends on bond strength, temperature, and pressure. The bond strength itself is dependent on temperature, pressure, bond angle, and environment (usually characterized by local dielectric constant). The typical length of a hydrogen bond in water is 197 pm. The ideal bond angle depends on the nature of the hydrogen bond donor. Where the bond strengths are more equivalent, the atoms of two interacting water molecules are partitioned into two polyatomic ions of opposite charge.

Water is unique because its oxygen atom has two lone pairs and two hydrogen atoms, meaning that the total number of bonds of a water molecule is up to four. The exact number of hydrogen bonds formed by a molecule of liquid water fluctuates with time and depends on the temperature. Because water forms hydrogen bonds with the donors and acceptors on solutes dissolved within it, it inhibits the formation of hydrogen bonds between molecules of those solutes or the formation of intra-molecular hydrogen bonds within those solutes through competition for their donors and acceptors. Consequently, hydrogen bonds between or within solute molecules dissolved in water are almost always unfavorable relative to hydrogen bonds between water and the donors and acceptors for hydrogen bonds on those solutes. So at any point in time the molecules of water are in a constant state of transferring energy or receiving energy. These characteristics are a crucial part of the uniqueness of water.

STATE OF THE ART

There are many technological systems existing today that are used to test various aspects of liquids and biological systems. However, none of these systems have the capacity to effectively examine the low frequency electrical phenomenon in these substances as the phenomenon in question is not of a directly chemical nature but part of a global and coherent electrical field. The invention allows the detection, identification and measurement of structured extremely low frequency (XLF) electric field waves that are inherent in all biological systems.

SUMMARY OF THE INVENTION

In a first aspect the invention provides a bioharmonic signal detection system for measuring a dynamic low frequency electrical field that surrounds biological systems, liquids, and bioactive materials, comprising of: a signal oscillator; a tunable resonator circuit that receives a signal at its input; a signal from the signal oscillator, wherein the tunable circuit further comprises an antenna that is coupled to a sample to receive the structured field; a ground plane resonator circuit that receives at its input an output from the tunable resonator; and an amplifier that receives at its input an output from the ground plane resonator and amplifies the bioharmonic signal measurement corresponding to the structured field. The tunable resonator circuit, the ground plane resonator circuit and the amplifier are grounded to a common potential which is configured to be floating.

In a preferred embodiment of the invention the signal oscillator is a variable square pulse wave generator.

In a further preferred embodiment of the invention a frequency of the signal output by the signal generator has a value below 2 kHz, preferably below 500 Hz.

In a further preferred embodiment of the invention the tunable resonator further comprises of connection in series to a first coupling capacitor, a second coupling capacitor, a resonator circuit, whereby the resonator circuit comprises a potentiometer and an inductance to adjust a resonance frequency of the tunable resonator, and the first coupling capacitor, the second coupling capacitor and the antenna have a common connection which is grounded via a grounding resistor to the common potential.

In a further preferred embodiment of the invention the grounding resistor has a value greater of equal to 20 M Ohm.

In a further preferred embodiment of the invention the ground plane resonator circuit comprises a first inverter, a diode, a second inverter, and a low pass filter circuit connected at its input to the connection between the diode and the second inverter and at its output to the common potential.

In a further preferred embodiment of the invention the low pass filter comprises a second resistor and a capacitor.

In a further preferred embodiment of the invention the amplifier comprises at least a third resistor, a darlington transistor, and produces an output for an audio transducer.

In a second aspect the invention provides a use of the bioharmonic detection system for detecting and identifying the presence of specific types of biological organisms such as fungi, plants, fish, birds, insects, animals, and people.

In a third aspect the invention provides a use of the bioharmonic detection system for detecting and identifying specific types of responses in a biological system such as the reaction of a biological system to an applied physical, chemical or electromagnetic stimulus.

In a fourth aspect the invention provides a use of the bioharmonic detection system for detecting and identifying qualitative measurements in agricultural and food products such as differences in maturity, vitality and chemical or biological contamination.

In a fifth aspect the invention provides a use of the bioharmonic detection system for detecting and identifying biological activity and bio-chemical interactions in plants such as photosynthesis, reproduction, enzyme catalysis and protein biosynthesis.

In a sixth aspect the invention provides a use of the bioharmonic detection system for detecting and identifying specific types of proteins and genomes.

In a seventh aspect the invention provides a use of the bioharmonic detection system for detecting and identifying specific types of contaminants in biological systems such as pesticides, heavy metals, chemical fertilizers, viruses, bacteria and parasites.

In an eighth aspect the invention provides a use of the bioharmonic detection system for detecting and identifying the presence of specific enzymes or genetic information in biological samples.

In a ninth aspect the invention provides a use of the bioharmonic detection system for coupling to a liquid or biological sample directly by contact, at a distance, or via another liquid or biological substance.

In a tenth aspect the invention provides a use of the bioharmonic detection system for detecting biological signal activity through insulating materials such as glass and plastic containers.

In an eleventh aspect the invention provides a use of the bioharmonic detection system for coupling to a liquid sample through direct contact, at a distance, via another liquid or substance such as plastic, glass, ceramic, carbon composite and wood.

In a twelfth aspect the invention provides a use of the bioharmonic detection system for obtaining qualitative and quantitative measurements related to chemical or biological contamination in water and fresh, packaged or prepared food products.

In a thirteenth aspect the invention provides a use of the bioharmonic detection system for detecting and identifying the presence of liquid, biological or bioactive matter in sealed containers, such as packaging and shipping containers.

BRIEF DESCRIPTION OF THE FIGURES

The invention will be discussed below in a more detailed way with examples illustrated by the following figures:

FIG. 16, 16a-16e: Measurement Qualities of a Typical Bioharmonic Signal.

FIG. 17 examples of Bioharmonic Tests on Liquid and Biological samples.

FIG. 18 examples of Bioharmonic Tests on Liquid and Biological samples.

FIG. 19 examples of Bioharmonic Signal Characteristics.

FIG. 20 Water Testing—Environmental & Physical Effects.

FIG. 21 Water Quality Testing—Electromagnetic Radiation.

FIG. 22 Water Quality Testing—Contamination.

FIG. 23 Water Quality Testing—Contamination.

FIG. 24 Water Quality Testing—Qualitative Test.

FIG. 26 Water Quality Testing—Bacterial Contamination.

FIG. 27 Water Quality Testing—Bacterial Contamination.

FIG. 28 Water Quality Testing—High Dilution.

FIG. 29 Water Quality Testing—Environmental Testing.

FIG. 30 Water Quality Testing—Environmental Testing.

FIG. 31 Water Quality Testing—Effects of Human Intention.

FIG. 32 Water Quality Testing—Effects of Human Intention.

FIG. 33 Water Quality Testing—Quality Control.

FIG. 34 Liquids Testing—Wine.

FIG. 35 Liquids Testing—Dangerous Substances.

FIG. 37 Plant Quality Testing—Behavioral Reactions.

FIG. 38 Plant Quality Testing—Genetic Modification.

FIG. 39 Plant Quality Testing—Genetic Modification.

FIG. 40 Plant Quality Testing—Genetic Modification.

FIG. 41 Plant Quality Testing—Micotoxin Contamination.

FIG. 42 Plant Quality Testing—Parasite Infections.

FIG. 43 Plant Quality Testing—Insect Infections.

FIG. 44 Plant Quality Testing—Viral Infections.

FIG. 45 Plant Quality Testing—Variety.

FIG. 46 Plant Quality Testing—Normal and Pathogenic States.

FIG. 47 Food Quality Testing—Cheese Maturity.

FIG. 48 Food Quality Testing—Food Additives.

FIG. 49 Animal Testing—Behavior Characteristics.

FIG. 50 Animal Testing—Behavior Characteristics.

FIG. 51 Human Testing—Sex Differences.

FIG. 52 Human Testing—Presence and Movement.

FIG. 53 Biological Testing—Human Blood Serum.

FIG. 55 Biological Testing—Human Skin Cell Samples.

FIG. 56 Biological Testing—Human Skin Cell Samples.

FIG. 57 Biological Testing—Human Cell Samples Cancer Screening.

FIG. 58 Human Testing—Effects of Natural Therapies.

FIG. 60 Human Testing—Psychological States.

FIG. 61 Human Testing—Differentiation of Identical Twins.

FIG. 62 Human Testing—Differentiation of Identical Twins.

Same reference numbers will be used throughout the figures and the whole description to designate same or similar features.

Basic Principles

Biological systems are surrounded by a dynamic low frequency electrical field that is a result of all physical, chemical and biological activities and processes within the organism itself and also those which constitute its immediate environment. The bioharmonic signal exists as a series of dynamic low frequency standing wave patterns that are formed through the interactions and resonant combinations between all mechanical, electrical, and electromagnetic activities that arise, surround and influence all biological organisms and systems. These interactions are sums of all mechanical, physical and biological phenomena and processes arising across the entire range of the electromagnetic spectrum. The bioharmonic signal contains information, in the form of waveform components that are harmonics and subharmonics of all periodic, oscillatory and instantaneous reactionary processes affecting a biological system. The sums of the interactions between all physical forces, chemical reactions, and biological processes of an organism, result in the formation of electrical and acoustic standing waves within the organism itself which also extend beyond its physical boundaries. Thus a bioharmonic signal can be detected at a considerable distance extending from the surface of a biological system or bioactive material and can also be detected through electrically insulating materials.

Figure 11:
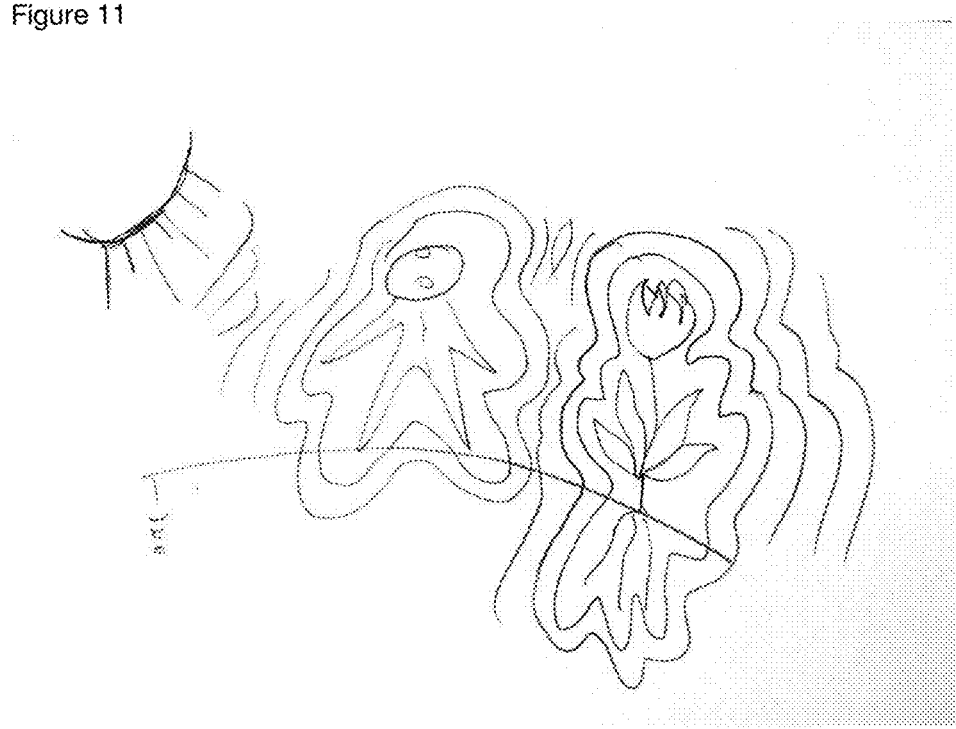
FIG. 11 illustrates a typical vibration having a relatively long period as is the case for a biological system.
Figure 12:
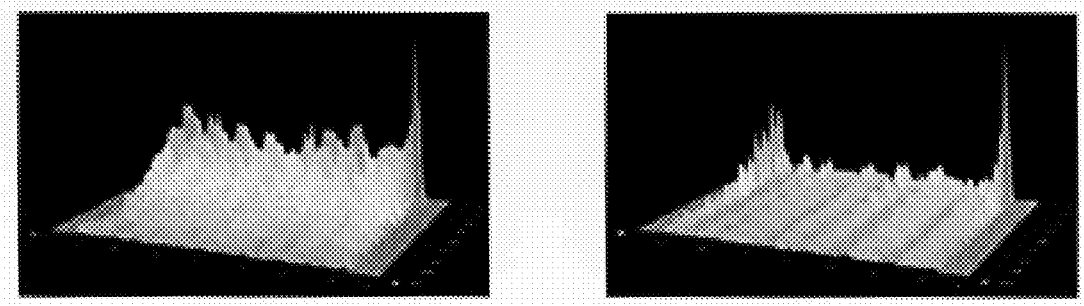
FIG. 12 illustrates a typical vibration for a biological system that is in a disturbed state.
Figure 13:
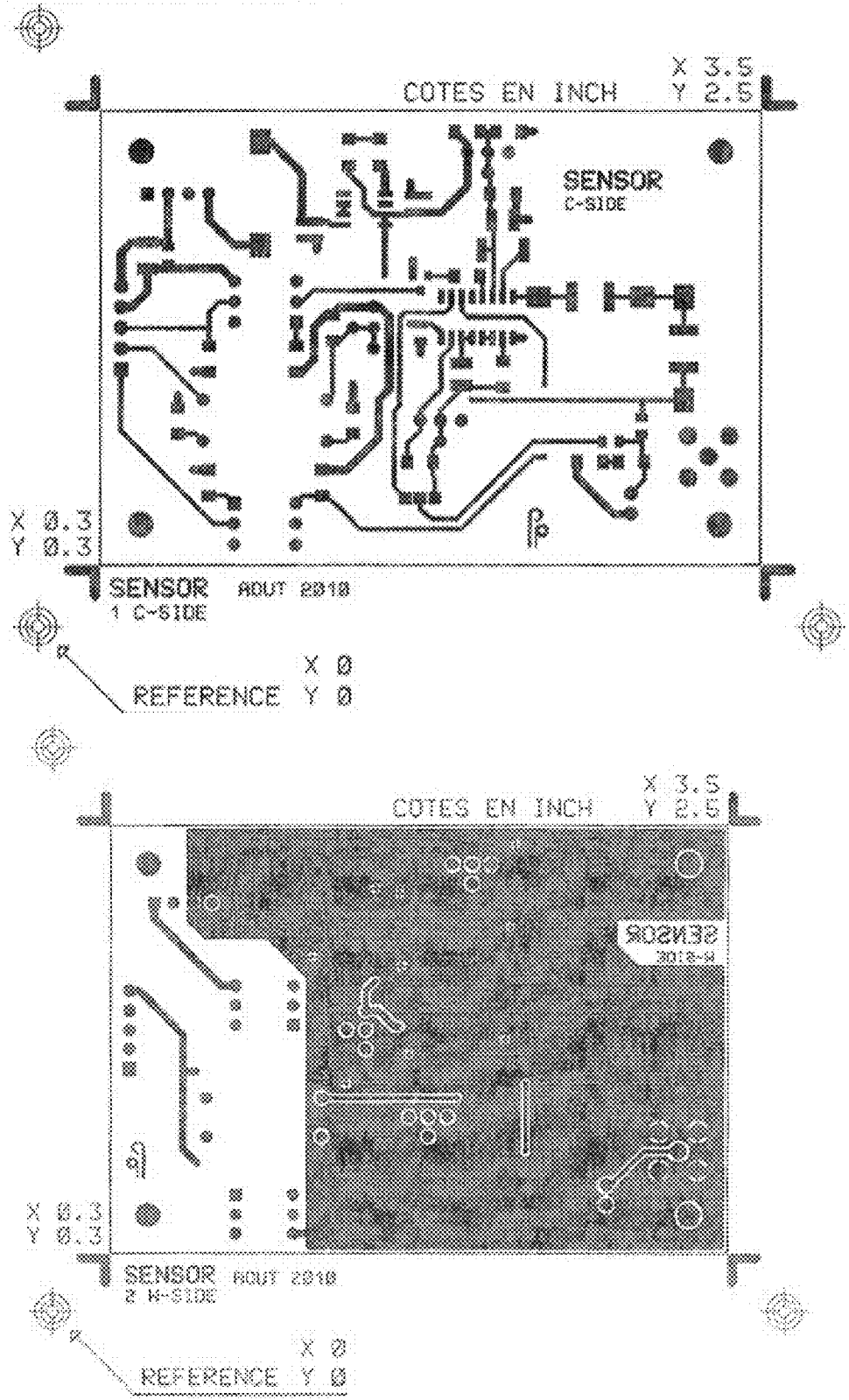
FIG. 13 Actual printed circuits.
Figure 13A:
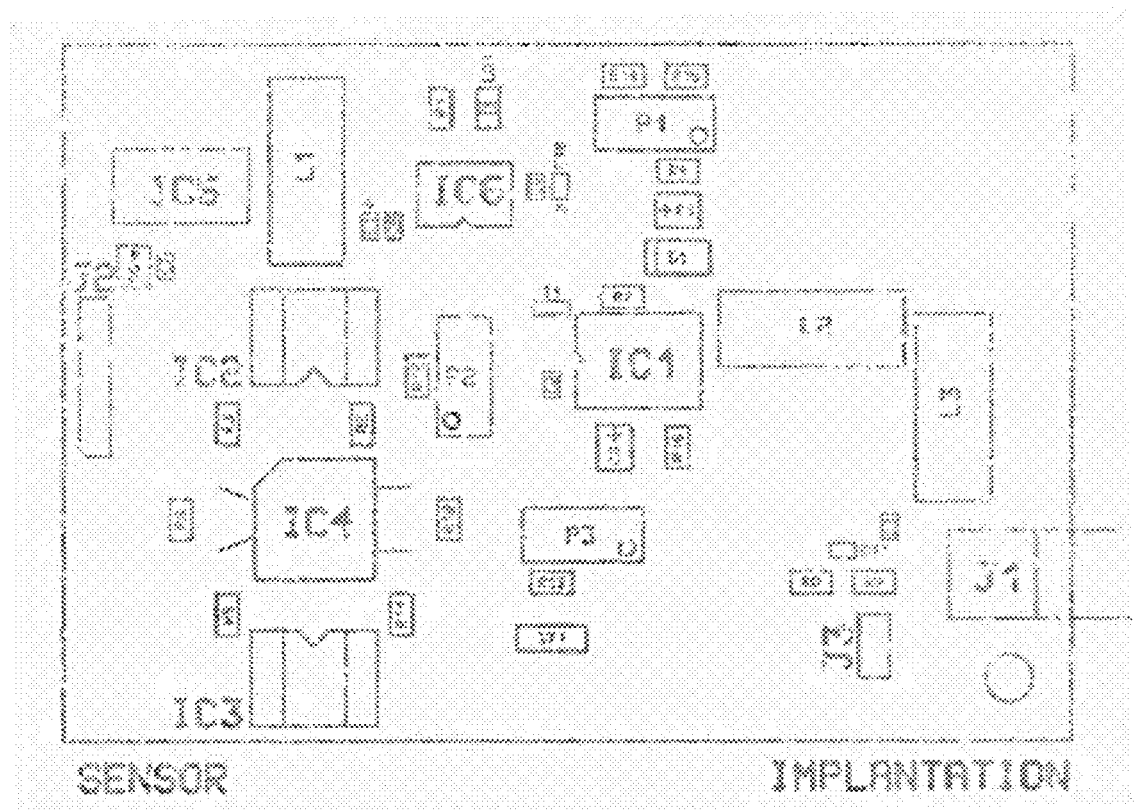
FIG. 13A Board layout.
Figure 13B:
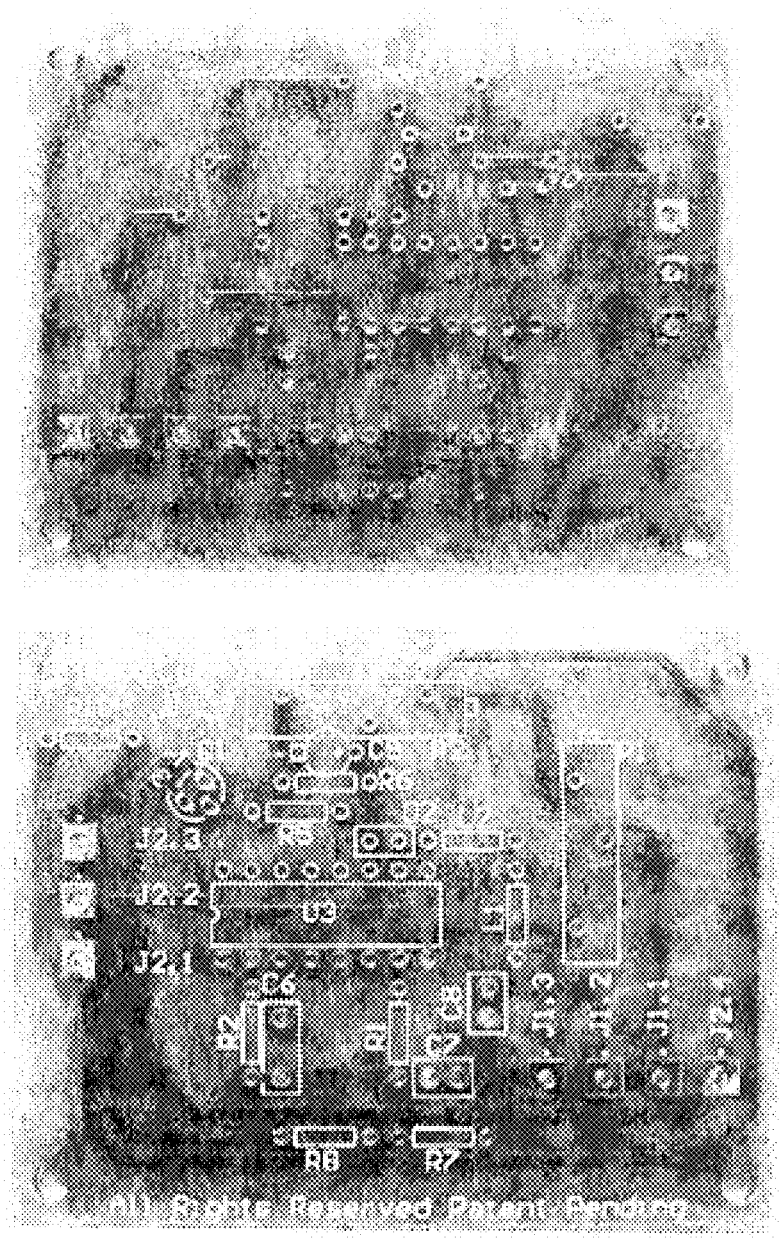
FIG. 13B Analog Circuit Board Layout.
Figure 13B:
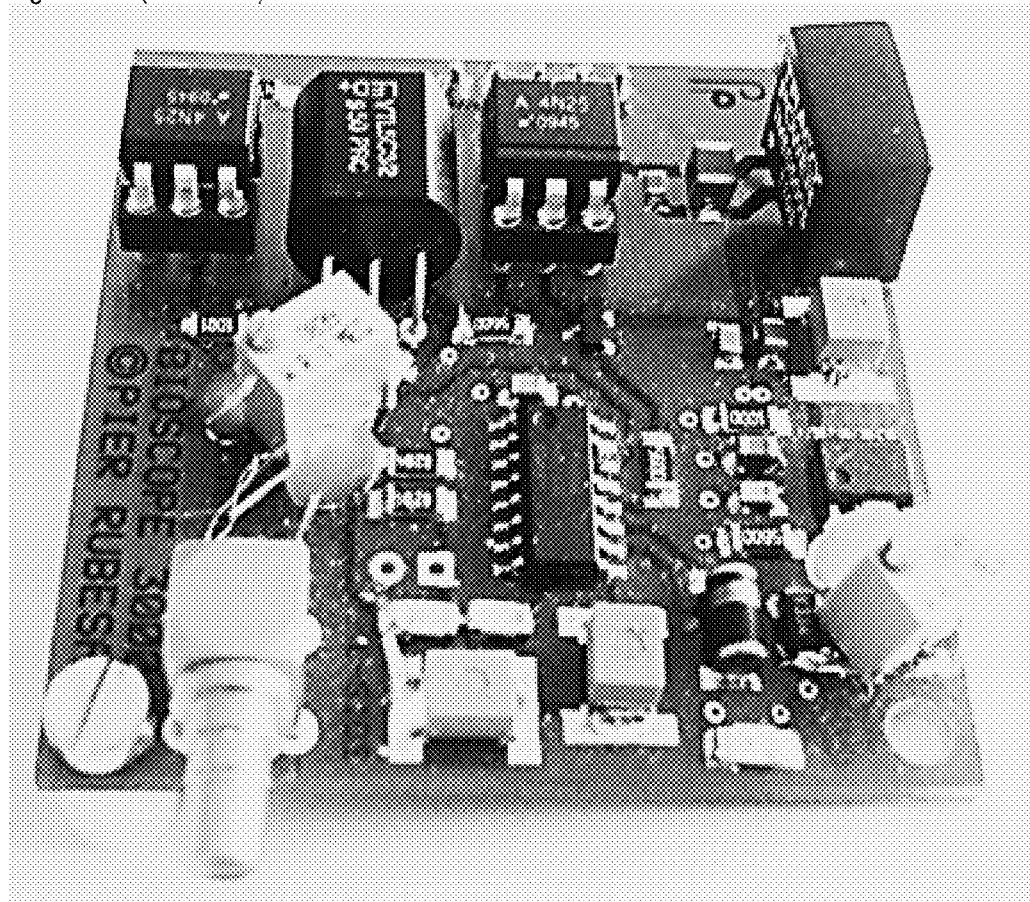
Figure 14:
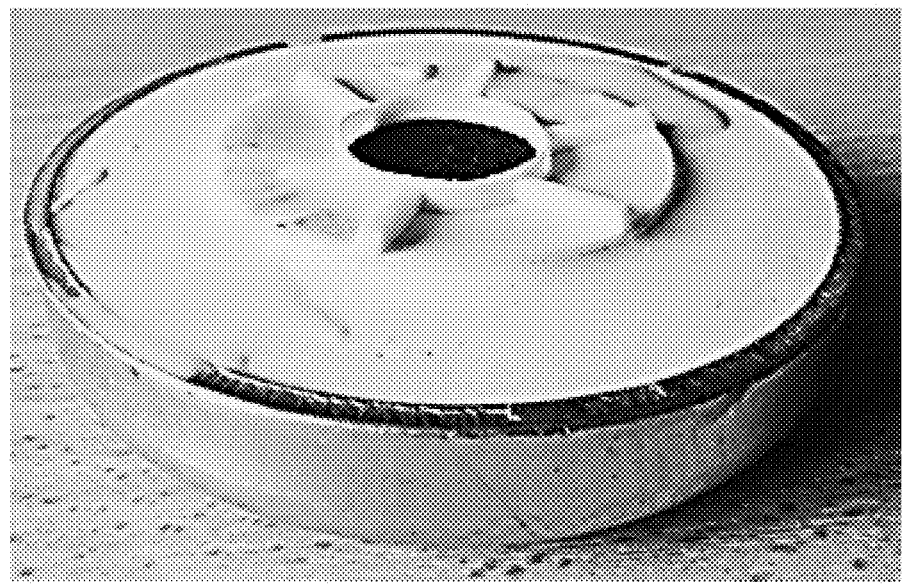
FIG. 14 Base antennas with different geometries.

Biological systems exhibit high degrees of organization which are essential processes that combine a variety of simple molecules and arrange them to from extremely complex structures. In comparison to inanimate matter, biological matter with its highly complex structure, is inherently unstable and susceptible to the forces of entropy. However, there is a macroscopic organizing force, which retains the structure and organization of biological systems. This organizing force can not be explained by standard biochemistry. The inventor has discovered, that if a biological system is in a good state, meaning that the process of homeostasis is in an optimal condition, it exhibits a bioharmonic signal that is highly structured. When the signal is decomposed using a spectral analyzer, it shows regular periodic modulations and harmonic variations that have relatively long periods and harmonic coherence, as shown in FIG. 11. If on the other hand the same biological system is in a disturbed state, the bioharmonic signal is altered and looks like shown in FIG. 12.

This example illustrates the different levels of electrical organization and structure in a biological system and its reaction to an applied external disturbance as a function of being in an undisturbed and organized stable state—also called coherence, or in a state of electrical disturbance—also called chaos. The disturbing effects by external influences caused by physical, chemical, or electromagnetic actions on the electric field coherence of biological systems is the same, whether we speak of plants, humans, animals, cells, and other bioactive materials such as water, essential oils and plant extracts, seed, etc. One positive aspect of the bioharmonic field is one of order, structure and coherence, the opposite influence on the bioharmonic field of a biological system or bioactive compound is one of disorganization, cancellation and chaos.

Some of the signals that are captured by the bioharmonic detection system, obviously are based not on individual cellular or molecular activity, but on the activity of the system as the whole. The individual cells and molecules are merely constituents of the entire organized system. The system as a whole, which is comprised of many hundreds of billions of cells which are undergoing a continual biochemical process that supports homeostasis, will have a residual charge, i.e., a residual aspect of electrical charges implying that there is some total coherent flow of electrons that are part of all biochemical activity in the system.

Let us consider again the example of a container of water. We measure the signal from the same water that we measure firstly in a ceramic cup, secondly in a glass, and thirdly in a crystal goblet. It is found that the same water has 3 very different spectra as output from the bioharmonic detection system. At first sight the fact of obtaining 3 different spectra for the same material substance may appear as a surprise. However it is to be noted that the geometry and composition of the recipient varies from one container to another and thus the different geometry and composition may be a parameter influencing the organization of water molecules in the system.

We must thus consider that all the molecules of water are held within space by a physical barrier, the barrier being the surface limit of the recipient, i.e. a ceramic cup, a silicon glass, or a crystal goblet. In addition, the cup, the glass, and the goblet, have different physical geometries, which means that the overall displacement of water and hence the arrangement of electrons and protons that make up the molecules, are spatially modified. It is believed that this aspect of spatial geometry plays a very important role in the characteristics of the global vibration that can be detected in biological systems which are largely composed of water.

In a further experiment, three freshly picked flowers from the garden are considered. Each flower was individually and successively placed next to the glass of water and a spectrum measured for each. The obtained result resulted in three very different spectra. In a model for a substance where only electrical charges are taken into account, no particular information can be derived if the substance is the flower. However with the flower, there is obviously a determined information present, which is in part the physical geometry of that flower and its unique biological makeup. The information reflects the fact that flowers have an intrinsic and global geometry such as having 4 petals, 5 petals, 12 petals, etc. The waveform information is related directly to the overall geometry of the system that plays an active role in the distribution of electrical and acoustic standing waves and it is on a level that is different/superior to its individual molecular or atomic structure.

From an electrical perspective, a plant that is growing in the garden is electrically grounded. As we have seen with the bioharmonic detection system measurements, the plant displays a difference in potential (potential charge) between ground and the plant surface itself. Even though the biological system, in this case the plant, is electrically grounded, there is another aspect, there is a type of variable dynamic voltage activity that is occurring in the system as a whole that cannot be explained by standard electrical or biological theory.

Geometry of Waveforms

Waveforms have a particular geometry. Their geometry is based on space (3 dimensions) and time (1 dimension), so all together 4 dimensions. So we have to think about geometry figures perspective because it is an electrical signal, it is a waveform that has a specific geometry.

The relationship between the excitation frequency of the antenna and the response of the system is based on the information contained in the electrical geometry of the waveform. The equivalency of this synoptic would be the frequency; we could say a kind of magnification, a parameter of magnification.

Changing the harmonic content or the waveform information that we use for stimulation can be compared to the focus parameter. So this relationship is very important, because we are changing the frequency and by changing the information contained in the stimulation signal even on the same sample we extract different types of information.

One of the determining factors for signal detection, capture and measurement is the geometry of the antenna and its coupling or its proximity to the sample. There are different ways the antenna can be used and applied. The resonance frequency depends also on how the antenna is applied. The excitation signal that is emitted by the antenna is in fact caused by a varying electrical charge on the surface of the antenna. Through the variance of electrical charge on the antenna surface, and the difference in harmonic content applied thus constitutes a low frequency excitation signal.

Every biological system is based on a certain molecular structure with a given molecular geometry, keeping the molecule intact. And in consequence every molecular structure emits specific geometrical waveform, and hence the content of information being displayed in relatively low frequencies within biological systems.

Example Application of Harmonic Geometry

Let us consider an excitation signal with the first, the second, the fourth, the fifth, the seventh, and the eighth harmonics. Missing in this list of harmonics are at least the third, the sixth and the ninth harmonics. Now, this has been sent out as an electrical charge. If we stimulate the system in this way, we will not touch the third, the sixth, and the ninth harmonics, which means as we pass electrical charge to the system, our output is going to contain information, all information except for third, sixth and ninth harmonics.

The Bioharmonic Detector

The bioharmonic detector is a device that can be used to detect bioharmonic signals in biological and bioactive matter. The system consists of a low frequency oscillator that produces an electrical signal, typically an electrical square wave whose duty cycle is equally spaced between the rising (or positive going) and falling (or negative going) pulse. The frequency of the signal when applied in testing of biological systems is typically in the frequency range between 20 Hz and 1 kHz. A number of common frequencies that are used are 96 Hz, 110 Hz, 156 Hz, 200 Hz, 212 Hz, 330 Hz, although any other value may be used as well. In general, any biological or bioactive sample may be tested using a variety of frequency settings as the changes in the frequencies can be compared to the "zoom" parameter in an optical microscope or telescope. Changes in the frequency setting of the oscillator will show different aspects of the electrical field activity in the sample.

The Bioharmonic Measurements

The International publication WO 2006/048456 A1 describes a device which allows the detection of structured fields that surround biological systems. More precisely the device is for detecting a field that emanates from an organism or from an organically supportive environment. Such device comprises of a base oscillator for generating a base signal at low frequency, a means for coupling a radiating vibration field and receiving a vibration signal emanated from said organism, and a signal oscillator for generating an output audio signal having a modulation input on which a modulation signal derived from said antenna is applied. In one example realization, the operational parameters of the base oscillator may be modified using a computer system.

The inventor discovered through the use of the bioharmonic system—which will be described further on in this description—that it is possible to detect these extremely low frequency (XLF) phenomena in biological systems and in bioactive matter.

The characteristics of the bioharmonic signal activity are derived via standard spectral analysis. The typical figures expressing those measurements are:

(i) A surface spectrum displays the dynamics of the low frequency periodic changes in the electric field's harmonic content over long periods of time. Typically a time frame of 15 seconds is applied, however, views of bioharmonic signal activity can be observed over several milliseconds, several seconds, or several minutes. The labels in the graph include the parameters of time (along x axis), amplitude (along the y axis), and frequency (along the z axis).

(ii) A frequency spectrum is a two dimensional representation of the average frequency and amplitude values of the bioharmonic signal that are derived from a sampling of the signal over a certain period of time known as the sampling window. Frequency is mapped along the x axis and amplitude along the y axis. The frequency band that is most typical of bioharmonic signal activity is in the range between less than 1 Hz and 5,000 Hz, although activity in the upper frequency ranges, 6,000 Hz through 50,000 Hz, can also show characteristics of bioharmonic signal activity especially when biological systems under test are treated with chemical products (i.e. reactants, acids, salts pesticides, etc.). The amplitude of the bioharmonic signal is displayed in volts (along the y axis) and the scale typically ranges from 1 to 5 volts. These values are indicative of the strength of the electric potential derived from the bioharmonic signal activity at a specific frequency. In biological systems for example, the bioharmonic signal activity is derived from the values of electrical activity that are based on physical and chemical reactions within the system where the information of the activity is based on the harmonic content in the low frequency band (1 Hz to 5 kHz), whose amplitude response is in the range between 1 and 5 volts, and varies over a period of time ranging from tens of milliseconds to several hours or more.

(iii) The average spectral amplitude can be applied as a measure of the absorption or reflection characteristics of a biological system under test. The value is derived by averaging the amplitudes of a desired set of harmonics (i.e. the 1st through the 19th harmonics). The mapping of average spectral amplitude serves as a comparison between samples which displays their average reaction to an applied excitation signal. The average spectral amplitude is a one dimensional graph whose y axis shows the value of the average power of the bioharmonic signal activity in volts (1 to 5 V).

(iv) The phase response of a sample is a two dimensional graph that maps the phase value of specific harmonics. Frequency is shown along the x axis and is measured in hertz. Phase values are mapped along the y axis and are a measure of the lead or lag of wave components taken from a reference, usually the first harmonic also known as the fundamental frequency. The phase is measured in degrees. Values in the positive domain represent a leading wave frequency values, values in the negative domain represent lagging wave frequency values. The phase response curve illustrates the transient change in the cycle period of a bioharmonic signal oscillation.

(v) The average phase of a bioharmonic signal represents the characteristics of a biological sample whose electric field has a tendency to lead or lag the reference value of an applied external excitation signal. The average phase values are used to determine the speed and direction of the rotation of the bioharmonic signal in a biological or bioactive sample. In biological systems, positive phase values represent the movement of the electric field in a clockwise direction, while negative phase values represent movement of the electric field in a counterclockwise direction. The value, in phase degrees, can be used to determine the rotational speed of the bioharmonic signal.

(vi) Orbital analysis is a method that can be used to illustrate structural and geometric valuations in the phase of a bioharmonic signal. Biological systems are highly organized systems and their inherent modulation of extremely low frequency electric fields, which are the sum total of all physical, chemical, and biological activities, result in clearly recognizable geometric patterns. The orbital graphs map the phase of the bioharmonic signal in degrees vs frequency.

Signal Capture Techniques

In any biological system, we can non-destructively detect the bioharmonic signal according to four different testing techniques. A bioharmonic signal can be derived either:

(i) at a distance, where the electrode is placed anywhere from several centimeters to several meters from the surface of a biological system. This method allows the detection of the presence of a biological or bioactive material and can be used in applications where the detection of biological contamination is an issue. It can be used to detect the presence of biological or bioactive matter in shipping containers, or sealed packages. It can be useful for measuring the intensity and characteristics of the bioharmonic field in biological research. It can be used in the detection of people.

(ii) by contact where the electrode is directly connected to a biological system's surface i.e. the stem of a plant. This technique can be used to evaluate the quality of food products such as fruits, vegetables, meat, fish, fowl, game, etc. It can also be used in evaluating the bioharmonic signatures of biologically derived products such as plant extracts, sugars, animal and vegetable proteins, enzymes, etc. The contact technique can be applied in measuring biological activity in plants, animals, cells, and humans.

(iii) by using water as a contact medium, where the electrode is coupled with a recipient filled with water. When this technique is applied, the changes in the bioharmonic signal in the water reflects the electrical disturbances in the nearby environment. This technique is useful for detecting strong electromagnetic disturbances as the polarizing effect of ambient electrical and magnetic fields will cause a reorientation of bipolar water molecules and these changes will affect the spectral harmonic and dynamic properties of the bioharmonic signal in water.

(iv) via another organism or bioactive material, where the electrode is connected to one biological sample and the reaction is measured when another biological organism is placed in proximity or contact with the first. This technique can be applied in many applications where the reaction of one biological system can be non-destructively tested with respect to the influence of other biological systems or bioactive materials. For example, the reaction in the bioharmonic signal of an apple can be tested when the apple is placed in the proximity of an electromagnetic field such as in a refrigerator. The apple can be tested with respect to its proximity or contact with other food products. The apple can be tested with respect to the effects of externally applied chemical agents such as pesticides and waxes.

DETAILED DESCRIPTION OF PREFERRED EMBODIMENTS

Bioharmonic Signal Detection System Use

With the inventive bioharmonic detection system, which will be described in detail later in this section, it was discovered that it could be used to obtain a signal from a live cell culture by coupling the electrode to the sample. Similarly, the bioharmonic detection system can be coupled to a larger biological system such as the stem or leaf of a plant, where a signal is also obtained. In addition, the bioharmonic detection system can be coupled to a very large biological system, such as a human or even a tree, and yet another signal is obtained. In these examples we observe an electric field that is different by many orders of magnitude, despite the fact that no setting is made to the bioharmonic detection system to increase power output to the electrode.

The bioharmonic detection system can be used to capture the electric field modifications in liquids and biological samples when those samples are treated or stimulated in some way. One example includes coupling the bioharmonic detection system electrode to a plant stem and then treating the plant with a chemical product such as an insecticide, placing a flame near a leaf of the plant, placing another plant next to the plant being tested, making a cutting from the plant. In each case, a clear and distinct modification to the signal will be detected. Another example involves a glass of water that is coupled to the bioharmonic detection system. When another liquid is placed in the proximity of the coupled sample, changes in the electrical quality of the water can be observed, when the placed liquid is removed, the electrical field of the coupled sample will return to its initial condition. This transfer of electrical information that causes a modification in the coupled sample signal can be further demonstrated by placing vials of concentrated plant extract or essential oils in the proximity of the coupled sample, in this case a glass of water, even though the vials containing the plant extract or essential oil are sealed, each instance will induce a unique signal in the coupled glass of water. A further example can be demonstrated by coupling a human body to the bioharmonic detection system. When an action is applied to the human body, such as exposure to a sound source, the placement of an active mobile telephone in the proximity of the body, or even a food product that is placed directly on the body, a change in the electrical field can be observed.

At first glance, the bioharmonic detection system block diagram merely suggests that it is a circuit comprising of a conventional low audio frequency oscillator, an antenna or electrode, a resonator, and an amplifier. In order to emit an electric field, a certain power is fed to the antenna, such that it is radiating a variable non-acoustic signal at a very low frequency, typically in the frequency range between 20 Hz and 2,000 Hz. If the radiating electric field signal output were to be increased by intervening in the oscillator output, it would be necessary to adjust an appropriate voltage or power output. However no adjustment to the voltage power output is made between measurements of the small cell culture sample, the larger plant, or the tree. Using the same amount of output, the same voltage, the same current—note that the bioharmonic detection system is generally powered by a conventional 3 to 5 volt USB port connection—we can project a bioharmonic signal that is as large as a tree, or we can test several cells in a cell culture. These results tell us that the nature of this phenomenon is not very typical.

Now we return back to the known effects of electricity and electromagnetism. Let us consider a table made from wood—wood is electrically neutral, it is an isolator. If an electric potential of 200 Volts is applied underneath the table, and a person touches the surface of the table, nothing noticeable will happen to the person, who undergoes absolutely no risk.

Coming now to bioharmonic signal measurements through the table, the bioharmonic detection system electrode is positioned underneath the table. If for example a rock is positioned on the table, no signal will be measured by the bioharmonic detection system. If instead a leaf of a plant is positioned on the table, then the bioharmonic detection system captures a signal. What does this mean? Information in the form of some kind of signal is penetrating this electrically neutral isolating material—in this case a wood table. Under current electrical theory, it is certainly unlikely that the leaf will contain sufficient electric charge to stimulate the neutral atomic structure of wood and thus transfer an electrical charge to influence the bioharmonic detection system electrode that is underneath. This raises the question as to the nature of the signal, and to the phenomena that is occurring. Furthermore, even if a highly charged non organic object is placed on the table, we will see that there is absolutely no reaction to the output of the bioharmonic detection system.

A further example of a biological system that causes a bioharmonic signal to be measured by the sensor electrode is essential oil, for example contained in a sealed container. As the latter is placed on the table, a bioharmonic signal can be detected. Different types of essential oils will exhibit unique spectral characteristics. The process by which this information transfer occurs is as of yet largely not understood by the majority in the community of physicists, chemists and biologists.

First Preferred Embodiment

Figure 5:
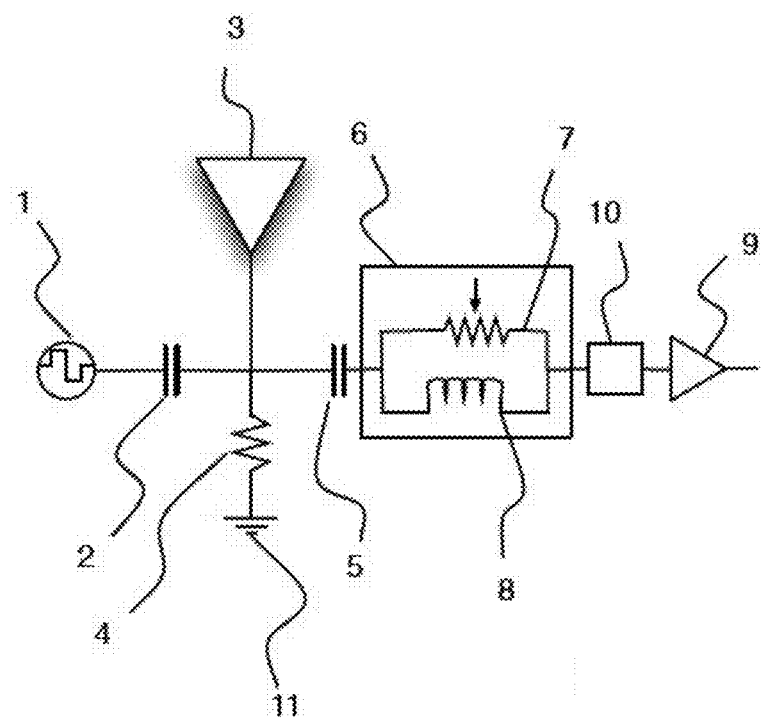
FIG. 5 Circuit of a bioharmonic device in a preferred embodiment according to the invention.
Figure 6:
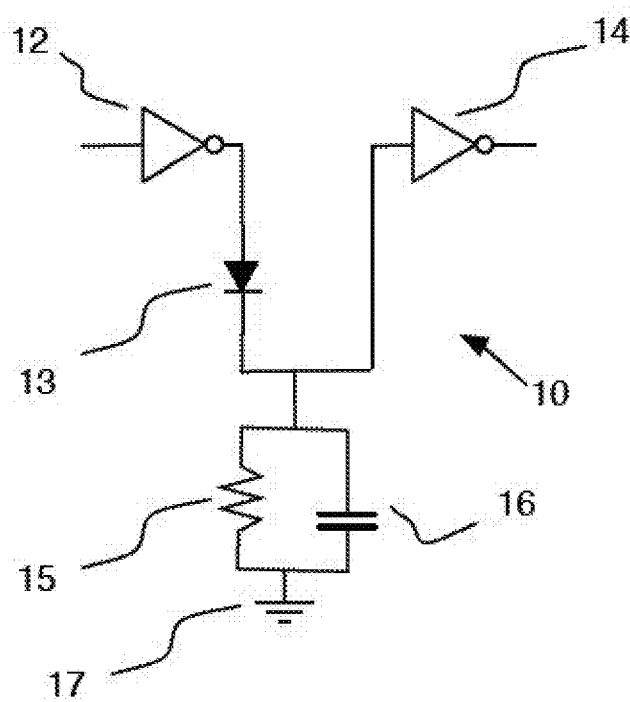
FIG. 6 Ground plane resonator circuit in a preferred embodiment according to the invention.

The following will describe the structure of the inventive bioharmonic detection system in reference (FIG. 5). While there is practically an unlimited manner in which each of the individual described modules can be electrically configured, only the most simple, specific, unique and inventive configurations of this invention will be described. Thus, the bioharmonic detection system comprises several base modules as described in the following section.

First Module—Oscillator

The first module of the bioharmonic detection system is an audio frequency signal oscillator 1, which typically produces a square or pulse wave. This variable pulse wave is produced in a frequency range anywhere between 20 Hz and 2 kHz. Frequencies towards 2 kHz are rarely used. Generally, the measurements made with the bioharmonic detection system on liquid samples, plants and human subjects use oscillator output frequency settings that are below 500 Hz.

In the first embodiment, the basic structure of the oscillator resembles known simple logic gate oscillator circuits. It comprises an embarked circuit, comprising of three inverters, a resistor, a capacitor, and a further resistor to produce the oscillation. If one of the resistors is a variable resistor such as a potentiometer or a slider, the frequency of the oscillator can be adjusted.

A basic CMOS logic oscillator configuration using a HEX Inverter is illustrated as follows:

The electrical configuration of the oscillator module that is used in the bioharmonic detection system is not limited to the basic illustration supplied here. When embodying the signal oscillator using CMOS logic, multiple types of HEX Inverter integrated circuits can be used for the purpose, for example the 74HC04, CD4049UB, CD4069UB, CD4093B, or their equivalents.

Figure 1:
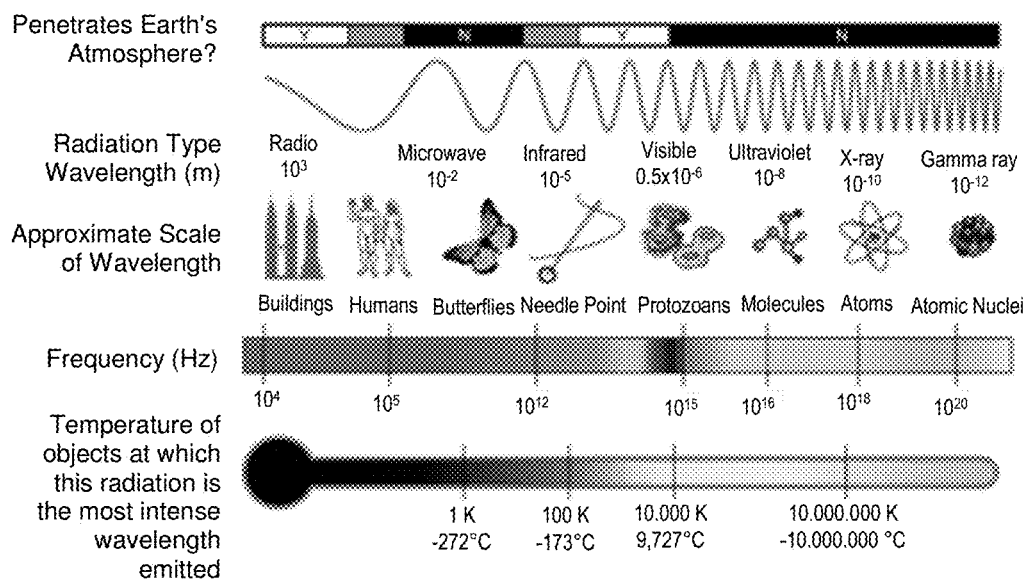
FIG. 1 The electromagnetic continuum covering the entire band of vibrational wavelengths and frequencies, ranging from the scale of atomic nuclei through to macroscopic objects such as buildings.
Figure 2:
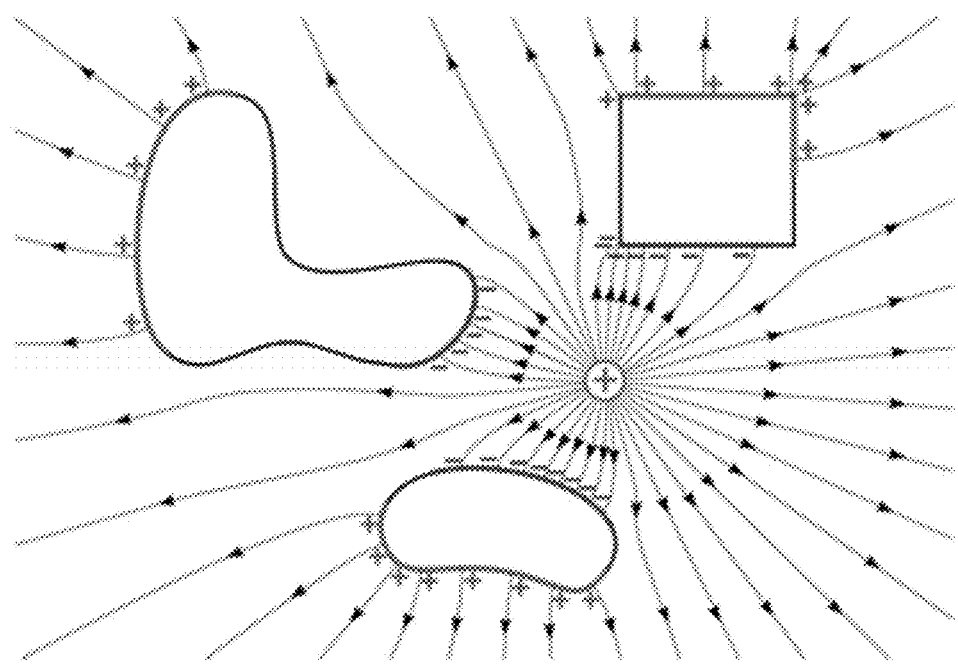
FIG. 2 Electrical force phenomena showing the spatial position of charge and magnetic field lines.
Figure 3:
FIG. 3 Biological system.
Figure 4:
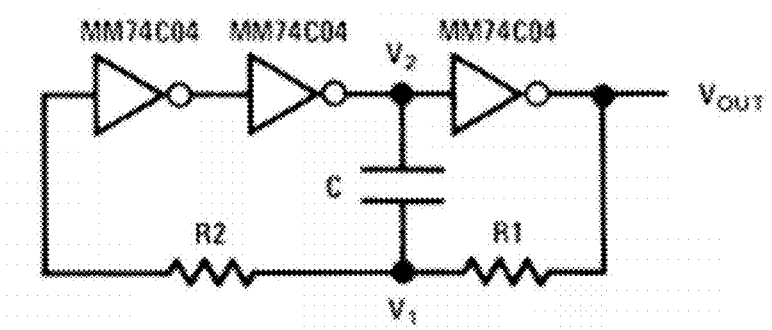
FIG. 4 CMOS oscillator.

See FIG. 4 CMOS Oscillator

More complex oscillator designs can be used for the purposes of supplying a low frequency signal to the coupling electrode or antenna using either analog or digital circuits, a comprehensive list of all possible options and permutations is out of scope within this document.

Additionally, digitally generated audio frequency signals can be applied to the coupling electrode or antenna, such as those generated by modifying the output voltage of a microcontroller digital or analog pin output. An example of a simple C program that can be used to generate different frequencies of a square wave output using an analog potentiometer to control the digital oscillator frequency using the PWM output pin of the microcontroller is presented as follows:

```
#include <Oscil.h> // oscillator
const int POT_PIN = 3; // set the analog input pin for
the potentiometer that controls the frequency
void setup( ){
    Serial.begin(115200); // set up of Serial output in
order to display potentiometer values
}
void updateControl( ){
    // read the potentiometer
    int pot_value = analogRead(POT_PIN); // value is 0-
1023
    // print the potentiometer value to the Serial monitor
    Serial.print("pot_value = ");
    Serial.print(pot_value);
    Serial.print("\t \t"); // prints 2 tabs
    int frequency = pot_value*3; // Set frequency value
    // print the frequency to the Serial monitor
    Serial.print("frequency = ");
    Serial.print(frequency);
    // set the frequency
    aSignal.setFreq(frequency);
    Serial.println( ); // next line
}
```

Many other forms of software routines combined with direct microcontroller audio signal output combinations can be used to obtain a similar result.

It should also be noted that the output power of the oscillator does not exceed the maximum power of the supply voltage which is typically between 3 to 5 volts.

The coupling electrode or antenna, can also be supplied with an external audio signal generator such as the output of a synthesizer, digital signal recorder, or function generator, providing the required frequency. In addition, the bioharmonic detection system will equally operate if the output waveform of the oscillator is a signal other than a square or pulse wave. Thus many different types of waveforms, having the required frequency may be used. Wherein each specific type of audio signal applied to the coupling electrode or antenna will yield a different response from the system being tested.

Second Module—Signal Coupling

The second module of the bioharmonic detection system is connected to the output of the signal oscillator 1 and comprises a first coupling capacitor 2 connected to an antenna 3 (high impedance antenna), the latter being further connected to ground 11 via a resistor 4 of relatively high value (typically 20 M Ohms or more). The antenna is further connected to a second coupling capacitor 5, which is connected in series with a resonator circuit 6, i.e. a circuit comprising a potentiometer 7 and an inductor 8 connected in parallel. The inductance value of the inductor is quite high, typically 1 mH (mili-Henry). By adjusting the potentiometer value, resonance in the circuit ensues. The output of the resonator circuit 6 is fed to a ground plane resonator circuit 10. This produces an very high sensitivity on the antenna, but in the same time, extremely low noise.

Both first and second modules are connected to form a tunable resonator.

Third Module—Ground Plane Resonator

As shown in FIG. 5, the ground plane resonator circuit 10 comprises a first inverter gate 12 which outputs its signal to a diode 13 preventing the back-flow of current, which in turn outputs the signal to a second inverter gate 14. An inverter gate just inverts the signal's polarity, meaning if it is high at the input of the inverter gate it is changed to low at the inverter gate output and vice-versa. As such, the inverters each function as switches. The diode 13 is used to cut off a part of the signal output by the first inverter gate 12, which initially changes polarity from high to low, but after passing the diode 13 the signal keeps only one polarity, e.g., the signal of positive polarity. Hence the signal only oscillates between high and neutral state, because all signals of negative polarity are filtered out. The latter signal is then fed to a filter, which is a basic resistor 15 capacitor 16 circuit, a simple RC circuit, which in turn is connected to ground 17. With the simple RC circuit we have a low pass filter, which allows low frequencies to pass to the next gate stage. The low pass filter acts with respect to the output of the inverter gate 12 and diode 13 assembly, at the same time, with respect to ground 17. This means that the polarity between the positive 4 and the negative phases the wave pulse rests at a certain non-zero electrical value potential with respect to ground, causing a non-grounded electron flow whose base frequency is dependent on the excitation oscillator, at the input of the second inverter 14.

It is thought that this configuration creates a state of electrical non-equilibrium, not according to the logic of the circuit, but on the component silicon itself that makes up the circuit (i.e. inside the inverting gate), where the two charges between the high-low states are electrically driven into an unstable or critical state. As we are passing a complex spectrum at the input of the first inverter gate 12 while this inverter can basically only function as a switch that goes on and off, it is believed that while performing test measurements we are creating an instability in the inverter gate. In this manner we are forcing the silicon inside the chip to go into an intermediate electrical state between the base and conducting band. We are forcing the charge that has been carried across the semiconductor material inside the integrated circuit to vary, as the harmonic information of the wave in causing an excitation of the component electrons across the silicon, and this variation is creating an unstable gate resulting in low frequency resonance.

The type of inverter gates 12 and 14 used in the ground plane resonator circuit 10 may be for example 4049 CMOS inverter buffers, however any type of TTL level CMOS inverter could be used for this purpose such as the HC7404, 4069, etc., in addition, the electrical configuration may employ a Schmitt Trigger such as the 5414, 7414, etc. It is to be noted that in practice, under certain conditions, the temperature of the inverter gate 12 and 14 component may become extremely high. It may even occur that an inverter gate 12 or 14 the logic chip will produce an audible acoustic noise.

It is further thought that the assumption under which the electrical ground is at zero electrical potential, i.e., neutral, is not entirely correct. In fact biological systems, are using a variation of potential at ground to counter the otherwise increased entropy. So somehow, biological systems are making a feedback loop, between what we consider as ground and what we consider as charge. It is believed that the configuration in the ground plane resonator circuit 10 gate which is connected to ground induces a current flow in the form of ground hum which is part of this described phenomenon. So having an electrode of extremely high impedance, we believe that biological systems contain information that can be dispatched via variations in electrically neutral ground and the variations in electron flow which are constant in earth's atmosphere, and that this signal interacts through ground and is detected by this circuit 6. While the whole resonator circuit is disconnected from ground, the ground connections 11, 17 and the one from the amplifier (reference 32 in FIG. 4) are all interconnected. In other words, the ground plane resonator has floating ground which, we believe, is the source of the bioharmonic signal.

Fourth Module—Amplifier

Figure 7:
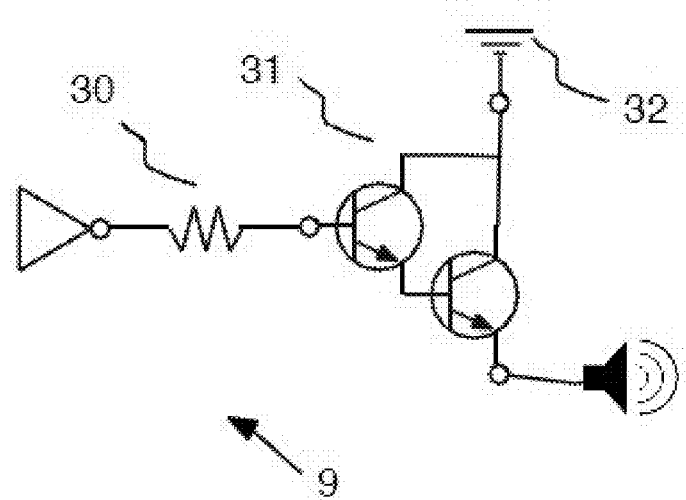
FIG. 7 Amplifier as used in the bioharmonic according to the invention.
Figure 8:
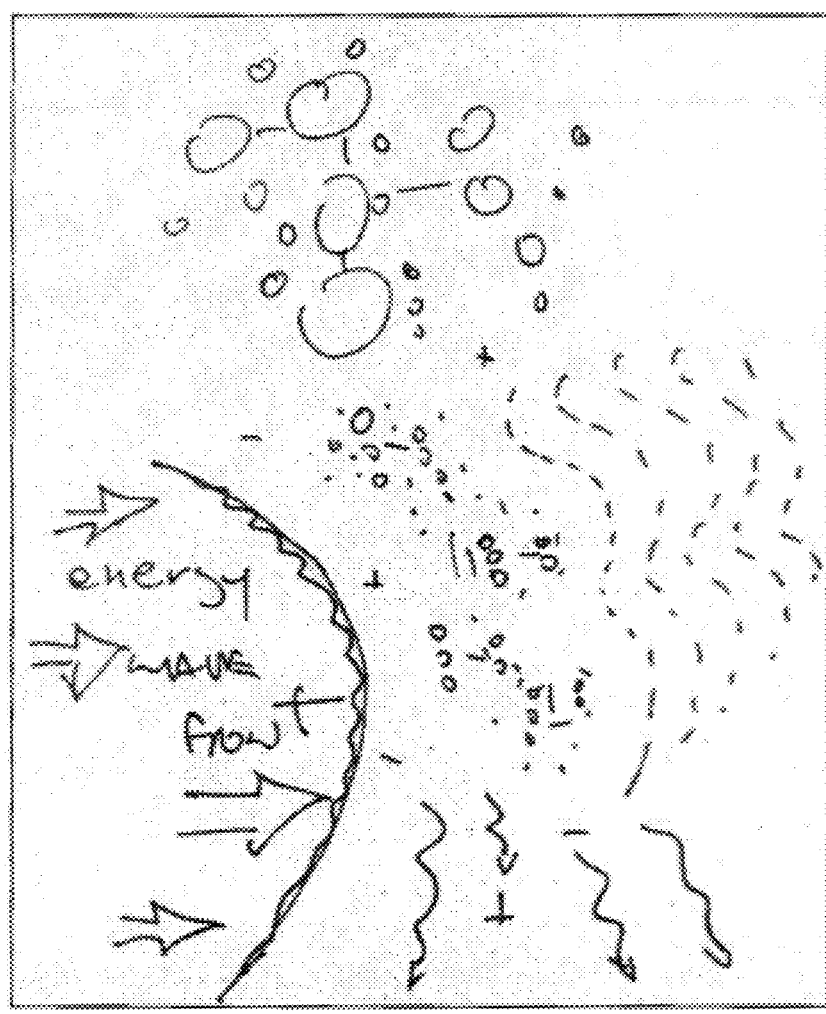
FIG. 8 Schematic explanation of electrical and/or force phenomena between atoms and molecules in living material.
Figure 9:
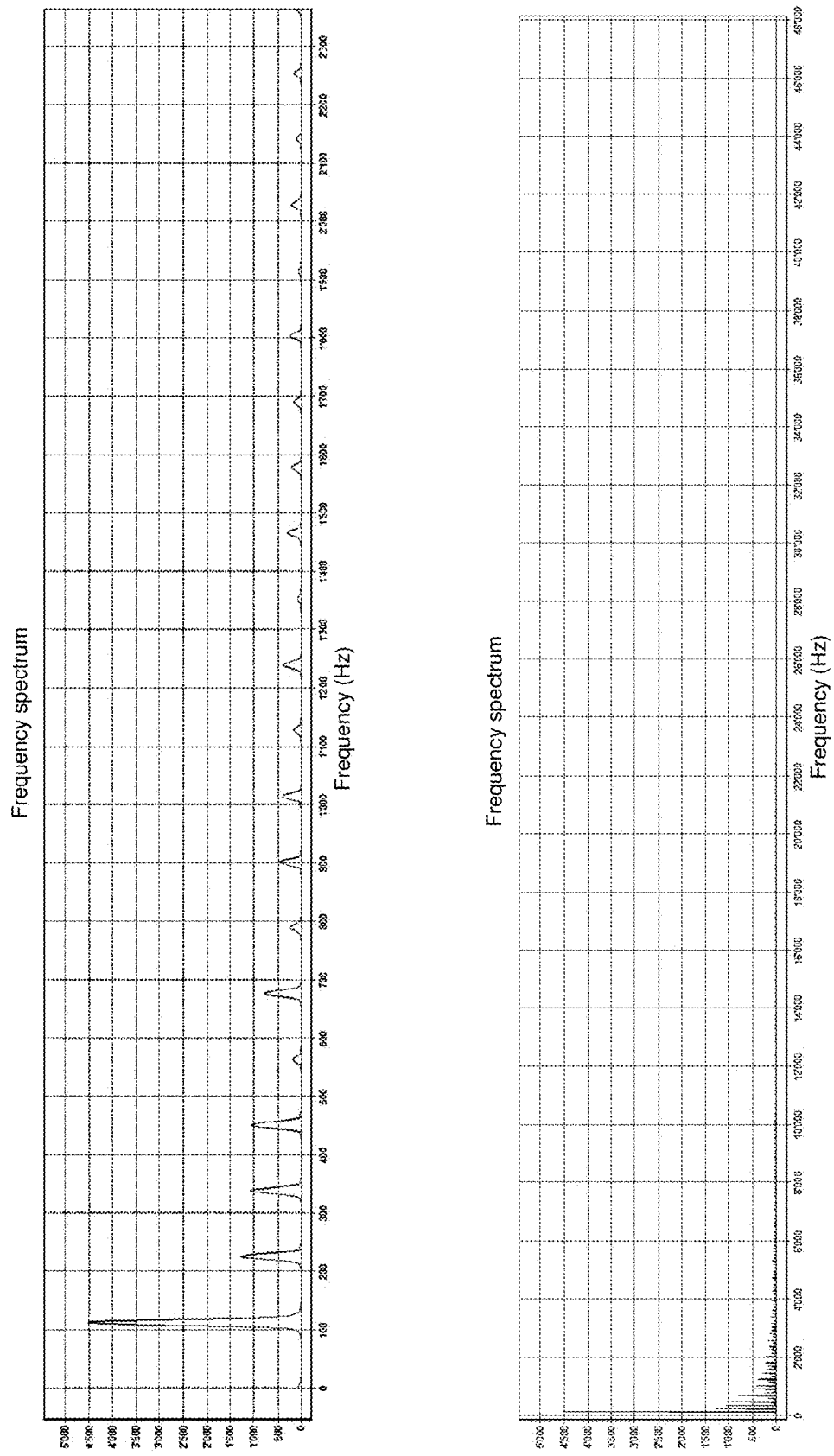
FIG. 9 Illustration of a series of harmonics attributed to a generic vibration.
Figure 10:
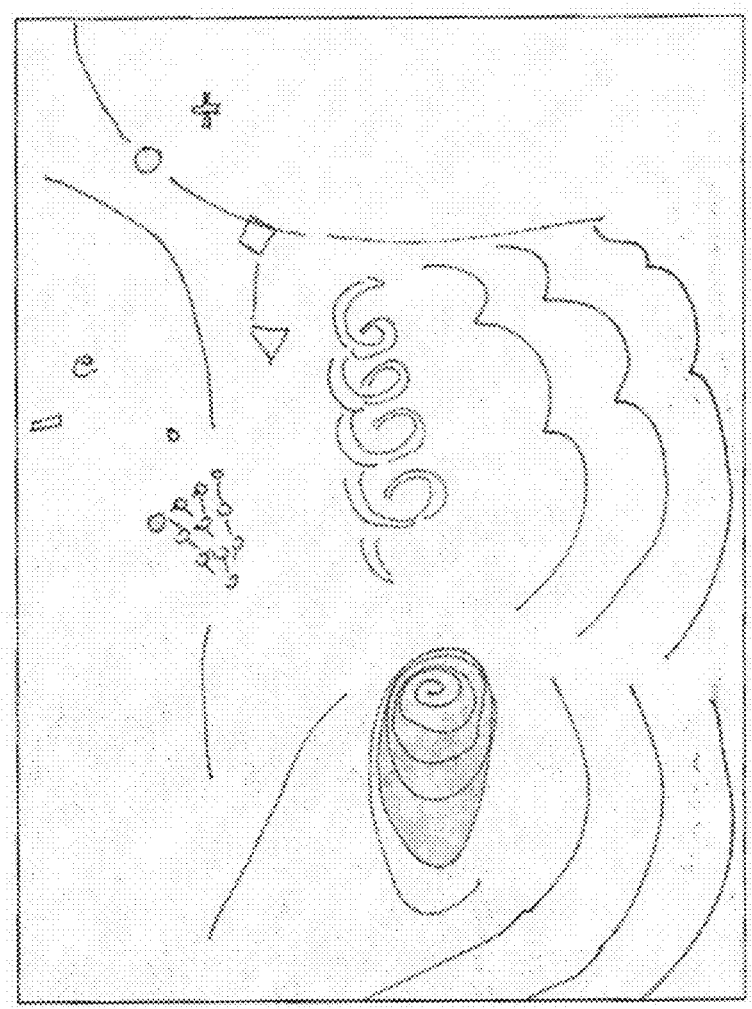
FIG. 10 illustrates how biological matter builds on energy.

The fourth module of the bioharmonic detection system is the amplifier 9 shown in FIG. 5, FIG. 7 contains an expanded view of the amplifier 9 in a preferred embodiment.

The amplifier 9 receives the output from the ground plane resonator 10 and comprises a resistor 30 and a Darlington transistor 31. The resistor 30 is limiting the voltage before the signal reaches the Darlington 31 for amplification where a gain value of 20,000 to 1 is typically employed. The output of the Darlington is connected directly to the signal output terminal for obtaining an audio signal. The Darlington transistor 31 is also connected to ground 32. As explained in the section pertaining to the third module, the ground connection 32 is connected to the other ground connection 11 and 17 and remains floating since the whole circuit is in fact disconnected from electrical ground.

Second Preferred Embodiment

Optical Signal and Power Coupling

Figure 15:
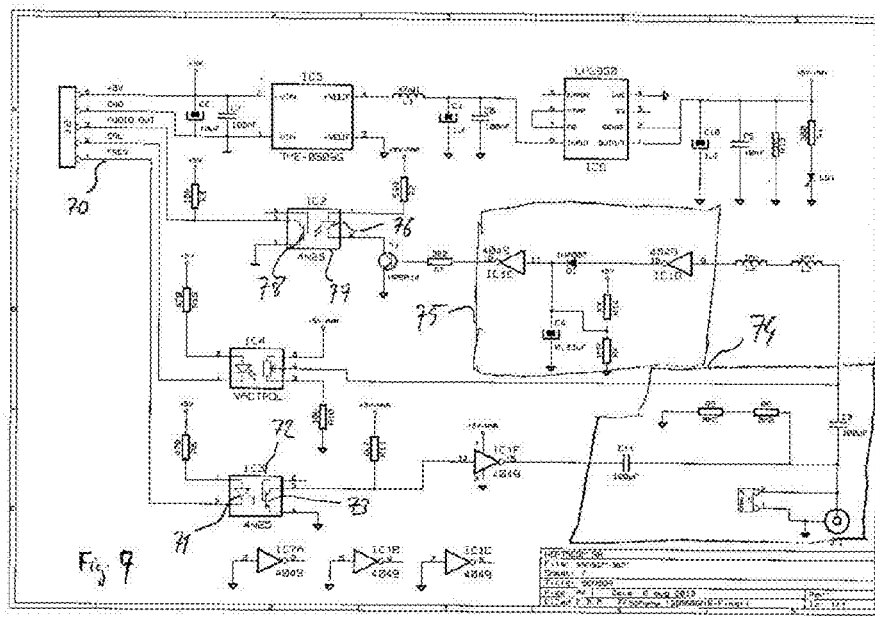
FIG. 15 Embodiment of a bioharmonic according to the invention.
Figure 15A:
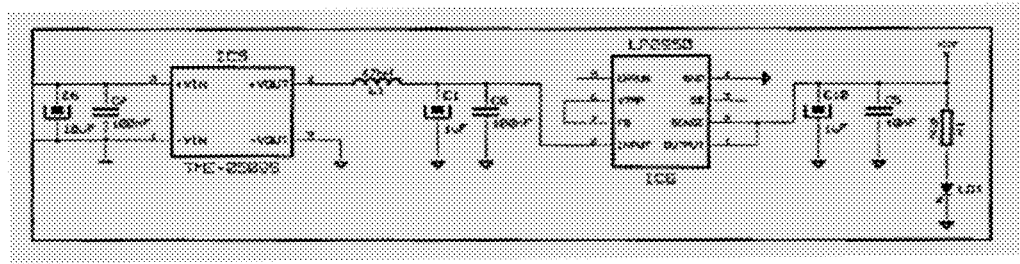
FIG. 15A Optical Power supply.
Figure 15B:
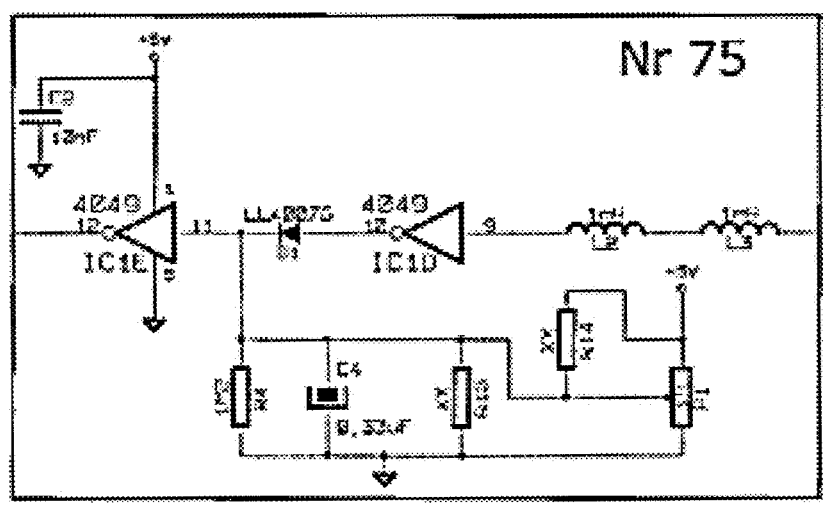
FIG. 15B Resonator Circuit.
Figure 15C:
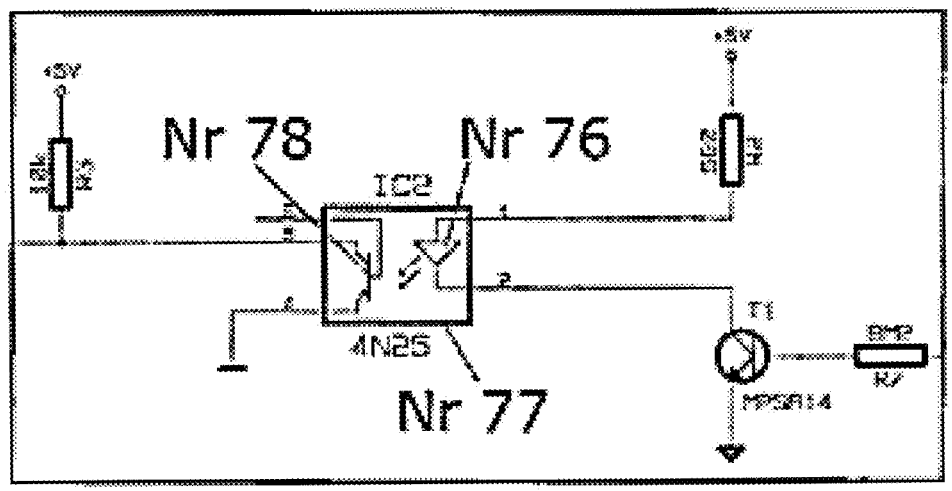
FIG. 15C Amplifier Circuit.
Figure 15D:
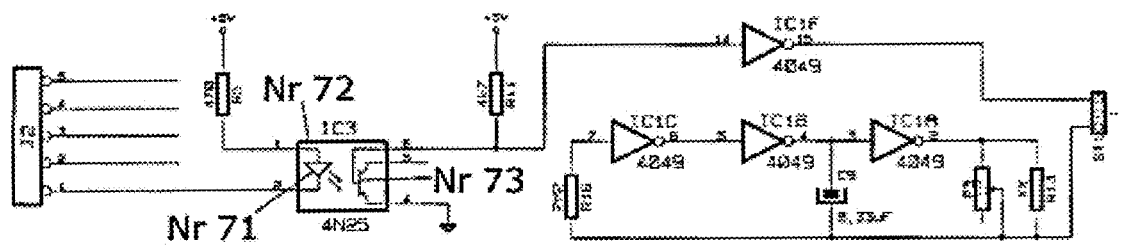
FIG. 15D Oscillator.
Figure 15E:
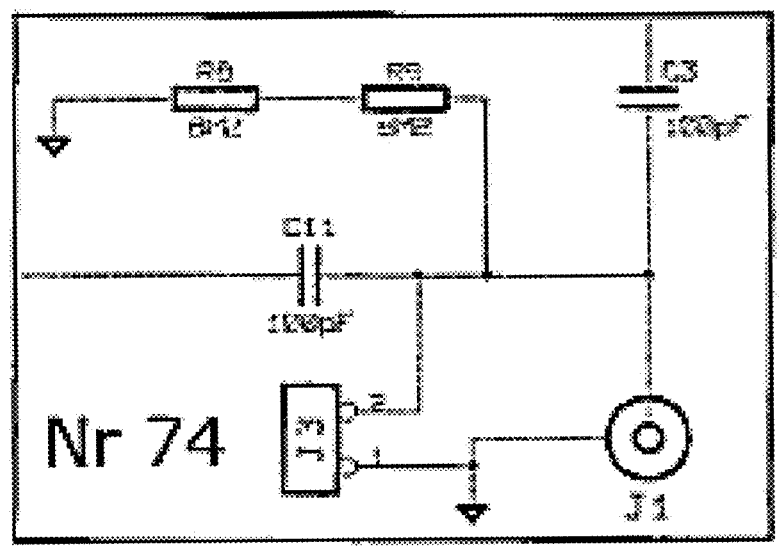
FIG. 15E Antenna.
Figure 25:
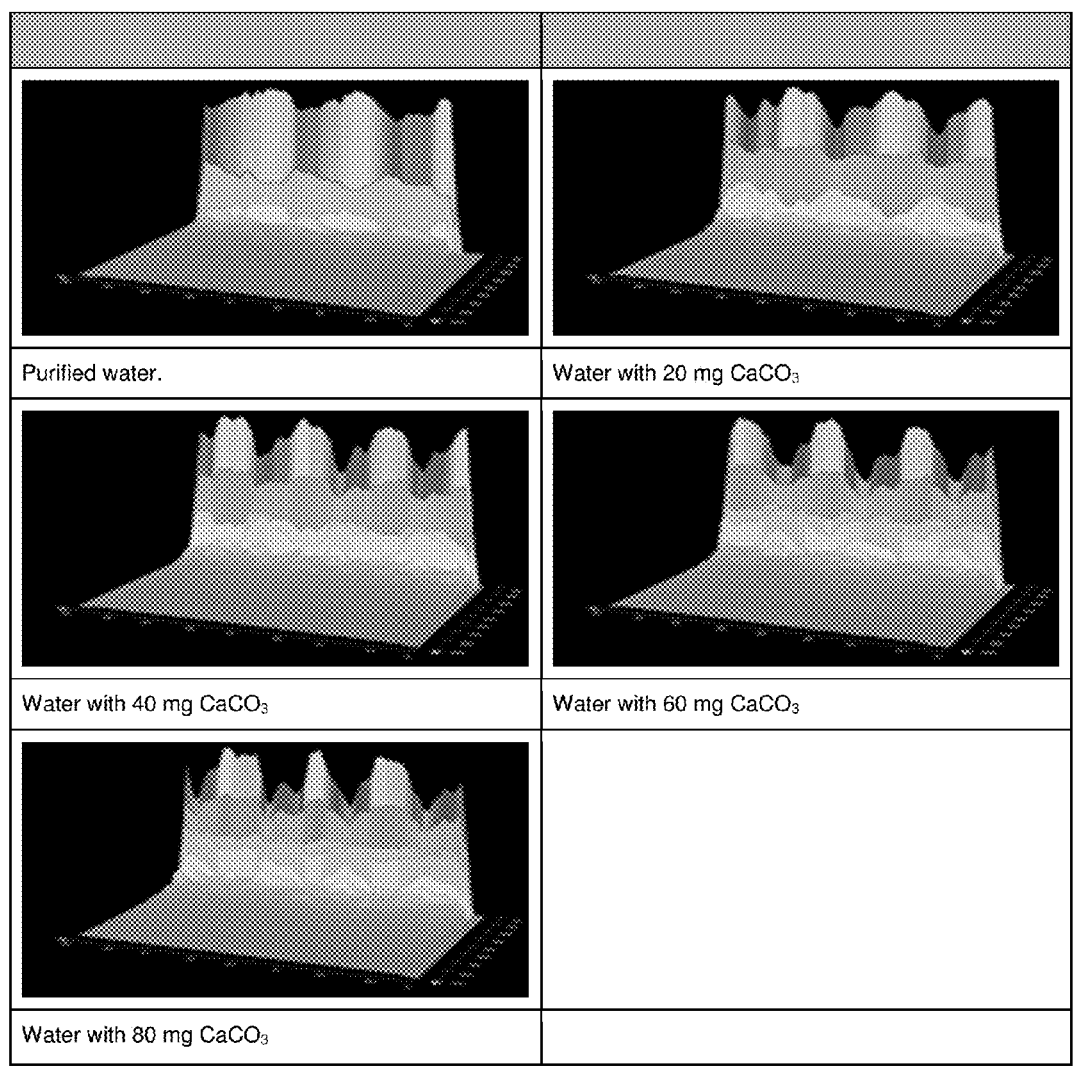
FIG. 25 Water Quality Testing—Qualitative Test.
Figure 36:
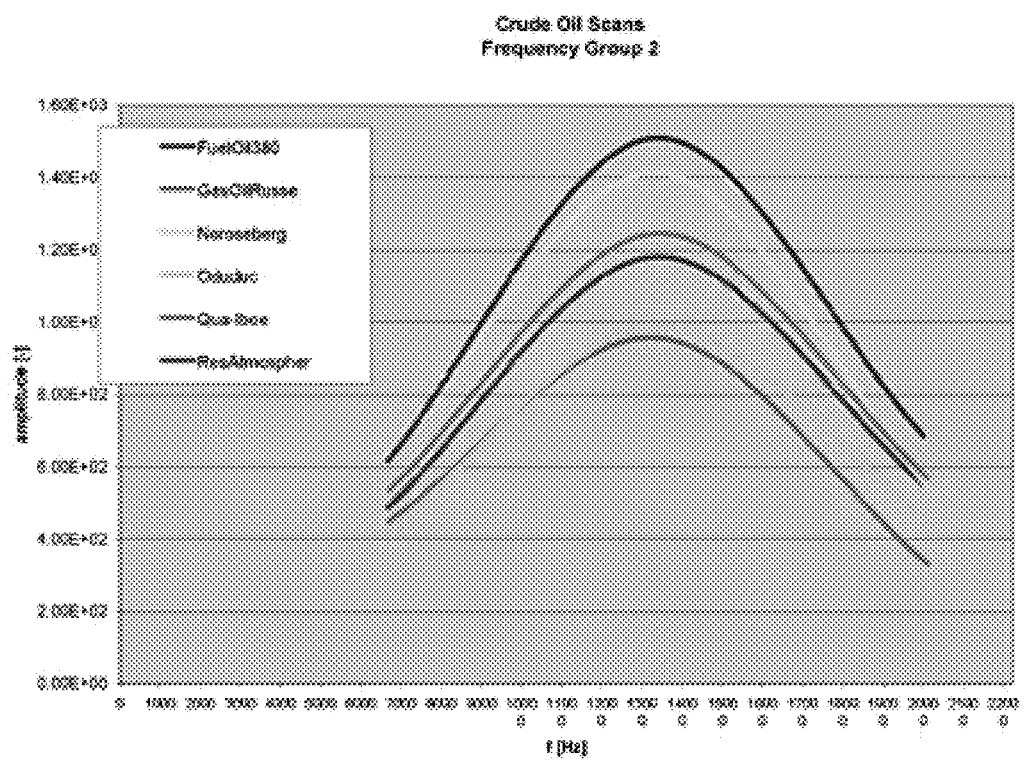
FIG. 36 Liquids Testing—Crude Oil.
Figure 54:
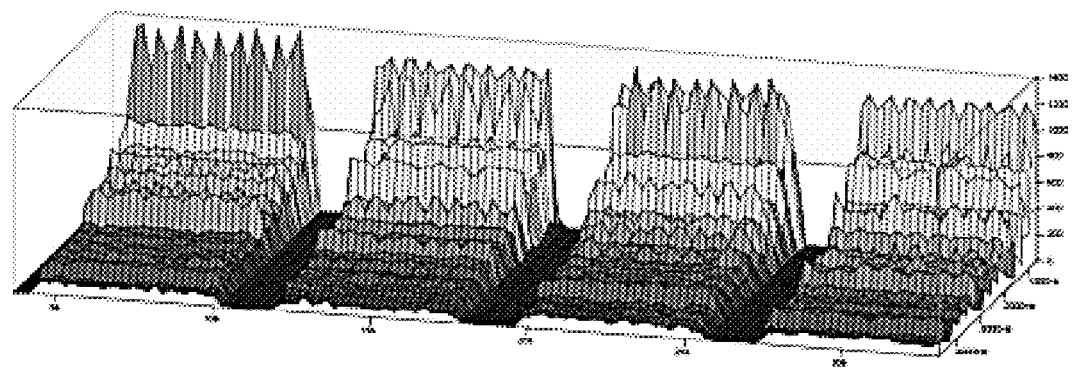
FIG. 54 Biological Testing—Human Blood Serum.
Figure 59:
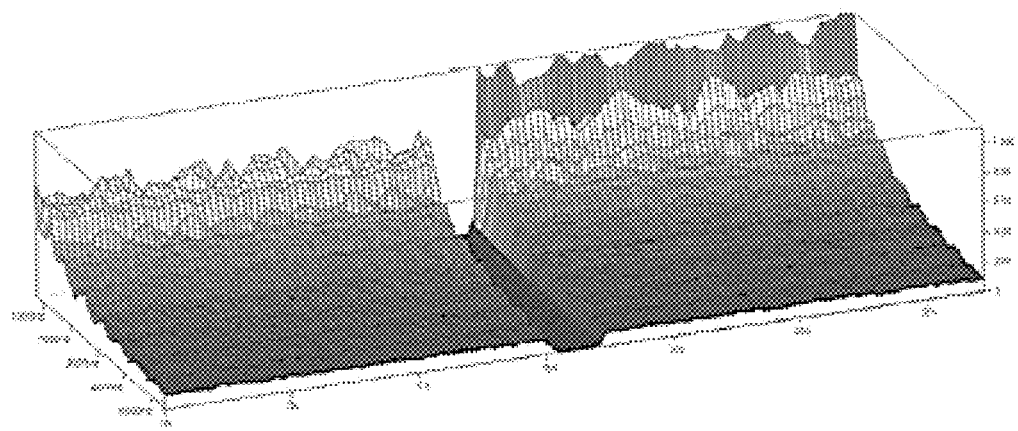
FIG. 59 Human Testing—Effects of Natural Therapies.
Figure 63:
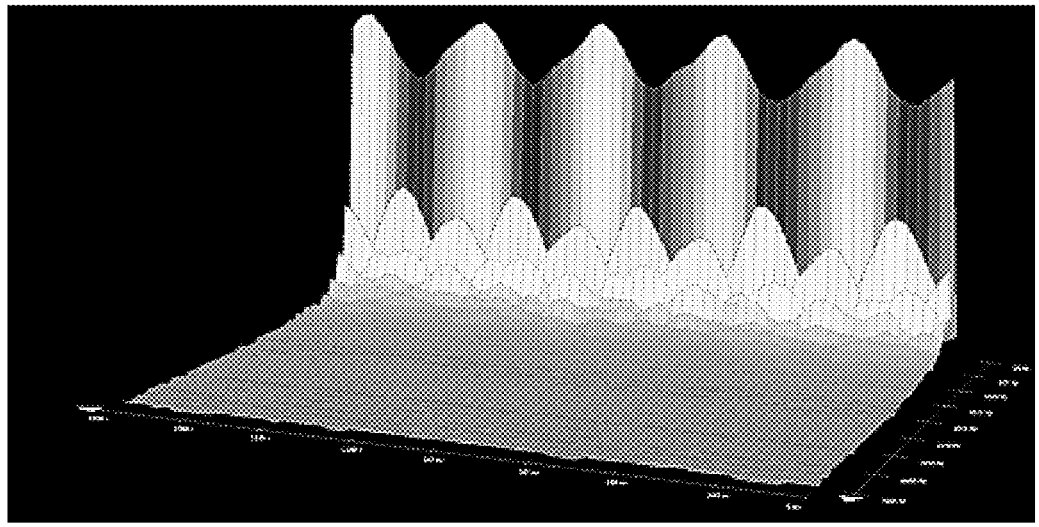
FIG. 63 spectrum for Ambrosia.
Figure 64:
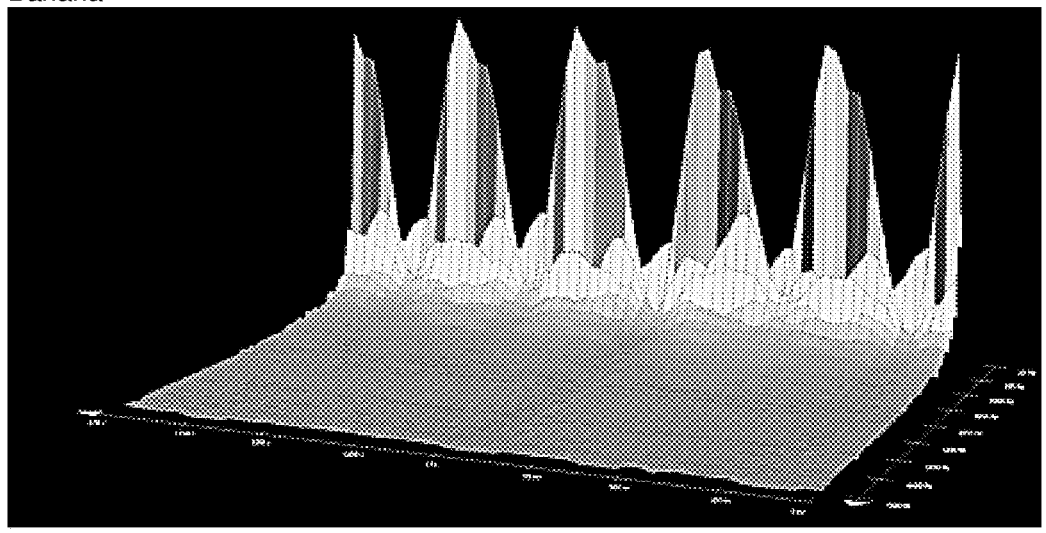
FIG. 64 spectrum for Banana.

Referring now to FIG. 15, in a second preferred embodiment of the bioharmonic detection system, the signal generator and the final amplified signal are optically coupled respectively by opto-isolator components, hence disconnecting the bioharmonic detection system from any electrical influence or disturbance that could be caused by an external power supply, ground hum, electrical interference, etc. In addition the power-supply for the circuitry is also optically coupled.

While in the first preferred embodiment the signal generator may be powered through an external electrical source such as a well known USB port or other external voltage supply and where the current is directly electrically coupled to the ground plane resonator, in the second embodiment as shown in FIG. 15, the external signal generator's output 70 is connected to a first light emitting diode 71, where the power of the square pulse is converted to light. The first light emitting diode 71 is part of a first opto-isolator 72, the first light cell 73 of which produces an electrical current to power the decoupled electrical antenna circuit 74 that is a circuit corresponding to the second module of the first preferred embodiment.

The output from the electrical antenna circuit 74 is fed to a second resonator circuit 75 that is a circuit corresponding to the ground plane resonator circuit 10 of the first preferred embodiment.

The output of the second resonator circuit 75 is fed to a second light emitting diode 76 which is part of an opto-isolator 77, the light of which causes the light cell 78 to produce an electrical current. The output of the second opto-isolator 77 is converted into an electrical audio frequency signal. As a result of optical signal coupling, the bioharmonic detector circuit, the excitation oscillator signal, the antenna, and the entire resonator modules are completely electrically isolated, i.e., there is no electrical connection between the circuit power (Vcc), signal emission (via the electrode), and signal output.

Basic Principle of Operations for the Antennas (Electrode)

The basic principle of operation is that the square wave signal is emitted via the antenna or electrode to a liquid or biological sample under test. In the range of audio frequencies, the signal at the antenna changes polarity according to the charge and discharge of the coupling capacitor(s) 8. Due to the fact that the bioharmonic detection system comprises a tunable resonator, once the appropriate frequency is selected and the tuning potential adjusted, the system will enter into a state of low frequency resonant oscillation.

One of the determining factors for signal detection, capture and measurement is the geometry of the antenna and its direct coupling or its indirect coupling via proximity to the sample. There are multiple ways in which the antenna can be used and applied. The resonance frequency of the detected signals' harmonic content depends also on how the antenna is applied. The excitation signal emitted from the antenna in fact is caused by a low power variance in electrical charge on the surface of the antenna.

The varying electrical charge on the antenna surface creates a low frequency excitation signal. The resonance of the system is determined by coupling of the varying electrical field on the surface of the antenna, and the total electrical charge of the system at test. This causes the antenna to be used for applying a varying electrical charge to the surface to the antenna at a determined audio frequency.

If we look at electrical charge as an action, we can compare the functioning of the system which stimulates a biological sample to the striking of a bell—when we strike a bell in a particular fashion, we have the response back from the bell. And we have different responses from the bell when we strike the bell in different ways such as striking it with a wooden stick, a metal rod, or a padded mallet. Similarly by changing the information with which we stimulate the biological system, we extract different aspects of the biological system's electrical information in the way of variation in harmonic content.

Changing the harmonic content or the electrical harmonic information in the waveform that we use for stimulation, i.e. excitation, can be compared to the focus parameter of an optical microscope or telescope. Thus this relationship is very important, because as we change the frequency and the information contained in the excitation signal waveform in the form of harmonics, on the same test sample, we can extract different modes of information.

A variety of antenna types may be used to perform different types of tests and are application specific. The 150 mm acupuncture needle, for example, is the simplest type of electrode geometry that we can find. The surface is extremely small with basically a pin point contact to a biological system. We have to consider that the electrical field around biological organisms is not 2-dimensional but 4-dimensional, i.e., it has the 3-dimensions of space and 1 dimension of time. As such, the electrical field can be characterized by its height, its width, its depth but also by its changes across time. It is obvious that rather than being static, the electrical field in biological systems is dynamic. These dynamic aspects are what we see in bioharmonic signals: we observe the electrical charges and information, in the form of spectral content, undulating back and forth between positive and negative polarities, increasing and decreasing amplitudes, and the time variant changes in spectral phase. Hence the content of information which can be displayed at relatively low frequencies within liquids, biological systems and bioactive matter.

A single antenna, such as the needle, gives us a one point reading of what in fact is a four dimensional electrical state of the system. This is because we are capturing at a single point on the sample. We see that if we were to measure, for example, a plant and we couple the electrode at different points on the plant's surface, we will capture different information, because we have to imagine that all biological systems have a four dimensional field, which is not only pulsing axially i.e. moving inwards and outwards from the surface of the plant, but also radially i.e. the electrical field information rotates in different directions around the plant. Thus unique geometries of electrodes or antennas are used under different conditions to capture specific characteristics, reactions and behavior of biological interactions.

The uses described for the bioharmonic detection system are possible as each biological system or bioactive substance is based on a certain physical and molecular structure whereby atoms are arranged in a macroscopic configuration. In addition, any organic molecular structure has a complex molecular geometry coupled with bipolar water molecules which thus reacts to minute changes in the electrical potential on a local or global scale, including those of electrochemical interactions due to the polarizing effects of electromagnetic waves, and the mechanical motions induced by sound or other vibrations.

The bioharmonic detection system can be applied in many different ways specifically in fields related to biological research, agronomy, animal husbandry, food processing, wine making, water management, and industrial processes involving water and the processing of biological materials.

The output signal of the bioharmonic detection system can be recorded by an analog or digital audio recording apparatus such as a computer, digital audio recorder, magnetic tape recorder, or analog disk recorder.

The bioharmonic signal can be analyzed using standard signal analysis software containing functions such as DFT (Discrete Fourier Transform) or FFT (Fast Fourier Transform) in order to extract the spectral content information including frequency response, spectral amplitude, and phase values.

The bioharmonic signal can be analyzed using a spectrum analyzer.

The bioharmonic detection system can be used in a production environment where the monitoring of ingredient quality is necessary such as in a food processing plant.

The bioharmonic detection system can be used in a production environment where the monitoring of constant water quality is necessary such example is a municipal water distribution network.

The bioharmonic detection system can be used in a production environment where the monitoring for specific water quality is necessary such example is in the manufacturing of metals, plastics and electronics.

The bioharmonic detection system can be used in a production environment where the monitoring for specific plant quality is necessary such example is in the manufacturing of cosmetics where specific enzymes are extracted from plant ingredients.

The bioharmonic detection system can be used in a production environment where the monitoring for specific plant quality is necessary such example is in the detection of chemical, fungal, viral, or bacterial contamination of fresh and dried fruits and nuts, vegetables, meats, fish and poultry.

The bioharmonic detection system can be used in a production environment where the monitoring for specific biological morphology is necessary such example is in the differentiation between male and female segments of an animal or vegetal species.

The bioharmonic detection system can be used in a production environment where the monitoring for specific liquid or biological substances is necessary such example is in the detection of liquids and biological matter in shipping containers, luggage, transport containers.

The bioharmonic detection system can be used in a production environment where the monitoring for specific liquid or biological activity is necessary such example is in the production of wine where different fermentation phases are present.

The bioharmonic detection system can be used in a research and development environment where the monitoring of biological reactions is necessary such example is in the field of genetic engineering, and the development of new chemical and biological agents.

The bioharmonic detection system can be used in a medical environment where the monitoring of biological and biophysical reactions is necessary such example is in hospitals, clinics, physiotherapy and psychotherapy settings.

The bioharmonic detection system can be used in a medical environment where the monitoring of biological and biophysical reactions is necessary such example is in the testing of patient reactions to medical implants, medications, and drug therapies.

The bioharmonic detection system can be used in a medical environment where the monitoring of biological and biophysical reactions is necessary such example is in the testing of patient biocompatibility and allergy reactions to foodstuffs, cosmetics, clothing and contact with physical objects.

The bioharmonic detection system can be used in a therapeutic environment where the monitoring of biological and biophysical reactions is necessary such example is in the testing of patient reactions to psychological stimulus, stress, noise, and electromagnetic radiation.

The bioharmonic detection system can be used in a therapeutic environment where the monitoring of biological and biophysical reactions is necessary such example is in the field of natural therapies such as acupuncture, massage, kinesiology, neuro linguistic programming, flower, plant and essential oil remedies.

The bioharmonic detection system can be used in a sports environment where the monitoring of biological and biophysical reactions is necessary such example is in the testing of athletes before and after training, the effects of clothing and equipment, the effects of dietary supplements.

The bioharmonic detection system can be used in an architectural environment where the monitoring of biological and biophysical reactions is necessary such example is in testing the effects of building materials, room geometries, effects of light, effects of sound, the effects of furniture and fixtures.

The bioharmonic detection system can be used in an architectural environment where the monitoring of biological and biophysical reactions is necessary such example is in the monitoring of rooms, auditoriums, laboratories, warehouses, offices, swimming pools and perimeters for the presence of people.

The bioharmonic detection system can be used in an automotive environment where the monitoring of biological and biophysical reactions is necessary such example is in the detection of specific drivers, the presence of children or infants in the vehicle, the presence of individuals in the vehicle perimeter.

The bioharmonic detection system can be used in an entertainment environment such as theme park, virtual reality or computer game application, where the monitoring of biological and biophysical reactions is necessary such example is in the detection of human presence, movement, and intention.

The bioharmonic detection system can be used in an entertainment environment such as toys where the monitoring of biological and biophysical reactions is necessary such example is in the detection of human presence, movement, and intention.

The bioharmonic detection system can be used in a training environment such as simulators where the monitoring of biological and biophysical reactions is necessary such example is in the detection of human presence, movement, and intention.

The bioharmonic detection system can be used in a training environment such as physical and psychological profiling where the monitoring of biological and biophysical reactions is necessary such example is in the detection of human presence, movement, and response.

The bioharmonic detection system can be used in a law enforcement environment where the monitoring of biological and biophysical reactions is necessary such example is in the detection, identification and authentication of human presence, movement, and response.

The bioharmonic detection system can be used in a military environment where the monitoring of biological and biophysical reactions is necessary such example is in the detection, identification and authentication of human presence, movement, and response.

The bioharmonic detection system can be used in a computing environment where the monitoring of biological and biophysical reactions is necessary such example is in the detection, identification and authentication of human presence, movement, and response.

The bioharmonic detection system can be used in a banking environment where the monitoring of biological and biophysical reactions is necessary such example is in the detection, identification and authentication of human presence, movement, and response.

The bioharmonic detection system can be used in a security environment where the monitoring of biological and biophysical reactions is necessary such example is in the detection, identification and authentication of human presence, movement, and response.

The bioharmonic detection system can be used in a consumer product environment where the monitoring of biological and biophysical reactions is necessary such example is in the detection, identification and authentication of human presence, movement, and response.

The bioharmonic detection system can be used in a space exploration environment where the monitoring of biological and biophysical reactions is necessary such example is in the detection and identification of liquids and biological organisms.

The bioharmonic detection system can be integrated with internal or external automation, control and monitoring modules that may provide signal waveform, frequency and calibration controls.

The bioharmonic detection system can be implemented as a sensor array containing multiple signal detector circuits and accommodating multiple electrodes or antennas, thus providing a more detailed view of a liquid or biological system behavior or interaction.

The bioharmonic detection system can be implemented as a application specific integrated circuit (ASIC) whereby the signal oscillator, resonator and amplifier circuitry can reside on a single integrated circuit.

The bioharmonic detection system can be implemented as a sensor array on an application specific integrated circuit (ASIC) whereby multiple signal oscillator, resonator and amplifier circuitry can reside on a single integrated circuit.

The bioharmonic detection system can be implemented as an electro-chemical system whose electrical properties are engineered to have identical properties as the electronic circuit described.

The bioharmonic detection system can be implemented as an electro-biological system whose electrical properties are engineered to have identical properties as the electronic circuit described.

The invention claimed is:

1. A bioharmonic signal detection system for measuring a dynamic low frequency electrical field that surrounds biological systems, liquids, and bioactive materials, comprising:
   a signal oscillator generating an oscillation signal;
   an antenna coupled to a sample to receive the electrical field that corresponds to a measurement of the bioharmonic signal and coupled to the oscillation signal;
   a tunable resonator circuit that receives a signal from the antenna;
   a ground plane resonator circuit that receives an output from the tunable resonator circuit; and
   an amplifier that receives an output from the ground plane resonator circuit and amplifies a signal from the ground plane resonator circuit corresponding to the electrical field;
   wherein the tunable resonator circuit, the ground plane resonator circuit and the amplifier are grounded to a common potential which is configured to be floating.

2. The bioharmonic detection system of claim 1, wherein the signal oscillator includes a variable square pulse wave generator.

3. The bioharmonic detection system of claim 1, wherein a frequency of the signal output by the signal generator has a value below 2 kHz.

4. The bioharmonic detection system of claim 1,
   wherein the tunable resonator further comprises of connection in series to a first coupling capacitor, a second coupling capacitor, a resonator circuit,
   wherein the resonator circuit comprises a potentiometer and an inductance to adjust a resonance frequency of the tunable resonator, and the first coupling capacitor, the second coupling capacitor and the antenna have a common connection which is grounded via a grounding resistor to the common potential.

5. The bioharmonic detection system of claim 4, wherein the grounding resistor has a value greater of equal to 20 M Ohm.

6. The bioharmonic detection system of claim 1, wherein the ground plane resonator circuit comprises a first inverter, a diode, a second inverter, and a low pass filter circuit connected at its input to a connection between the diode and the second inverter and at its output to the common potential.

7. The bioharmonic detection system of claim 6 wherein the low pass filter comprises a second resistor and a capacitor.

8. The bioharmonic detection system according to claim 1, wherein the amplifier comprises at least a third resistor, a darlington transistor, and produces an output for an audio transducer.

9. A method of using the bioharmonic detection system as claimed in claim 1, comprising the steps of:
   detecting and identifying a presence of specific types of biological organisms including at least one of fungi, plants, fish, birds, insects, animals, and people.

10. A method for using the bioharmonic detection system as claimed in claim 1 comprising the steps of:
    detecting and identifying specific types of responses in a biological system including a reaction of a biological system to an applied physical, chemical or electromagnetic stimulus.

11. The bioharmonic detection system of claim 1, wherein a frequency of the signal output by the signal generator has a value below 500 Hz.

12. The bioharmonic detection system of claim 1, wherein the ground plane resonator circuit removes a negative polarity of the signal.

13. The bioharmonic detection system of claim 1, wherein the ground plane resonator circuit includes a low-pass filter.

14. The bioharmonic detection system of claim 1, wherein the ground plane resonator circuit comprises a first inverter, a diode, and a second inverter connected in series.

* * * * *